United States Patent [19]
Edwin et al.

[11] Patent Number: 6,039,755
[45] Date of Patent: Mar. 21, 2000

[54] RADIALLY EXPANDABLE TUBULAR POLYTETRAFLUOROETHYLENE GRAFTS AND METHOD OF MAKING SAME

[75] Inventors: Tarun J. Edwin; Fariba Hurry, both of Tempe; Christopher E. Banas, Mesa, all of Ariz.

[73] Assignee: Impra, Inc., a Division of C.R. Bard, Inc., Tempe, Ariz.

[21] Appl. No.: 08/794,871

[22] Filed: Feb. 5, 1997

[51] Int. Cl.$^7$ .................................. A61F 2/06; A61F 2/04
[52] U.S. Cl. ..................................... 623/1; 623/12; 600/36
[58] Field of Search .................................. 623/1, 11, 12; 606/151–158, 193, 194; 600/36

[56] References Cited

U.S. PATENT DOCUMENTS

| | | | |
|---|---|---|---|
| Re. 31,341 | 8/1983 | Koizumi et al. ........................... | 526/73 |
| 612,897 | 10/1898 | Ellis . | |
| 2,642,625 | 6/1953 | Peck ........................................ | 18/47.5 |
| 3,060,517 | 10/1962 | Fields ........................................ | 18/55 |
| 3,196,194 | 7/1965 | Ely, Jr. et al. ............................ | 264/95 |
| 3,207,601 | 9/1965 | Barry ........................................ | 18/57 |
| 3,281,511 | 10/1966 | Goldsmith ................................. | 264/49 |
| 3,767,500 | 10/1973 | Tally et al. ............................... | 156/184 |
| 3,887,761 | 6/1975 | Gore .................................... | 174/110 R |
| 3,992,725 | 11/1976 | Homsy . | |
| 4,061,517 | 12/1977 | Dutton, III ............................... | 156/212 |
| 4,416,028 | 11/1983 | Eriksson et al. ........................... | 3/1.4 |
| 4,503,569 | 3/1985 | Dotter ........................................ | 3/1.4 |
| 4,512,338 | 4/1985 | Balko et al. ............................. | 128/1 R |
| 4,580,568 | 4/1986 | Gianturco ................................. | 128/345 |
| 4,596,837 | 6/1986 | Yamamoto ............................... | 521/145 |
| 4,647,416 | 3/1987 | Seiler, Jr. et al. ....................... | 264/118 |
| 4,655,769 | 4/1987 | Zachariades ............................. | 623/1 |
| 4,714,748 | 12/1987 | Hoashi et al. ........................... | 526/255 |
| 4,731,073 | 3/1988 | Robinson .................................... | 623/1 |
| 4,733,665 | 3/1988 | Palmaz .................................... | 128/343 |
| 4,739,762 | 4/1988 | Palmaz .................................... | 128/343 |
| 4,760,102 | 7/1988 | Moriyama ............................... | 521/145 |

(List continued on next page.)

FOREIGN PATENT DOCUMENTS

| | | |
|---|---|---|
| 0 221 570 | 5/1987 | European Pat. Off. .......... A61F 2/04 |
| 0 335 341 | 10/1989 | European Pat. Off. .......... A61F 2/06 |
| 0 461 791 | 12/1991 | European Pat. Off. .......... A61F 2/06 |
| 0 551 179 | 7/1993 | European Pat. Off. .......... A61F 2/06 |
| 0 646 365 | 4/1995 | European Pat. Off. .......... A61F 2/06 |
| 0 648 869 | 4/1995 | European Pat. Off. .......... D01F 6/12 |
| 0 656 196 | 6/1995 | European Pat. Off. .......... A61F 2/06 |
| 0 662 307 | 7/1995 | European Pat. Off. .......... A61F 2/06 |
| 0 667 132 | 8/1995 | European Pat. Off. .......... A61F 2/06 |

(List continued on next page.)

OTHER PUBLICATIONS

"Transfemoral Intraluminal Graft Implantation for Abdominal Aortic Aneurysms" by J. Parodi, J. Palmaz, and H. Barone, *Annals of Vascular Surgery*, vol. 5, No. 6, pp. 491–499 (1991).

"Endoluminal stented graft aorto–bifemoral reconstruction" by M. Marin and F. Veith, *Vascular and Endovascular Surgical Techniques, An Atlas* Third Edition pp. 100–104 (1994).

"Bifurcated endovascular graft insertion for abdominal aortic aneurysm" by T. Chuter, *Vascular and Endovascular Surgical Techniques, An Atlas* Third Edition pp. 92–99 (1994).

(List continued on next page.)

*Primary Examiner*—Debra S. Brittingham
*Attorney, Agent, or Firm*—David G. Rosenbaum; Sonnenschein, Nath & Rosenthal

[57] ABSTRACT

Tubular ePTFE materials which are capable of being radially expanded under the influence of a radially outward force applied from the lumen of the ePTFE tubular material to substantially uniformly radially deform the ePTFE material. The ePTFE material is radially expandable to a diameter 700% its unexpanded diameter under the influence of pressures less than 6 atm while retaining the structural integrity of the ePTFE microstructure. Conservation of the structural integrity of the ePTFE material is determined by conservation of the ePTFE microstructure structural integrity.

14 Claims, 42 Drawing Sheets

U.S. PATENT DOCUMENTS

| | | | |
|---|---|---|---|
| 4,776,337 | 10/1988 | Palmaz | 128/344 |
| 4,816,339 | 3/1989 | Tu et al. | 623/1 |
| 4,830,062 | 5/1989 | Yamamoto | 138/177 |
| 4,922,905 | 5/1990 | Strecker | 606/195 |
| 4,955,899 | 9/1990 | Della Corna | 623/901 |
| 4,957,669 | 9/1990 | Primm | 264/23 |
| 4,969,896 | 11/1990 | Shors | 623/1 |
| 5,061,276 | 10/1991 | Tu et al. | 623/1 |
| 5,071,609 | 12/1991 | Tu et al. | 264/119 |
| 5,078,726 | 1/1992 | Kreamer | 606/194 |
| 5,084,065 | 1/1992 | Weldon et al. | 623/1 |
| 5,102,417 | 4/1992 | Palmaz | 606/195 |
| 5,122,154 | 6/1992 | Rhodes | 606/198 |
| 5,123,917 | 6/1992 | Lee | 623/1 |
| 5,152,782 | 10/1992 | Kowligi et al. | 623/1 |
| 5,156,620 | 10/1992 | Pigott | 623/1 |
| 5,163,951 | 11/1992 | Pinchuk et al. | 623/1 |
| 5,171,805 | 12/1992 | Tatemoto | 526/252 |
| 5,195,984 | 3/1993 | Schatz | 606/195 |
| 5,211,658 | 5/1993 | Clouse | 606/191 |
| 5,219,355 | 6/1993 | Parodi et al. | 606/191 |
| 5,234,739 | 8/1993 | Tanaru et al. | 428/131 |
| 5,282,848 | 2/1994 | Schmitt | 623/1 |
| 5,282,860 | 2/1994 | Matsuno et al. | 623/12 |
| 5,316,023 | 5/1994 | Palmaz | 128/898 |
| 5,330,500 | 7/1994 | Song | 606/198 |
| 5,334,201 | 8/1994 | Cowan | 623/1 |
| 5,354,329 | 10/1994 | Whalen | 623/1 |
| 5,360,443 | 11/1994 | Barone et al. | 623/1 |
| 5,376,110 | 12/1994 | Tu et al. | 623/1 |
| 5,382,261 | 1/1995 | Palmaz | 606/194 |
| 5,383,926 | 1/1995 | Lock et al. | 623/1 |
| 5,385,580 | 1/1995 | Schmitt | 623/1 |
| 5,387,235 | 2/1995 | Chuter | 623/1 |
| 5,387,236 | 2/1995 | Noishiki | 623/1 |
| 5,389,106 | 2/1995 | Tower | 606/198 |
| 5,405,377 | 4/1995 | Cragg | 623/1 |
| 5,429,869 | 7/1995 | McGregor | 428/364 |
| 5,433,996 | 7/1995 | Kranzler et al. | 428/247 |
| 5,449,373 | 9/1995 | Pinchasik et al. | 606/198 |
| 5,464,438 | 11/1995 | Menaker | 623/1 |
| 5,464,440 | 11/1995 | Johansson | 623/16 |
| 5,464,449 | 11/1995 | Ryan et al. | 623/1 |
| 5,489,295 | 2/1996 | Piplani et al. | 623/1 |
| 5,496,364 | 3/1996 | Schmitt | 623/1 |
| 5,507,771 | 4/1996 | Gianturco | 606/198 |
| 5,522,883 | 6/1996 | Slater et al. | 623/1 |
| 5,527,353 | 6/1996 | Schmitt | 623/1 |
| 5,527,355 | 6/1996 | Ahn | 623/1 |
| 5,540,712 | 7/1996 | Kleshinski | 606/198 |
| 5,540,713 | 7/1996 | Schnepp-Pesch | 606/198 |
| 5,549,663 | 8/1996 | Cottone, Jr. | 623/1 |
| 5,556,414 | 9/1996 | Turi | 606/198 |
| 5,571,170 | 11/1996 | Palmaz et al. | 623/108 |
| 5,571,171 | 11/1996 | Barone et al. | 623/1 |
| 5,571,173 | 11/1996 | Parodi | 623/1 |
| 5,591,197 | 1/1997 | Orth et al. | 606/198 |
| 5,591,223 | 1/1997 | Lock et al. | 623/1 |
| 5,591,224 | 1/1997 | Schwartz et al. | 623/1 |
| 5,591,228 | 1/1997 | Edoga | 623/1 |
| 5,591,229 | 1/1997 | Parodi | 623/1 |

FOREIGN PATENT DOCUMENTS

| | | | |
|---|---|---|---|
| 39 18 736 A1 | 12/1990 | Germany | A61F 2/06 |
| 1 505 591 | 3/1978 | United Kingdom | A61F 1/24 |
| 9505132 | 2/1995 | WIPO | 623/1 |
| WO95/05132 | 2/1995 | WIPO | A61F 2/06 |
| WO95/05277 | 2/1995 | WIPO | B29C 51/04 |
| WO95/05555 | 2/1995 | WIPO | F16L 11/08 |
| WO96/33066 | 10/1996 | WIPO | B29D 23/00 |

OTHER PUBLICATIONS

"Use of Stents Covered with Polytetrafluoroethylene in Experimental Abdominal Aortic Aneurysm" by J. Palmaz, et al., *JVIR*, vol. 6, pp. 879–885 (1995).

"Physical Properties of Polytetrafluoroethylene Bypass Material after Balloon Dilation" by F. Palmaz, E. Sprague, and J. Palmaz, *JVIR*, vol. 7, pp. 657–663 (1996).

"Cardiovascular implants—Vascular prostheses" by the Association for the Advancement of Medical Instrumentation, *ANSI/AMI*, vol. 20 (1994).

"The melting temperature of polytetrafluoroethylene" by Y.P. Khanna, *Journal of Materials Science Letters*, vol. 7, pp. 817–818 (1988).

"Glass Transition of Poly(tetrafluoroethylene)" by Suk Fai Lau, J. Wesson and B. Wunderlich, *Macromolecules*, vol. 17, pp. 1102–1104 (1984).

"The Density of Amorphous Polytetrafluoroethylene" *Journal of Polymer Science: Polymer Physics Edition*, vol. 20, pp. 2159–2161 (1982).

"A New Differential Scanning Calorimetry Based Approach for the Estimation of Thermal Conductivity of Polymer Solids and Melts" by Y.P. Khanna, T.J. Taylor, and G. Chomyn, *Polymer Engineering and Science*, vol. 28, No. 16, pp. 1034–1041 (Aug. 1988).

"The Thermodynamic Properties of Polytetrafluoroethylene" by Suk Fai Lau, H. Suzuki, and B. Wunderlich, *Journal of Polymer Science: Polymer Physics Edition*, vol. 22, pp. 379–405 (1984).

"A Study on the Thermal Behaviour and Structural Characteristics of Polytetrafluoroethylene" by V. Villani, *Thermochimica Acta*, vol. 162, pp. 189–193 (1990).

"Characterization of the crystallinity of polytetrafluoroethylene by X–ray and IR spectroscopy, differential scanning calorimetry, viscoelastic spectroscopy and the use of a density gradient tube" by Ting–Yung Hu, *Wear*, vol. 82, pp. 369–376 (1982).

"International Congress VIII on Endovascular Interventions 'Breaking Barriers'" *Journal of Endovascular Surgery*, vol. 2, No. 1, pp. 89–129 (Feb. 1995).

"Endoluminal Grafting for Percutaneous Aneurysm Exclusion in an Aortocoronary Saphenous Vein Graft: The First Clinical Experience" by R. Heuser, G. Reynolds, C. Papazoglou, and E. Diethrich, *Journal of Endovascular Surgery*, vol. 2, No. 1, pp. 81–88 (Feb. 1995).

"Closure of a Popliteal Arteriovenous Fistula Using an Autologous Vein–Covered Palmaz Stent" by G. Dorros, and G. Joseph, *Journal of Endovascular Surgery*, vol. 2, No. 2, pp. 177–181 (May 1995).

"Transbrachial Endovascular Exclusion of an Axillary Artery Pseudoaneurysm with PTFE–Covered Stents" by W. Marston, E. Criado, M. Maura, and B. Keagy, *Journal of Endovascular Surgery*, vol. 2, No. 2, pp. 172–176 (May 1995).

"Endoluminal Grafting for Aneurysmal and Occlusive Disease in the Superficial Femoral Artery: Early Experience" by E. Diethrich and K. Papazoglou, *Journal of Endovascular Surgery*, vol. 2, No. 3, pp. 225–239 (Aug. 1995).

"Transluminally placed endovascular stented graft repair for arterial trauma" by M. Marin, F. Veith, T. Panetta, J. Cynamon, L. Sanchez, M. Schwartz, R. Lyon, C. Bakal, and W. Suggs, *The Journal of Vascular Surgery on Compact Disc* (1994–1995).

"Uses of balloon expandable stents in combination with PTFE" by J. Palmaz, *Vascular and Endovascular Surgical Techniques, An Atlas* Third Edition pp. 36–42 (1994).

"Transluminal placement of a prosthetic graft–stent device for treatment of subclavian artery aneurysm" by J. May, G. White, R. Waugh, W. Yu, and J. Harris, *Journal of Vascular Surgery*, vol. 18, No. 6, pp. 1056–1059 (Dec. 1993).

"Percutaneous Femoropopliteal Graft Placement" by A. Craigg and M. Dake, *Radiology*, vol. 187, No. 3, pp. 643–648 (Jun. 1993).

"Percutaneous Femoropopliteal Graft Placement: Is This the Next Step?" by M. Shapiro and D. Levin, *Radiology*, vol. 187, No. 3, pp. 618–619 (Jun. 1993).

"Transfemoral intraluminal graft implantation for abdominal aortic aneurysms" by J. Parodi, pp. 71–77.

"Transfemoral endovascular repair of abdominal aortic aneurysm using the endovascular graft system device", by W. Moore, *Vascular and Endovascular Surgical Techniques, An Atlas* Third Edition pp. 78–91 (1994).

PCT International Search Report in PCT/US95/11817, Jul. 17, 1996.

RADIALLY EXPANDABLE TUBULAR POLYTETRAFLUOROETHYLENE GRAFTS AND METHOD OF MAKING SAME

BACKGROUND OF THE INVENTION

The present invention relates generally to longitudinally expanded microporous tubular polytetrafluoroethylene grafts, and more particularly, to radially expandable polytetrafluoroethylene ("rePTFE") grafts which are longitudinally expanded and sintered prior to radial expansion. The radially expandable polytetrafluoroethylene grafts of the present invention are particularly well suited for covering an endoluminal prosthesis, being endoluminally delivered to a site within a mammalian body, and radially expanded in vivo to restore an anatomical passageway or to create a passageway.

Microporous expanded polytetrafluoroethylene ("ePTFE") tubes may made by any one of different, but well known, methods. Expanded polytetrafluoroethylene is typically made by admixing particulate dry polytetrafluoroethylene resin with a lubricant to form a viscous slurry. The admixture is poured into a mold, typically a cylindrical mold, and compressed under the influence of a positive pressure to form a cylindrical billet. The billet is then ram extruded through an extrusion die into either tubular or sheet structures termed in the art as extrudates. The extrudates consist of extruded polytetrafluoroethylene-lubricant admixture, termed in the art as "wet PTFE." Wet PTFE has a microstructure of coalesced, coherent PTFE resin particles in a highly crystalline state. After extrusion, the wet PTFE is exposed to a temperature below the flash point of the lubricant to volatilize a major fraction of the lubricant from the PTFE extrudate. The resulting PTFE extrudate without a major fraction of lubricant is known in the art as dried PTFE. The dried PTFE is then either uniaxially, biaxially or radially expanded using appropriate mechanical apparatus known in the art. Expansion is typically carried out at an elevated temperature, e.g., above room temperature but below 327° C., the crystalline melt point of polytetrafluoroethylene. Uniaxial, biaxial or radial expansion of the dried PTFE causes the coalesced, coherent PTFE resin to form fibrils emanating from nodes, with the fibrils oriented parallel to the axis of expansion. Once expanded, the dried PTFE is referred to as expanded PTFE ("ePTFE") or microporous PTFE. The ePTFE is then transferred to a heating oven and heated to a temperature above 327° C., the crystalline melt point of PTFE, while restraining the ePTFE against uniaxial, biaxial radial contraction, to sinter the ePTFE, thereby causing at least a portion of the crystalline PTFE to undergo a physical change from a crystalline structure to an amorphous structure. The conversion from a highly crystalline structure to an increased amorphous content, which results from sintering, serves to lock the node and fibril microstructure, as well as its orientation relative to the axis of expansion, and provides a dimensionally stable tubular or sheet material upon cooling. Expansion may also be carried out at a temperature below the vapor point of the lubricant. However, prior to the sintering step, the PTFE must be dried of lubricant because the sintering temperature of PTFE is greater than the flash point of commercially available lubricants.

Sintered ePTFE articles exhibit significant resistance to further uniaxial, or radial expansion. This property has led many in the art to devise techniques which entail endoluminal delivery and placement of an ePTFE graft having a desired fixed diameter, followed by endoluminal delivery and placement of an endoluminal prosthesis, such as a stent or other fixation device, to frictionally engage the endoluminal prosthesis within the lumen of the anatomical passageway. The Kreamer patent, U.S. Pat. No. 5,078,726, issued in 1992, exemplifies such use of an ePTFE prosthetic graft. Kreamer discloses a method of excluding an abdominal aortic aneurysm which entails providing a tubular PTFE graft which has a diameter corresponding to that of the inside diameter of a healthy section of the abdominal aorta, delivering the tubular PTFE graft and positioning the graft so that it spans the abdominal aorta. Prosthetic balloon expandable stents are then delivered and placed proximal and distal the abdominal aorta and within the lumen of the tubular PTFE graft. The prosthetic stents are then balloon expanded to frictionally engage the proximal and distal ends of the tubular PTFE graft against the inner luminal wall of healthy sections of the abdominal aorta.

Similarly, published International Applications No. WO95/05132 and WO95/05555, both published Feb. 23, 1995, filed by W. L. Gore Associates, Inc., disclose balloon expandable prosthetic stents which have been covered on inner and outer surfaces of the stent by wrapping ePTFE sheet material about the balloon expandable prosthetic stent in its enlarged diameter, sintering the wrapped ePTFE sheet material to secure it about the stent, then the assembly is crimped down to a reduced diameter for endoluminal delivery using a balloon catheter. Once positioned endoluminally, the stent-graft combination is then dilatated to re-expand the stent to its enlarged diameter and return the ePTFE wrapping to its original diameter. Thus, the original unexpanded diameter of the ePTFE wrap delimits diametric expansion of the stent and the ePTFE wrap is returned to its original uncrimped diameter.

Thus, it is well known in the prior art to provide an ePTFE covering which is fabricated at the final desired endovascular diameter and is endoluminally delivered in a folded or crimped condition to reduce its delivery profile, then unfolded in vivo using either the spring tension of a self-expanding, thermally induced, expanding structural support member or a balloon catheter.

In contradistinction to the prior art, the present invention provides a radially, plastically deformable tubular ePTFE material, having a microstructure of nodes interconnected by fibrils, with the nodes being substantially perpendicular to the longitudinal axis of the tubular ePTFE material and the fibrils being oriented parallel to the longitudinal axis of the tubular ePTFE material. Radial expansion of the inventive ePTFE material deforms the ePTFE microstructure by elongating the nodes while substantially retaining the internodal distances (IND) between adjacent nodes in the longitudinal axis of the ePTFE tube.

As used herein, the following terms have the intended meanings as indicated.

"Fibril" refers to a strand of PTFE material which originates from one or more nodes and terminates at one or more nodes.

"Internodal Distance" or "IND" refers to an average distance between two adjacent nodes measured along the longitudinal axis of each node between the facing surfaces of the adjacent nodes. IND is expressed in microns ($\mu$) as the unit of measure.

"Node" refers to the solid region within an ePTFE material at which fibrils originate and converge.

"Node Length" as used herein refers to a distance measured along a straight line between the furthermost opposing end points of a single node.

"Nodal Elongation" as used herein refers to expansion of PTFE nodes in the ePTFE microstructure along the longitudinal axis of a node, or along the Node Length.

"Node Width" as used herein refers to a distance measured along a straight line drawn perpendicular to the longitudinal axis of a node between opposing longitudinal surfaces of a node.

"Plastic Deformation" as used herein refers to the radial deformation of the ePTFE microstructure under the influence of a radially expansive force which deforms and elongates the Node Length and results in elastic recoil of the ePTFE material less than about 25%.

"Radially Expandable" as used herein to describe the present invention refers to a property of the ePTFE tubular member to undergo radially-oriented Plastic Deformation mediated by Nodal Elongation.

"Structural Integrity" as used herein to describe the present invention refers to a condition of the ePTFE microstructure both pre and post-radial deformation in which the fibrils are substantially free of fractures or breaks and the ePTFE material is free of gross failures.

The inventive ePTFE material of the present invention is capable of being radially expanded under the influence of a radially outward force applied from the lumen of the ePTFE tubular material to substantially uniformly deform the ePTFE material. The inventive ePTFE material is radially expandable to a diameter 700% its unexpanded diameter under the influence of pressures less than 6 atm, preferably less than or equal to about 4.0 to 4.5 atm., most preferably between 2–3 atm., while retaining the structural integrity of the ePTFE microstructure. Conservation of the structural integrity of the ePTFE material is determined by conservation of the ePTFE microstructure structural integrity. During and after radial expansion up to and including about 700% of the original unexpanded diameter, the ePTFE microstructure structural integrity is considered conserved where the following factors are met: 1) IND remains substantially the same as the unexpanded graft; 2) water entry pressure as measured by Association for the Advancement of Medical Instrumentation (AAMI) test method 8.2.4 remains within ±60% of the water entry pressure of the unexpanded graft; 3) the wall thickness of the graft, as determined by AAMI test method 8.7.4, maintains its concentricity as determined by a substantially uniform wall thickness within ±30% about the circumference of the graft; 4) average post-radial expansion wall thickness remains within about ±70% of the average pre-radial expansion wall thickness as determined by AAMI test method 8.7.4; 5) longitudinal tensile strength as measured by AAMI test method 8.3.2 remains within ±100% of the value of the unexpanded graft, when normalized for wall thickness; 6) radial tensile strength as measured by AAMI test method 8.3.1 remains within ±40% of the value of the unexpanded graft, when normalized for wall thickness; and 7) is free of gross tears or fractures.

SUMMARY OF THE INVENTION

It is a primary objective of the present invention to provide an ePTFE tubular member which is radially expandable in vivo at radial expansion pressures less than about 6 atm. and is suitable for use as a cover or liner for an endoluminal support member, such as a self-expanding stent, shape memory stent, or balloon expandable stent.

It is another primary objective of the present invention to provide an ePTFE tubular member which is capable of being delivered intraluminally into the body in a relatively small diameter and radially expanded in vivo to act as an intraluminal anatomical liner of, for example, the vasculature, the alimentary tract, biliary ducts, hepatic-portal vein shunts, or as bypass grafts to carry body fluids around an obstructed flow path.

It is another objective of the present invention to provide a radially expandable ePTFE tubular member which is capable of percutaneous and endovascular delivery to both the coronary and peripheral vasculature in a mammalian body.

It is still another objective of the present invention to provide a radially expandable ePTFE tubular member which, after radial expansion up to about 700% its original diameter, retains its structural integrity.

It is yet another objective of the present invention to provide a radially expandable ePTFE tubular member which, after radial expansion up to about 700% its original diameter, retains the structural integrity of the ePTFE microstructure.

It is still yet another objective of the present invention to provide a radially expandable ePTFE tubular member which, after radial expansion up to about 700% its original diameter, is characterized by 1) IND remains substantially the same as the unexpanded graft; 2) water entry pressure as measured by Association for the Advancement of Medical Instrumentation (AAMI) test method 8.2.4 remains within ±60% of the water entry pressure of the unexpanded graft; 3) the wall thickness of the graft, as determined by AAMI test method 8.7.4, maintains its concentricity as determined by a substantially uniform wall thickness within ±30% about the circumference of the graft; 4) average post-radial expansion wall thickness remains within about ±70% of the average pre-radial expansion wall thickness as determined by AAMI test method 8.7.4; 5) longitudinal tensile strength as measured by AAMI test method 8.3.2 remains within ±100% of the value of the unexpanded graft, when normalized for wall thickness; 6) radial tensile strength as measured by AAMI test method 8.3.1 remains within ±40% of the value of the unexpanded graft, when normalized for wall thickness; and 7) is free of gross tears or fractures.

It is another primary objective of the present invention to provide a method of making a ePTFE tubular member which is radially expandable in vivo at radial expansion pressures less than about 6 atm. and is suitable for use as a cover or liner for an endoluminal support member, such as a self-expanding, shape memory, or balloon expandable stent, and which is characterized by any of the foregoing objectives for the radially expandable ePTFE tubular member.

DETAILED DESCRIPTION OF THE PREFERRED EMBODIMENTS

Figure 1:
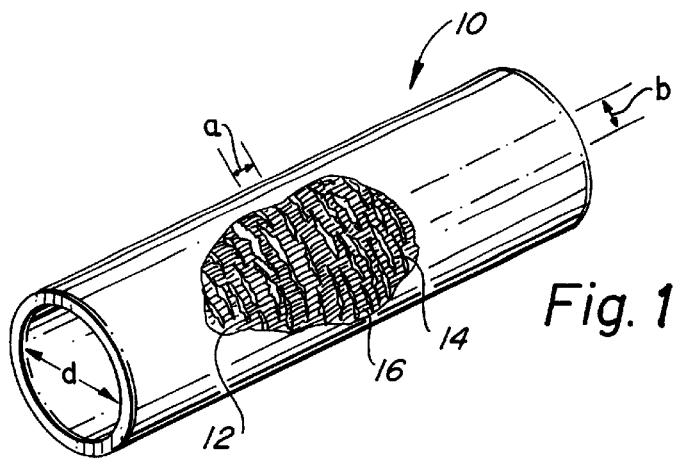
FIG. 1 is a perspective, partial cut-away view of a radially expandable ePTFE graft in accordance with the present invention diagrammatically illustrating the pre-radially expansion microstructure of the ePTFE material.

In accordance with the preferred embodiments of the present invention there is provided a longitudinally expanded polytetrafluoroethylene tubular member having a continuous substantially concentric wall surface which has no seam and which is radially deformable between about 50% to about 700% its original diameter with application of a radially directed outward pressure of less than about 6 atm, preferably less than or equal to about 4 to 4.5 atm without loss of structural integrity. Structural integrity is considered retained where the microstructure of the ePTFE after radial expansion, is substantially free of broken or fractured fibrils and where the following factors are met: 1) IND remains substantially the same as the unexpanded graft; 2) water entry pressure as measured by Association for the Advancement of Medical Instrumentation (AAMI) test method 8.2.4 remains within ±60% of the water entry pressure of the unexpanded graft; 3) the wall thickness of the graft, as determined by AAMI test method 8.7.4, maintains its concentricity as determined by a substantially uniform wall thickness within ±30% about the circumference of the graft; 4) average post-radial expansion wall thickness remains within about ±70% of the average pre-radial expansion wall thickness as determined by AAMI test method 8.7.4; 5) longitudinal tensile strength as measured by AAMI test method 8.3.2 remains within ±100% of the value of the unexpanded graft, when normalized for wall thickness; 6) radial tensile strength as measured by AAMI test method 8.3.1 remains within ±40% of the value of the unexpanded graft, when normalized for wall thickness; and 7) is free of gross tears or fractures.

As is well known in the art, longitudinally expanded polytetrafluoroethylene (ePTFE) tubular structures may be made by ram extruding a compressed billet of polytetrafluoroethylene resin and a lubricant extrusion aid through an annular orifice formed by an extrusion die and a mandrel to form a tubular extrudate. The tubular extrudate is free of seams, overlaps, crimps, folds, or the like. While the tubular extrudate still contains the lubricant it is referred to as being "wet." The wet extrudate lacks dimensional stability, is easily damaged, and is difficult to manipulate or otherwise process without removing the lubricant. Typically lubricant is removed and the extrudate "dried" by heating the wet extrudate to a temperature below the flash point of the lubricant and below the crystalline melt temperature of the PTFE resin which volatilizes the lubricant from the PTFE resin. Dimensional stability and the degree to which the extrudate may be manipulated or processed is related to the concentration of lubricant in the extrudate. Thus, the extrudate may be partially or fully dried, depending upon the residual lubricant concentration desired, by varying the dwell or residence time of the wet extrudate in the drying oven.

Once the extrudate is dried to the extent desired, the dried extrudate is longitudinally expanded at a temperature below the crystalline melt temperature of the PTFE resin. Longitudinal expansion is performed at a rate of between about 5%/sec. to about 800%/sec. with the final expansion ratio being between 2:1 to 6:1. The ends of the longitudinally expanded PTFE are constrained against shortening and the ePTFE is exposed to a temperature above the crystalline melt temperature of the PTFE resin for a period of time to sinter the PTFE and amorphously lock the node-fibril microstructure and stabilize the porosity of the ePTFE tubular structure.

FIG. 1 depicts a radially expandable ePTFE tubular member 10 in accordance with the present invention. The inventive ePTFE tubular member 10 has an inner diameter d and is shown with a portion of its outer surface cut away and microscopically enlarged to illustrate the ePTFE microstructure 12. The ePTFE microstructure consists of a plurality of nodes 14 interconnected by a plurality of fibrils 16. The plurality of fibrils 16 emanate from and converge to the plurality of nodes 14 spanning the internodal distance a. The plurality of nodes 14 are each substantially solid, have a node length b which is generally perpendicular to the longitudinal axis of the ePTFE tubular member 10 and parallel with the transverse axis of the ePTFE tubular member 10.

Figure 2:
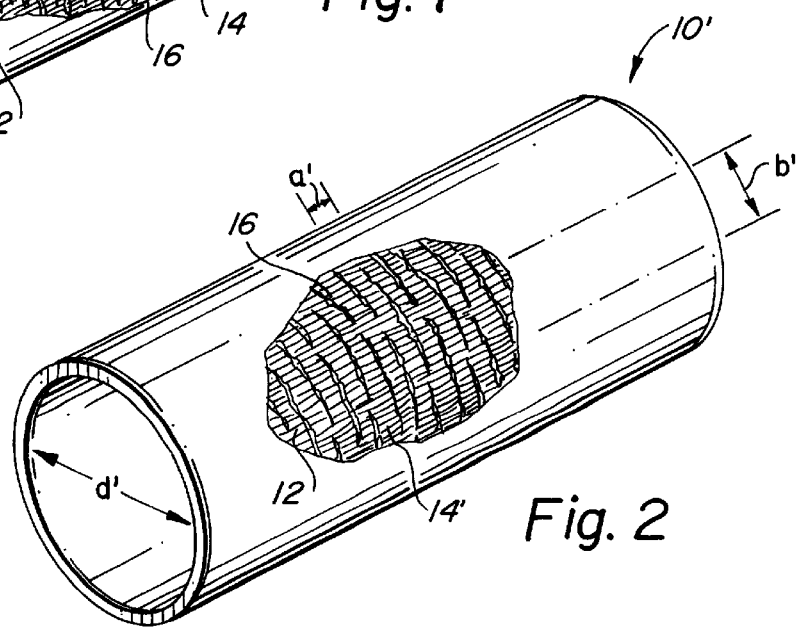
FIG. 2 is a perspective, partial cut-away view of the inventive radially expandable ePTFE graft in its post-expansion diameter diagrammatically illustrating the post-radial expansion microstructure of the ePTFE material.

FIG. 2 depicts the same tube depicted in FIG. 1 which has been radially expanded to a larger diameter d'. Radial expansion is accomplished, for example, by introducing a balloon catheter into the lumen of the ePTFE tubular member 10, introducing a pressurized fluid into the balloon catheter, thereby causing the catheter balloon to expand and exert a positive pressure directed radially outward from the lumen of ePTFE tubular member 10, which, in turn, radially deforms ePTFE tubular member 10 to a larger diameter. Radial deformation of the ePTFE tubular member 10 is mediated by elongation of the plurality of nodes 14 to an elongated node length b' in the region of the ePTFE tubular member 10 where the positive pressure is exerted by the catheter balloon. As illustrated in FIG. 2 the entire ePTFE tubular member 10 is radially deformed to the larger diameter d'. One notable physical feature of the present invention is the elongation of the plurality of nodes 14 along their longitudinal axis while the post-expansion average internodal distances a' remains substantially the same as the internodal distance a of the non-radially deformed ePTFE tubular member 10.

It will be understood, by those skilled in the art, that the radially deformable ePTFE tubular member 10 of the present invention is particularly well suited for use as a covering or liner for an endoluminal stent. Endoluminal stents are generally of three types. Balloon expandable endoluminal stents require the application of a positive pressure to the stent to radially deform the stent beyond the elastic limit of the material used to make the stent. Balloon expandable stents are represented in the art by PALMAZ patents. Self-expanding endoluminal stents are made with a configuration which takes advantage of the elastic properties of the stent material and are radially constrained by a restraining sheath during endoluminal delivery and undergo elastic expansion to their unconstrained diameter when the restraining sheath is removed. Self expanding stents are represented in the art by the GIANTURCO or WALLSTENT. Finally, shape memory stents are made of shape memory materials, such as nickel-titanium alloys known as NITINOL, which expand upon exposure to a temperature differential, e.g., expands at body temperature. Any of the foregoing endoluminal stent types may be covered, lined or encapsulated by the inventive radially deformable ePTFE tubular member 10 and radially expanded either in vivo or in vitro.

Figure 3A:
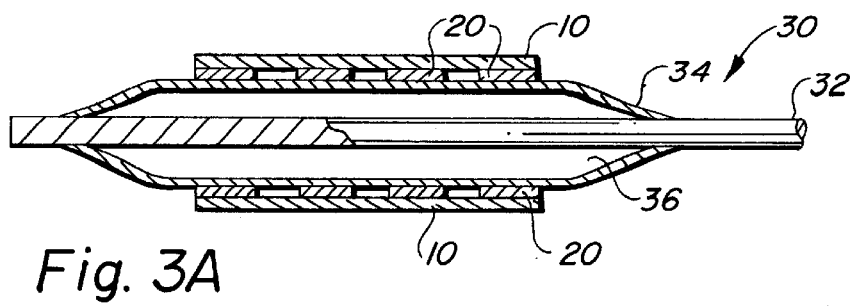
FIG. 3A is a longitudinal cross-sectional view depicting the inventive radially expandable ePTFE graft covering a radially expandable endoluminal stent, the assembly being depicted mounted on a balloon catheter in its radially unexpanded condition.
Figure 3B:
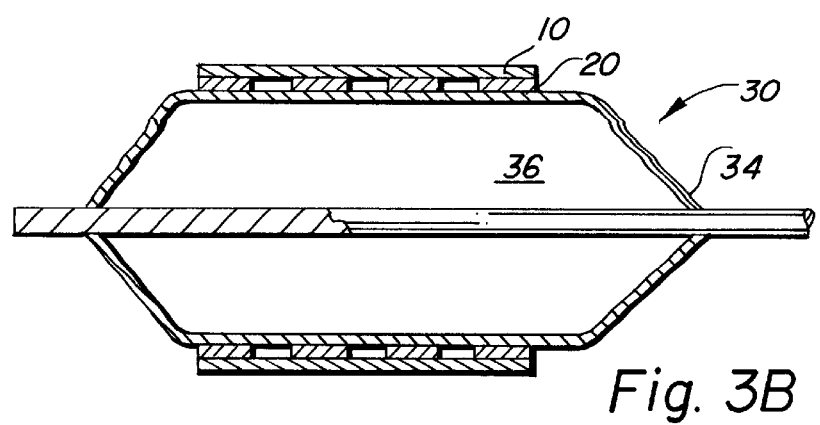
FIG. 3B is the longitudinal cross-sectional view depicting the inventive radially expandable ePTFE graft covering a radially expandable endoluminal stent, the assembly being depicted mounted on a balloon catheter in its radially expanded condition.

FIGS. 3A and 3B illustrate the inventive radially expandable ePTFE material 10 encapsulating an endoluminal stent 20, as more fully described in commonly assigned, co-pending application published as PCT International Application WO96/28115, published Sep. 19, 1996, claiming priority from co-pending U.S. patent applications Ser. Nos. 08/401,871 filed Mar. 10, 1995 and 08/508,033 filed Jul. 27, 1995, which is hereby incorporated by reference thereto. FIG. 3A illustrates an encapsulated stent graft 20 in its pre-radially expanded diameter, while FIG. 3B illustrates an encapsulated stent graft 30 in its post-radially expanded diameter. The encapsulated stent graft assembly, consisting generally of radially expandable ePTFE material 10 and endoluminal stent 20, are concentrically positioned about a catheter balloon 34 mounted on the distal end of a balloon catheter 32. The catheter balloon 34 defines an inflation chamber 36 therein which receives a pressurized inflation fluid (not shown) from a external source (not shown). When the pressurized inflation fluid is introduced into the inflation chamber 36, an outwardly directed radial force is exerted substantially uniformly against the luminal surface of the stent graft assembly, thereby urging the stent-graft assembly from its smaller delivery diameter to a larger final diameter depicted in FIG. 3B. During dilatation of the catheter balloon 34, the rePTFE material 10 undergoes a substantially plastic deformation transverse to the longitudinal axis of the tubular ePTFE material 10. The positive pressure exerted by the pressurized inflation fluid exerts a radially outward positive pressure to the luminal surface of the radially deformable ePTFE which is oriented substantially parallel to the longitudinal axis of the plurality of nodes in the ePTFE microstructure. The plurality of nodes in the ePTFE microstructure undergo substantially plastic deformation and elongate along their longitudinal axis, thus causing the radial deformation of the ePTFE tubular material 10.

FIGS. 5A–5D are scanning electron micrographs taken at 200× and 500× magnification of the inner and outer surfaces of a standard ePTFE vascular graft (Lot 34391, IMPRA, Inc., Tempe, Ariz.). It will be noted that the node-fibril microstructure of the ePTFE is characterized by irregular node patterns and fibrils which are substantially cylindrical as reflected by the substantially parallel surfaces along the longitudinal axis of each fibril.

Figure 10A:
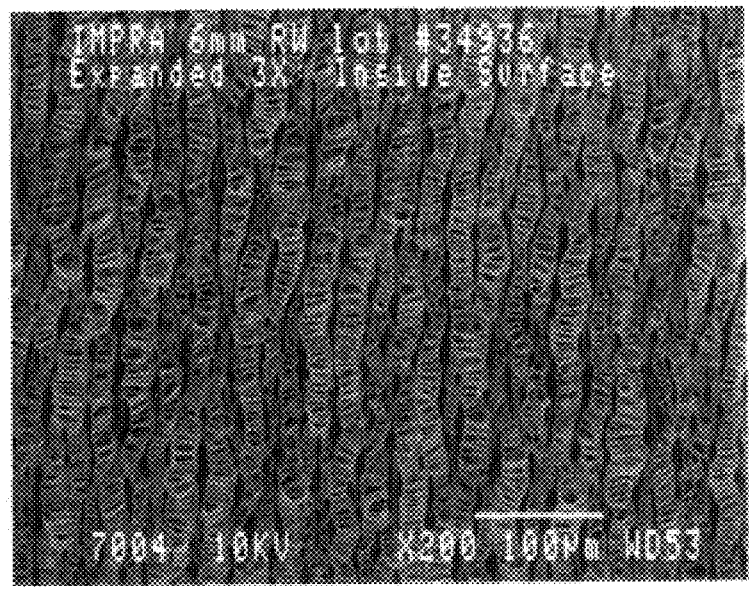
FIG. 10A is a scanning electron photomicrograph of the inner surface of a 6 mm ID conventional expanded ePTFE vascular graft radially expanded 3× at 200× magnification.
Figure 10B:
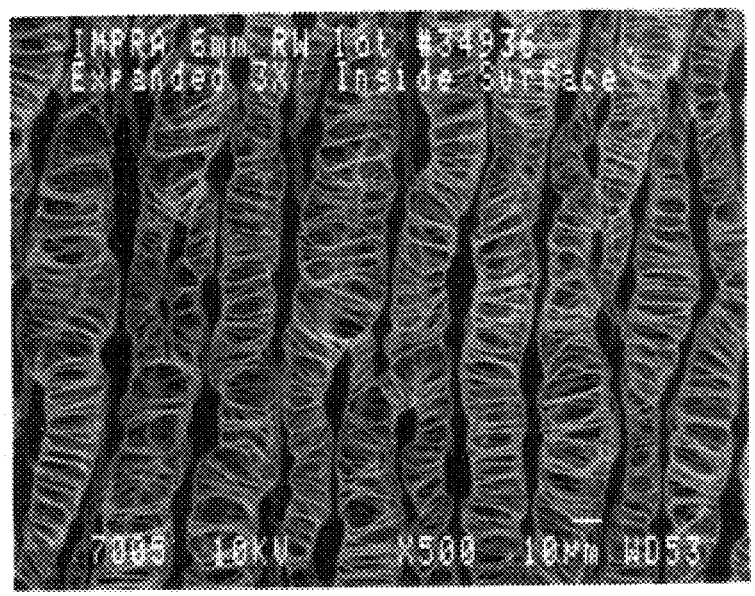
FIG. 10B is a scanning electron photomicrograph of the inner surface of the 6 mm ID conventional expanded ePTFE vascular graft of FIG. 10A taken at 500× magnification.
Figure 10C:
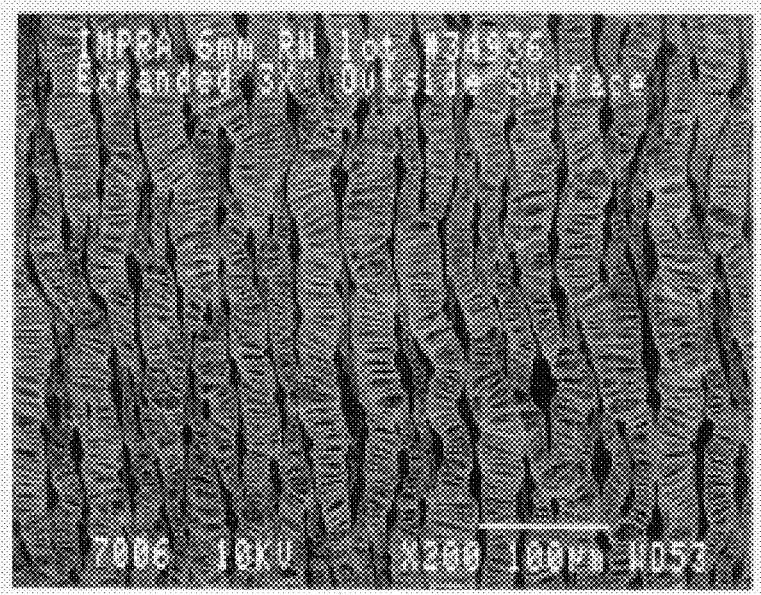
FIG. 10C is a scanning electron photomicrograph of the outer surface of the 6 mm ID conventional expanded ePTFE vascular graft of FIG. 10A at 200× magnification.
Figure 10D:
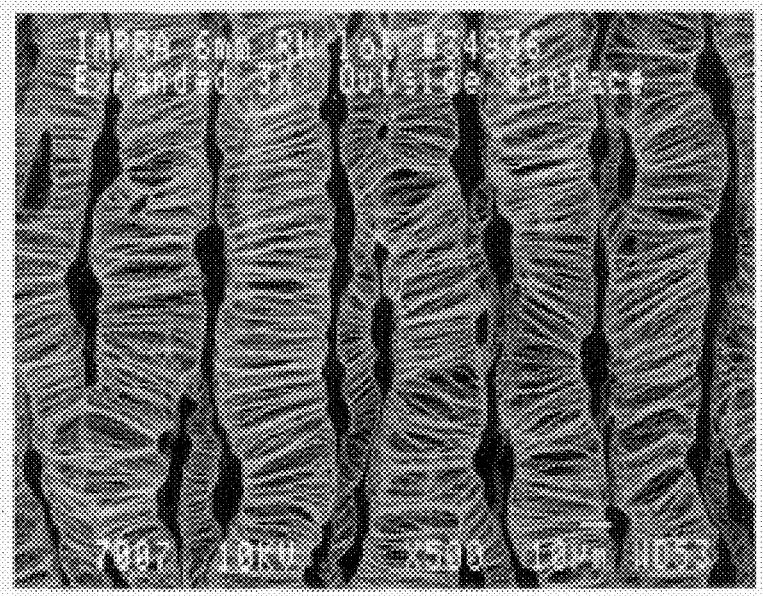
FIG. 10D is a scanning electron photomicrograph of the outer surface of the 6 mm ID conventional expanded ePTFE vascular graft of FIG. 10A taken at 500× magnification.
Figure 11A:
FIG. 11A is a scanning electron photomicrograph of the inner surface of a 6 mm ID conventional expanded ePTFE vascular graft radially expanded 4× at 200× magnification.
Figure 11B:
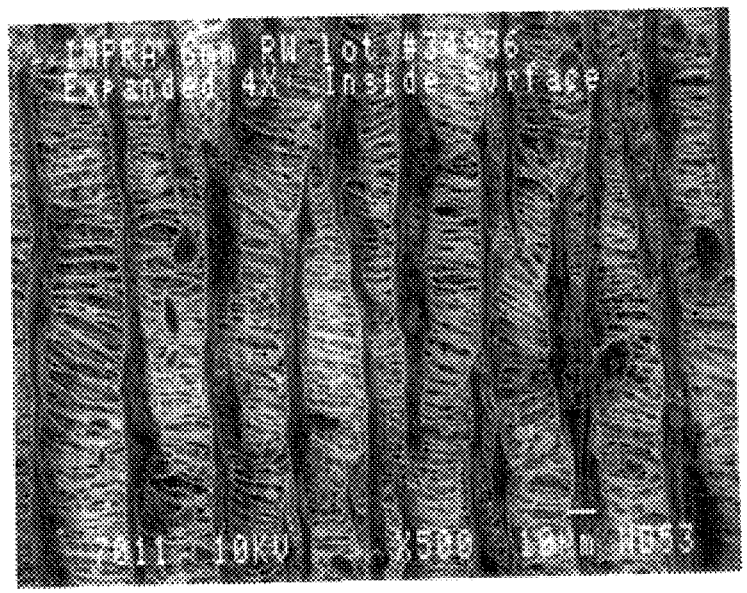
FIG. 11B is a scanning electron photomicrograph of the inner surface of the 6 mm ID conventional expanded ePTFE vascular graft of FIG. 11A taken at 500× magnification.
Figure 11C:
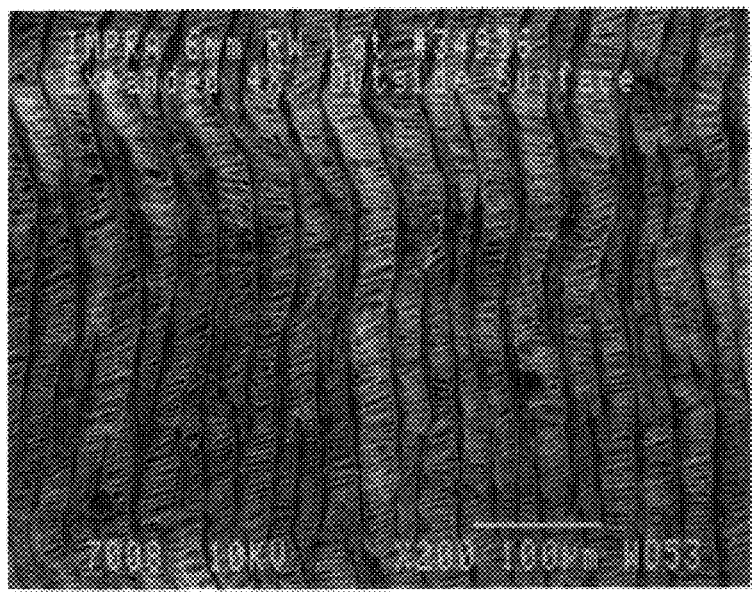
FIG. 11C is a scanning electron photomicrograph of the outer surface of the 6 mm ID conventional expanded ePTFE vascular graft of FIG. 11A at 200× magnification.
Figure 11D:
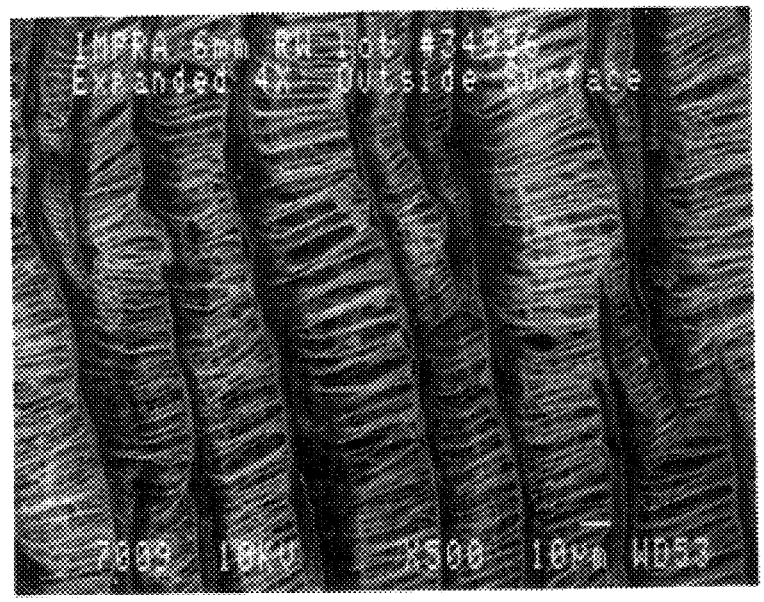
FIG. 11D is a scanning electron photomicrograph of the outer surface of the 6 mm ID conventional expanded ePTFE vascular graft of FIG. 11A taken at 500× magnification.
Figure 12A:
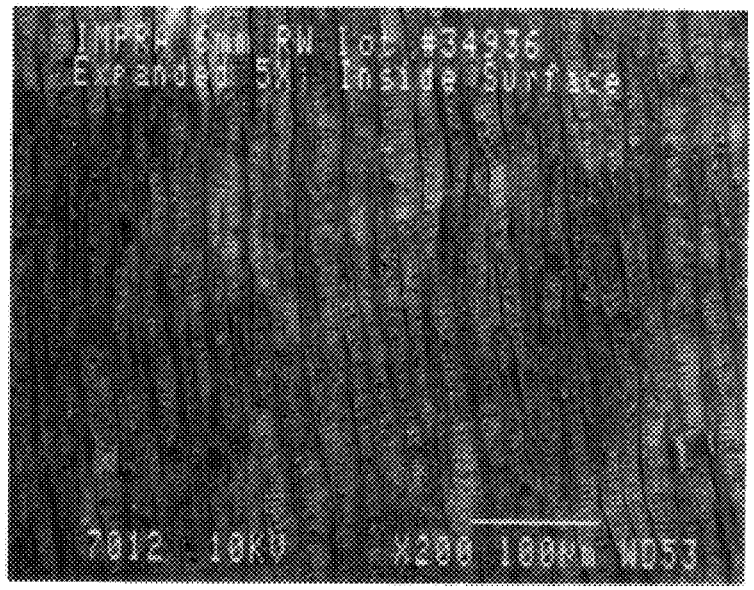
FIG. 12A is a scanning electron photomicrograph of the inner surface of a 6 mm ID conventional expanded ePTFE vascular graft radially expanded 5× at 200× magnification.
Figure 12B:
FIG. 12B is a scanning electron photomicrograph of the inner surface of the 6 mm ID conventional expanded ePTFE vascular graft of FIG. 12A taken at 500× magnification.
Figure 12C:
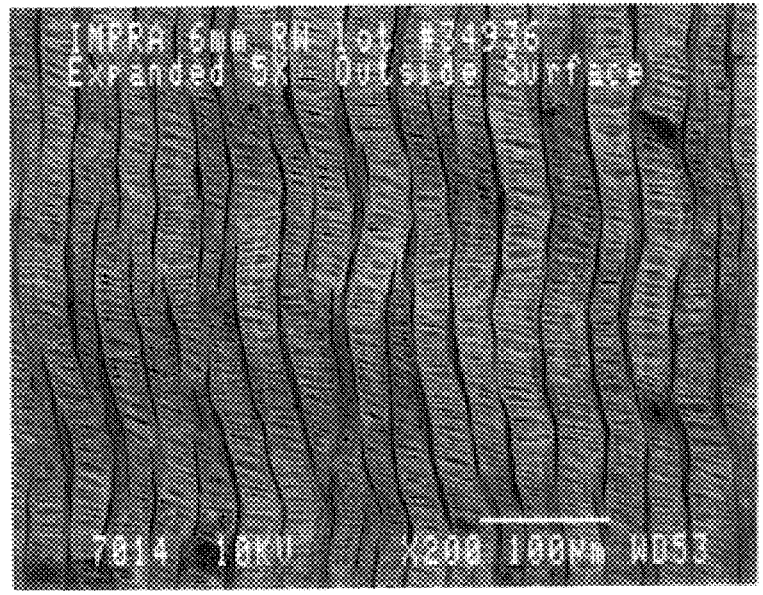
FIG. 12C is a scanning electron photomicrograph of the outer surface of the 6 mm ID conventional expanded ePTFE vascular graft of FIG. 12A at 200× magnification.
Figure 12D:
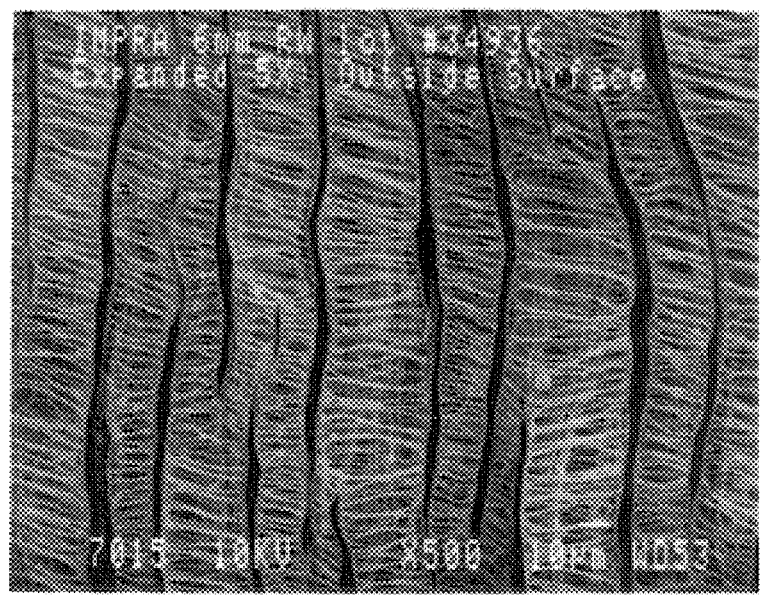
FIG. 12D is a scanning electron photomicrograph of the outer surface of the 6 mm ID conventional expanded ePTFE vascular graft of FIG. 12A taken at 500× magnification.
Figure 13A:
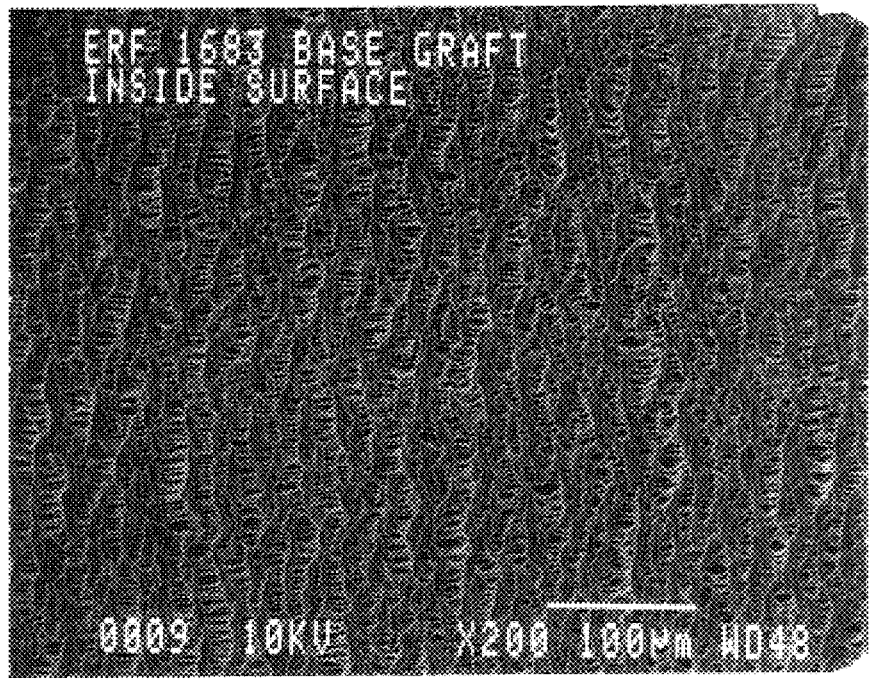
FIG. 13A is a scanning electron photomicrograph of the inner surface of a non-radially expanded 3 mm ID inventive rePTFE endoluminal graft ERF 1683 at 200× magnification.
Figure 13B:
FIG. 13B is a scanning electron photomicrograph of the inner surface of the non-radially expanded 3 mm ID inventive rePTFE endoluminal graft of FIG. 13A taken at 500× magnification.
Figure 13C:
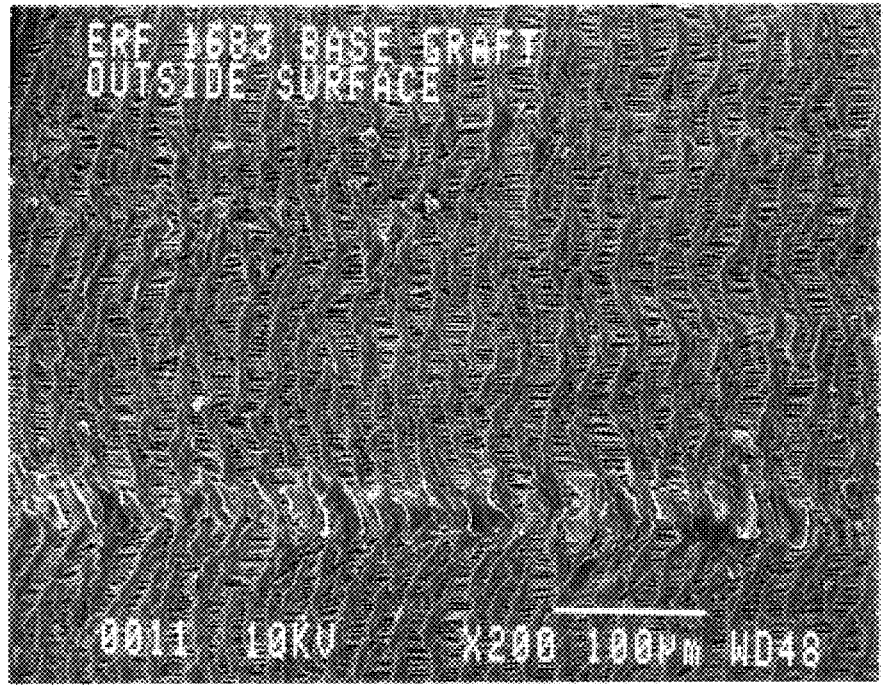
FIG. 13C is a scanning electron photomicrograph of the outer surface of the non-radially expanded 3 mm ID inventive rePTFE endoluminal graft of FIG. 13A at 200× magnification.
Figure 13D:
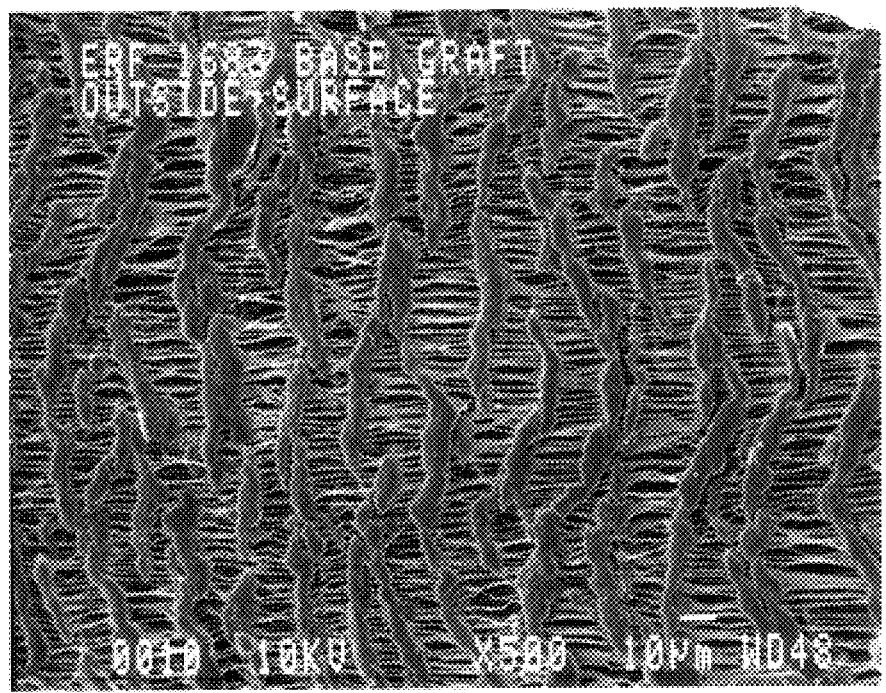
FIG. 13D is a scanning electron photomicrograph of the outer surface of the non-radially expanded 3 mm ID inventive rePTFE endoluminal graft of FIG. 13A taken at 500× magnification.
Figure 14A:
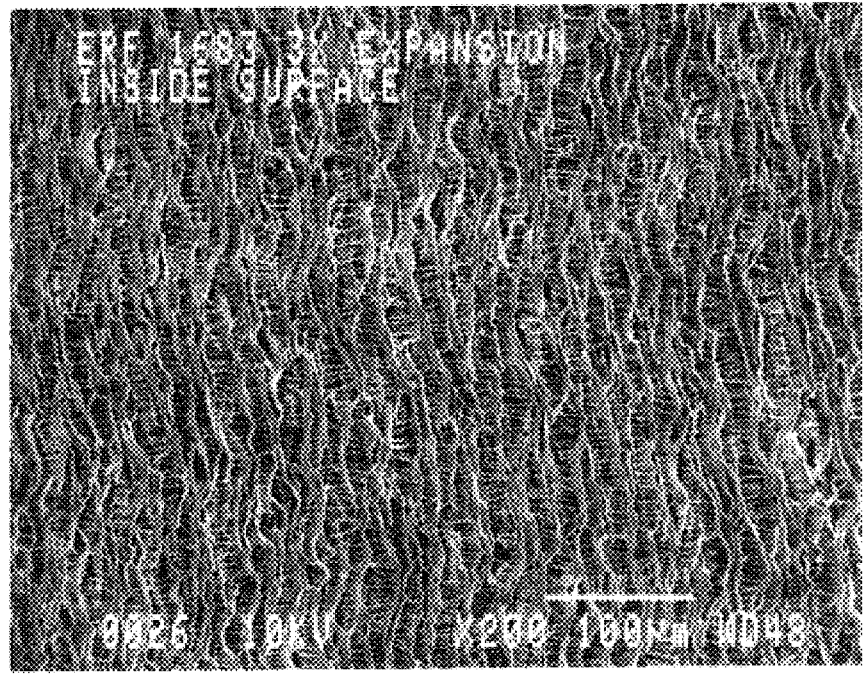
FIG. 14A is a scanning electron photomicrograph of the inner surface of an inventive rePTFE endoluminal graft ERF 1683 radially expanded 3× at 200× magnification.
Figure 14B:
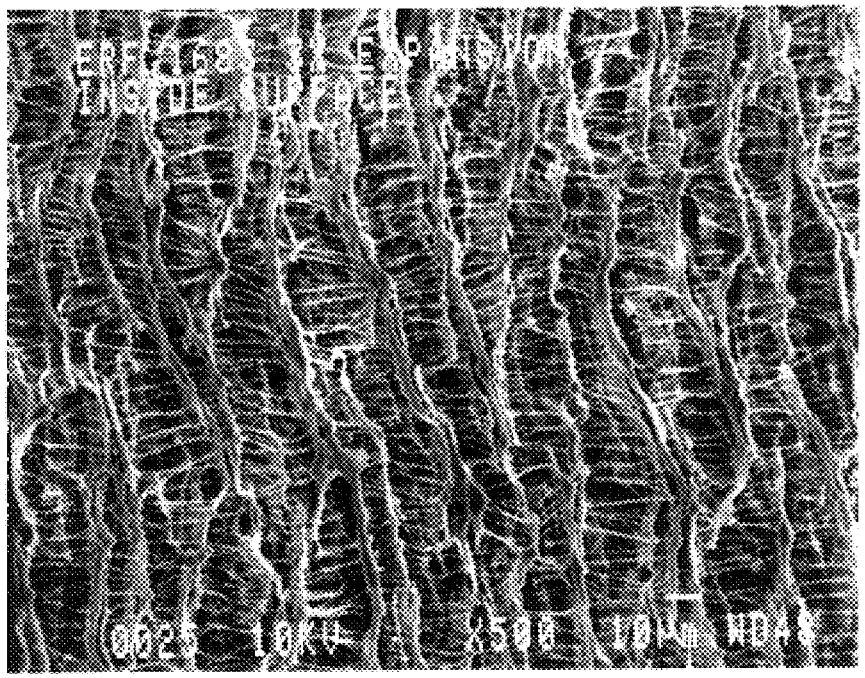
FIG. 14B is a scanning electron photomicrograph of the inner surface of the inventive rePTFE endoluminal graft ERF 1683 of FIG. 14A taken at 500× magnification.
Figure 14C:
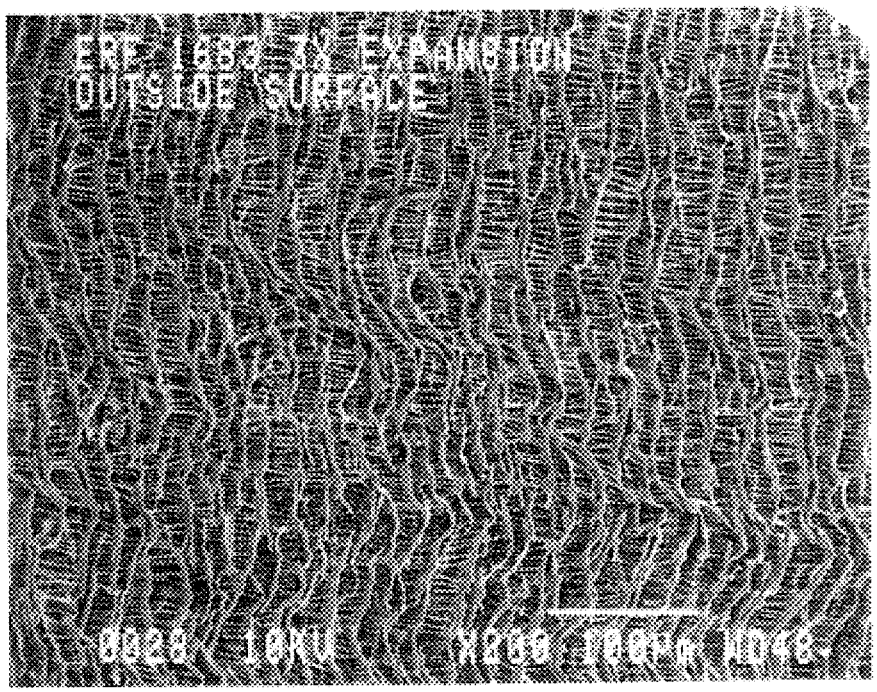
FIG. 14C is a scanning electron photomicrograph of the outer surface of the inventive rePTFE endoluminal graft ERF 1683 of FIG. 14A at 200× magnification.
Figure 14D:
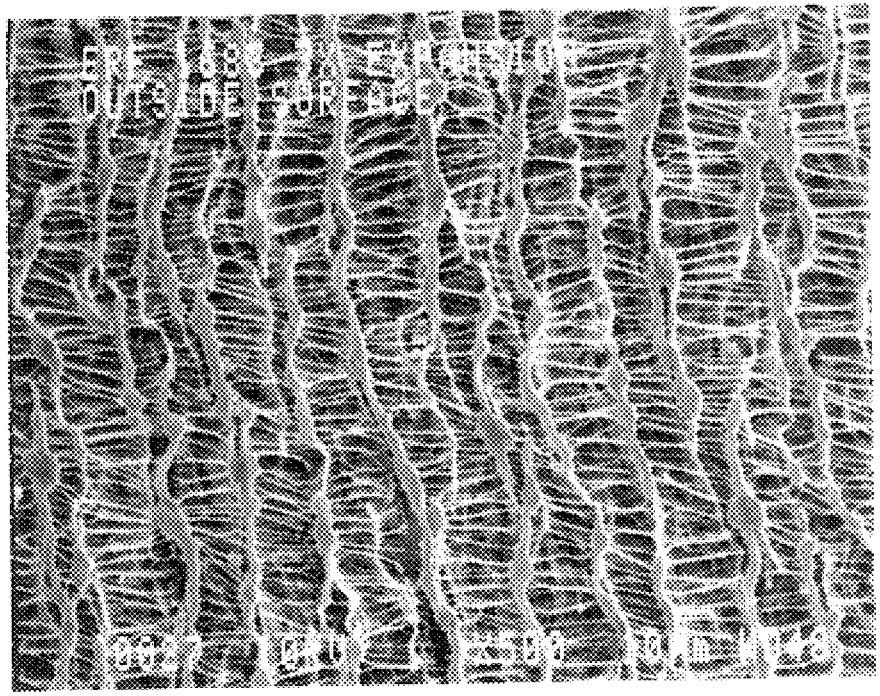
FIG. 14D is a scanning electron photomicrograph of the outer surface of the inventive rePTFE endoluminal graft ERF 1683 of FIG. 14A taken at 500× magnification.
Figure 15A:
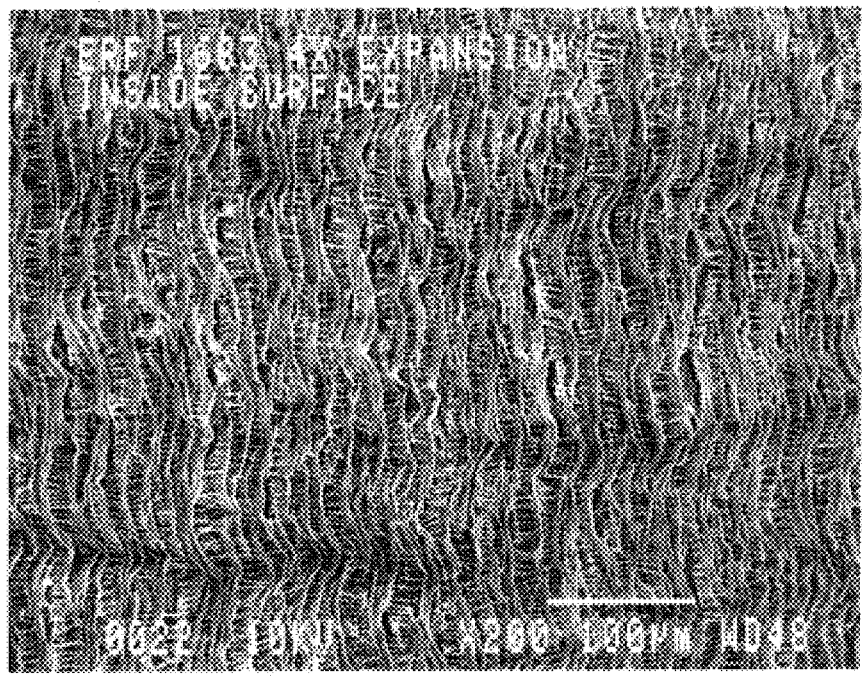
FIG. 15A is a scanning electron photomicrograph of the inner surface of an inventive rePTFE endoluminal graft ERF 1683 radially expanded 4× at 200× magnification.
Figure 15B:
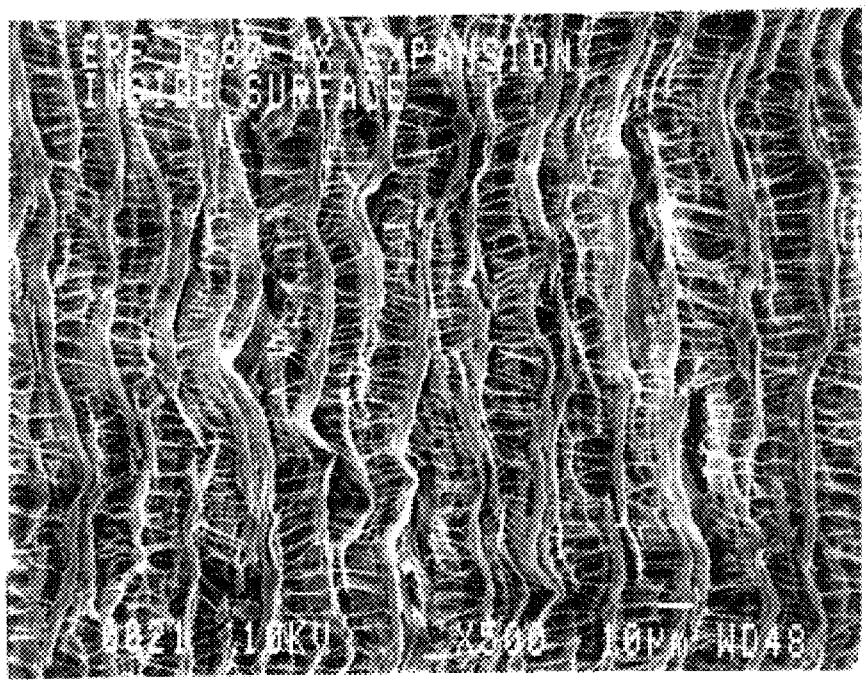
FIG. 15B is a scanning electron photomicrograph of the inner surface of the inventive rePTFE endoluminal graft ERF 1683 of FIG. 15A taken at 500× magnification.
Figure 15C:
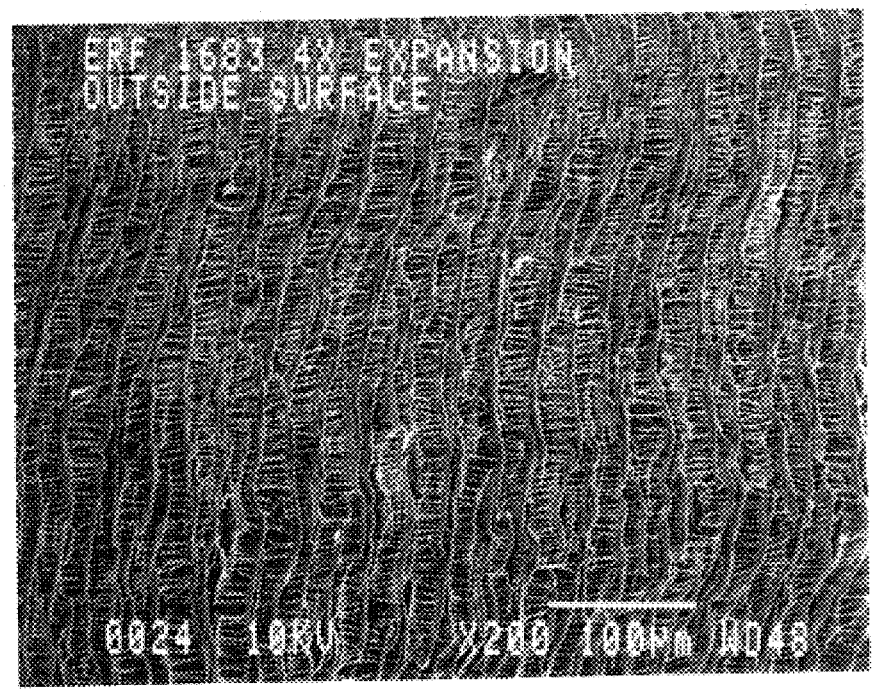
FIG. 15C is a scanning electron photomicrograph of the outer surface of the inventive rePTFE endoluminal graft ERF 1683 of FIG. 15A at 200× magnification.
Figure 15D:
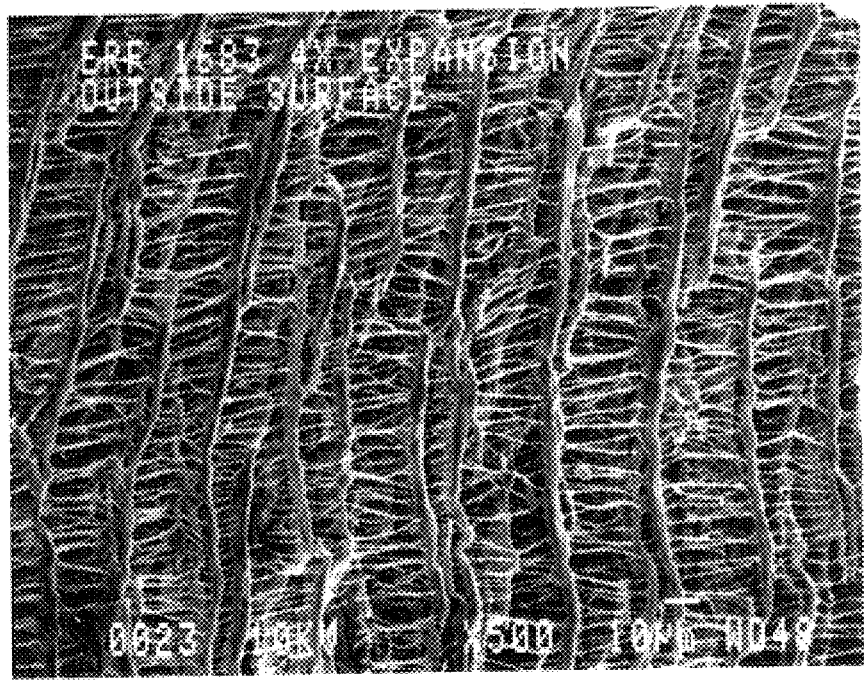
FIG. 15D is a scanning electron photomicrograph of the outer surface of the inventive rePTFE endoluminal graft ERF 1683 of FIG. 15A taken at 500× magnification.
Figure 16A:
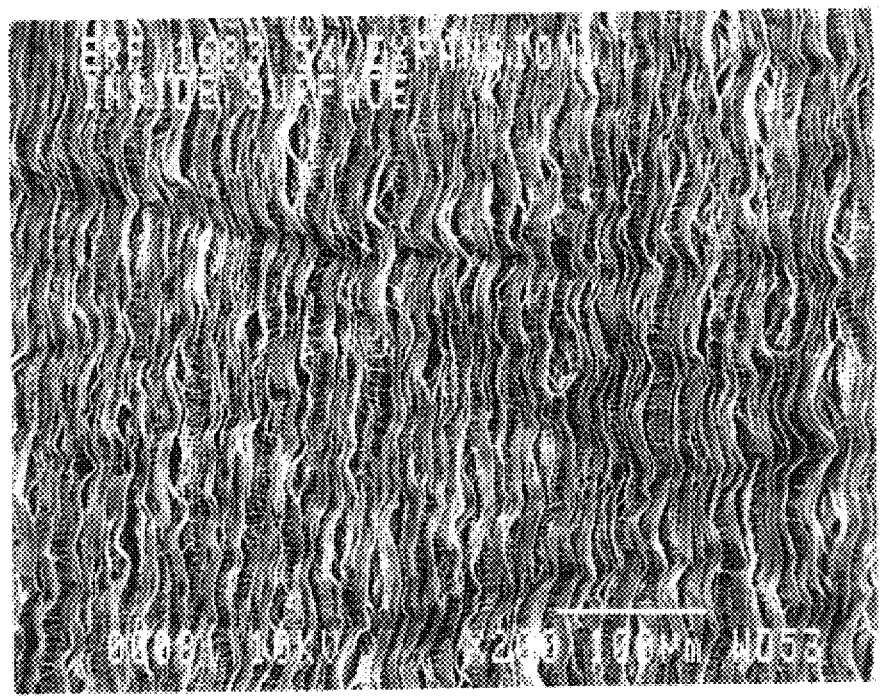
FIG. 16A is a scanning electron photomicrograph of the inner surface of an inventive rePTFE endoluminal graft ERF 1683 radially expanded 5× at 200× magnification.
Figure 16B:
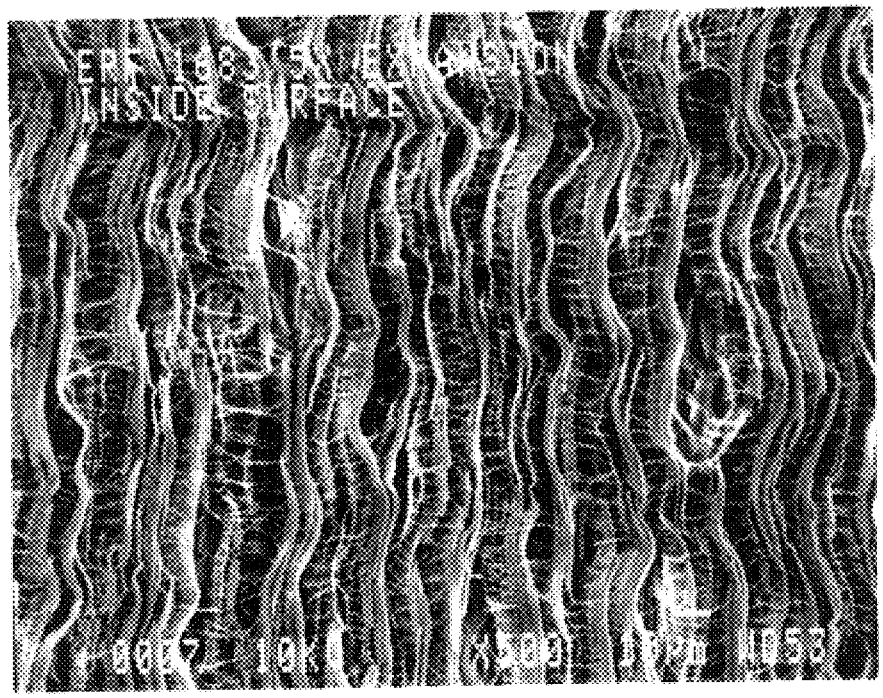
FIG. 16B is a scanning electron photomicrograph of the inner surface of the inventive rePTFE endoluminal graft ERF 1683 of FIG. 16A taken at 500× magnification.
Figure 16C:
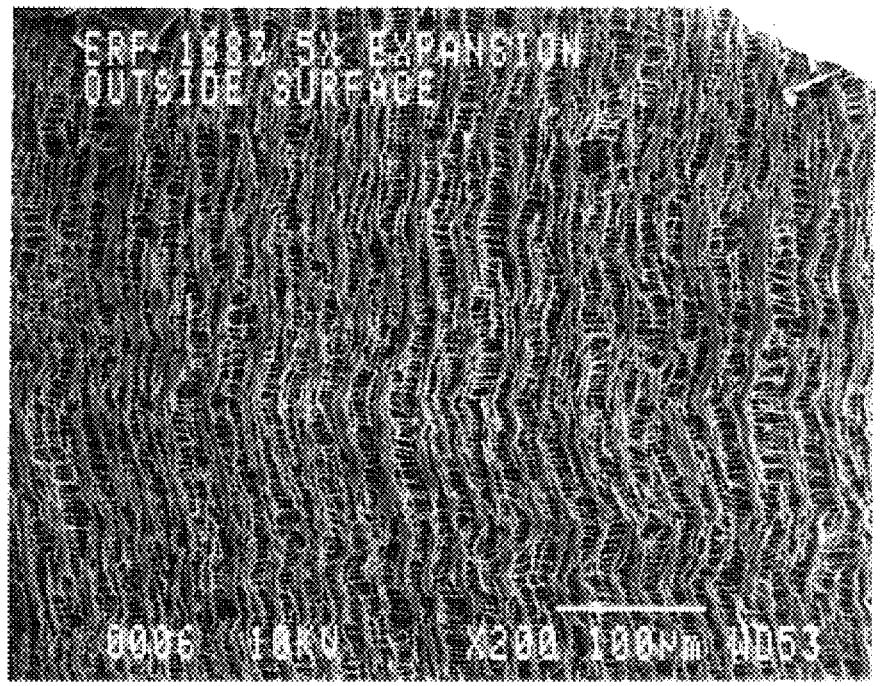
FIG. 16C is a scanning electron photomicrograph of the outer surface of the inventive rePTFE endoluminal graft ERF 1683 of FIG. 16A at 200× magnification.
Figure 16D:
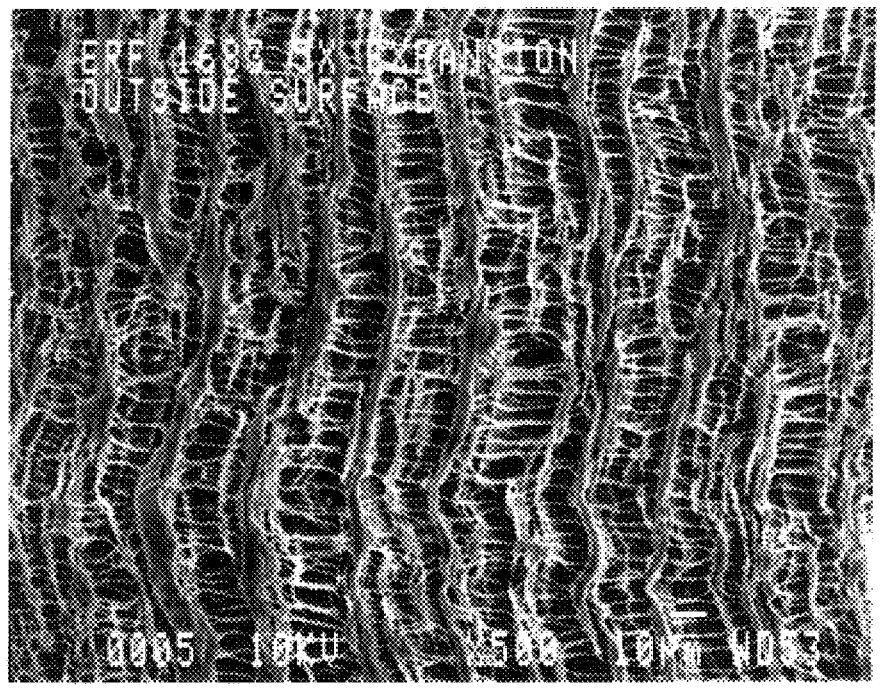
FIG. 16D is a scanning electron photomicrograph of the outer surface of the inventive rePTFE endoluminal graft ERF 1683 of FIG. 16A taken at 500× magnification.
Figure 17A:
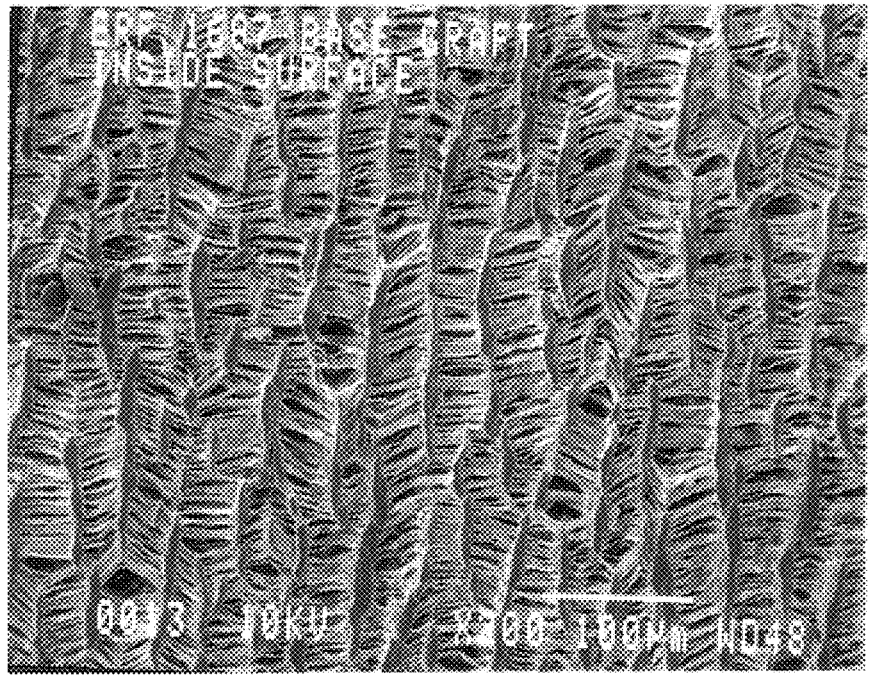
FIG. 17A is a scanning electron photomicrograph of the inner surface of a non-radially expanded 3 mm ID inventive rePTFE endoluminal graft ERF 1687 at 200× magnification.
Figure 17B:
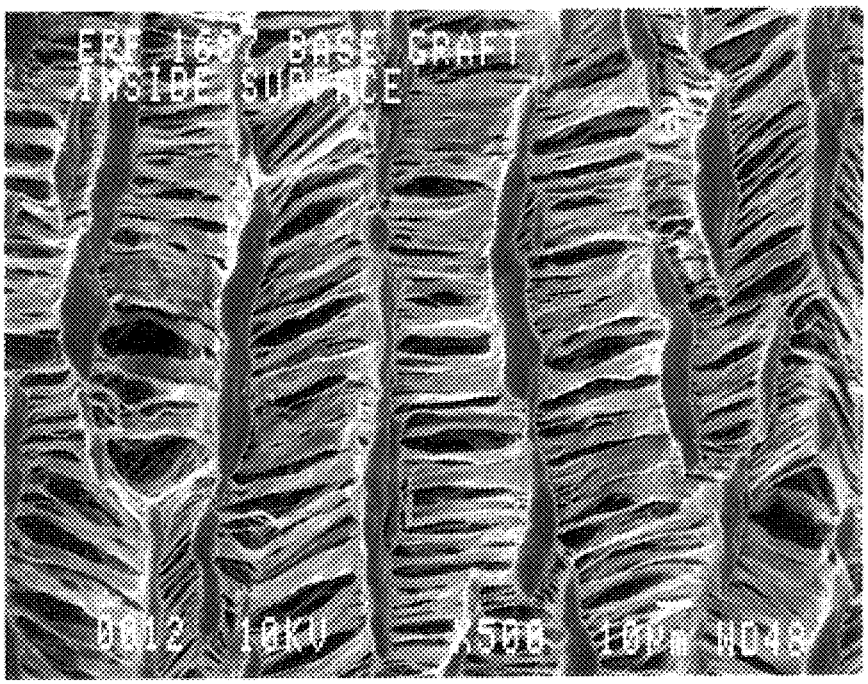
FIG. 17B is a scanning electron photomicrograph of the inner surface of the non-radially expanded 3 mm ID inventive rePTFE endoluminal graft of FIG. 17A taken at 500× magnification.
Figure 17C:
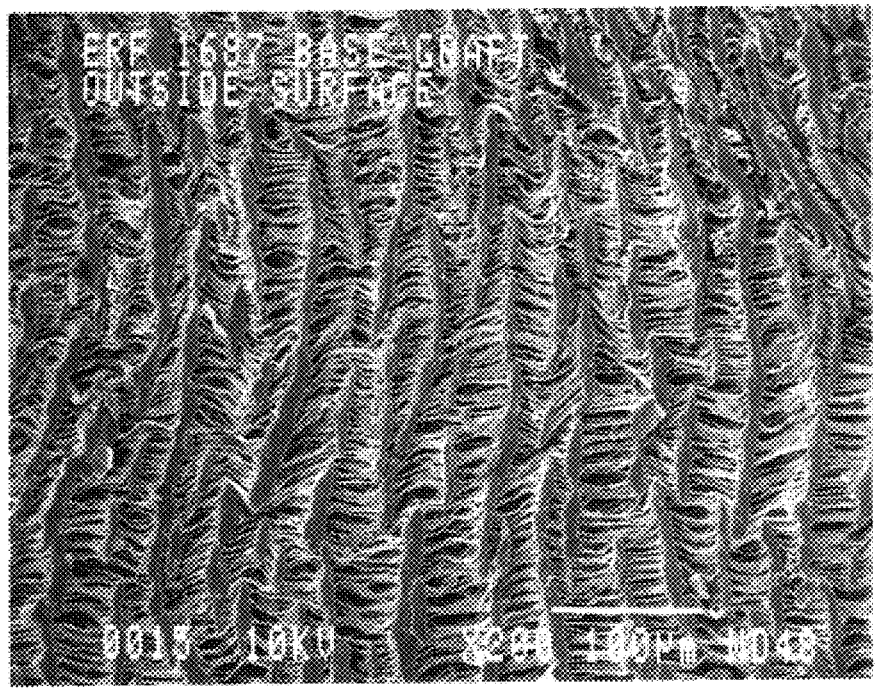
FIG. 17C is a scanning electron photomicrograph of the outer surface of the non-radially expanded 3 mm ID inventive rePTFE endoluminal graft of FIG. 17A at 200× magnification.
Figure 17D:
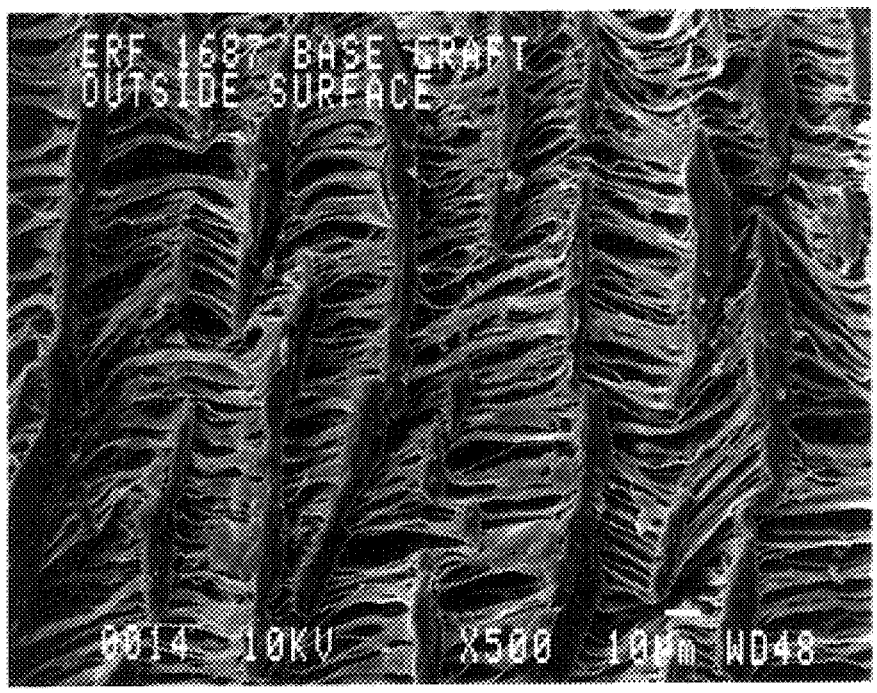
FIG. 17D is a scanning electron photomicrograph of the outer surface of the non-radially expanded 3 mm ID inventive rePTFE endoluminal graft of FIG. 17A taken at 500× magnification.
Figure 18A:
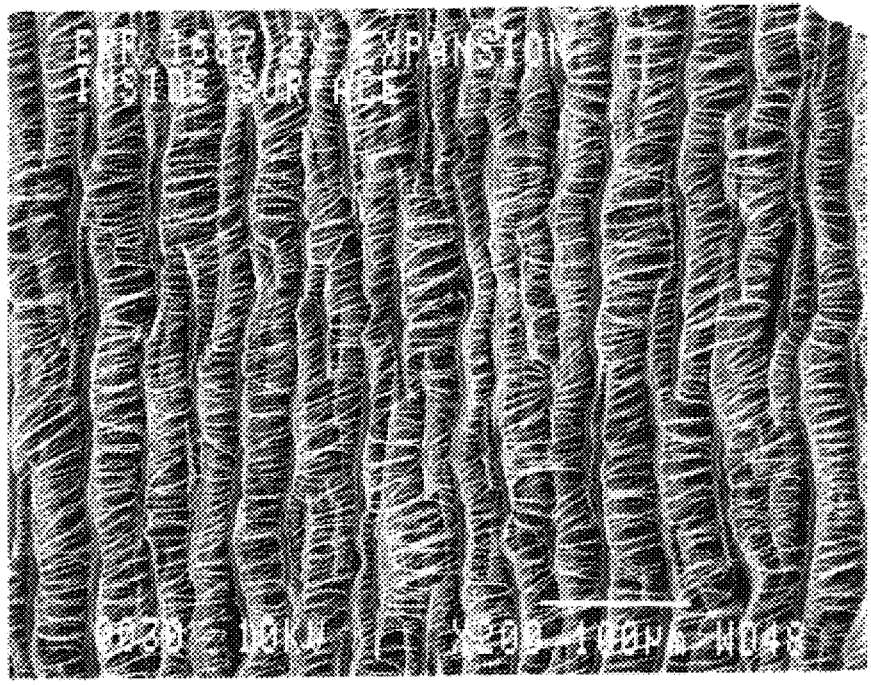
FIG. 18A is a scanning electron photomicrograph of the inner surface of an inventive rePTFE endoluminal graft ERF 1687 radially expanded 3× at 200× magnification.
Figure 18B:
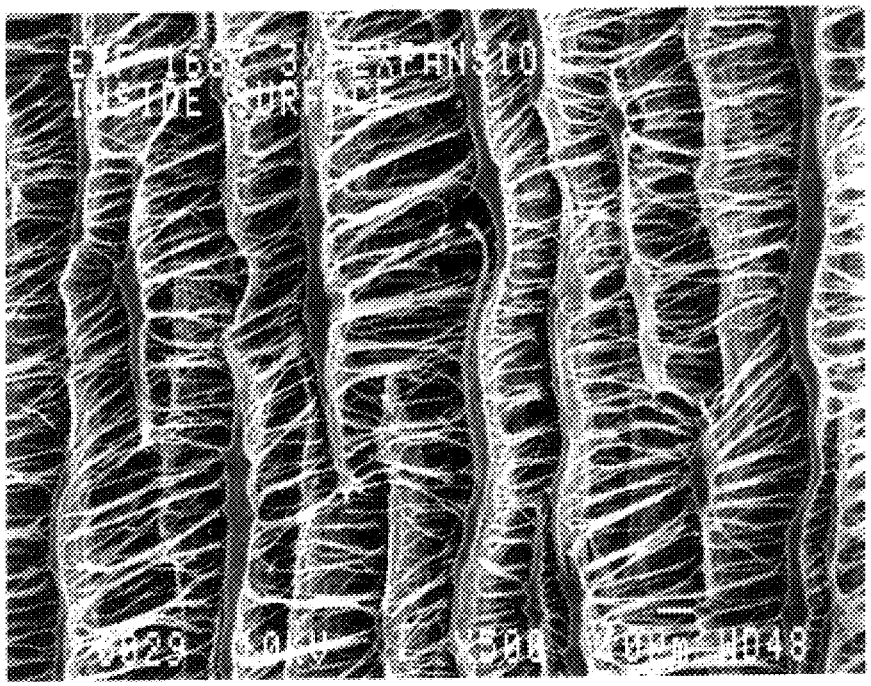
FIG. 18B is a scanning electron photomicrograph of the inner surface of the inventive rePTFE endoluminal graft ERF 1687 of FIG. 18A taken at 500× magnification.
Figure 18C:
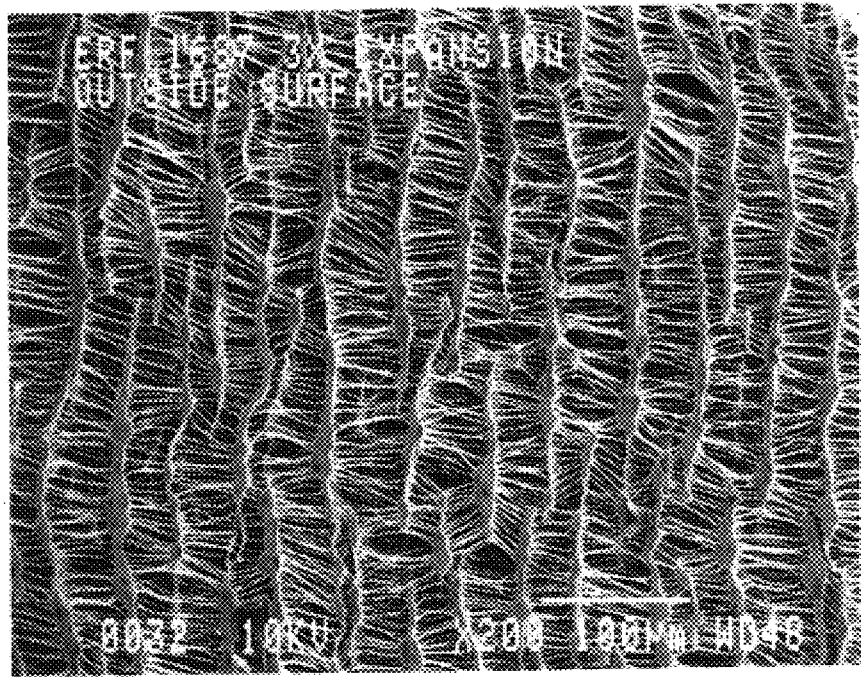
FIG. 18C is a scanning electron photomicrograph of the outer surface of the inventive rePTFE endoluminal graft ERF 1687 of FIG. 18A at 200× magnification.
Figure 18D:
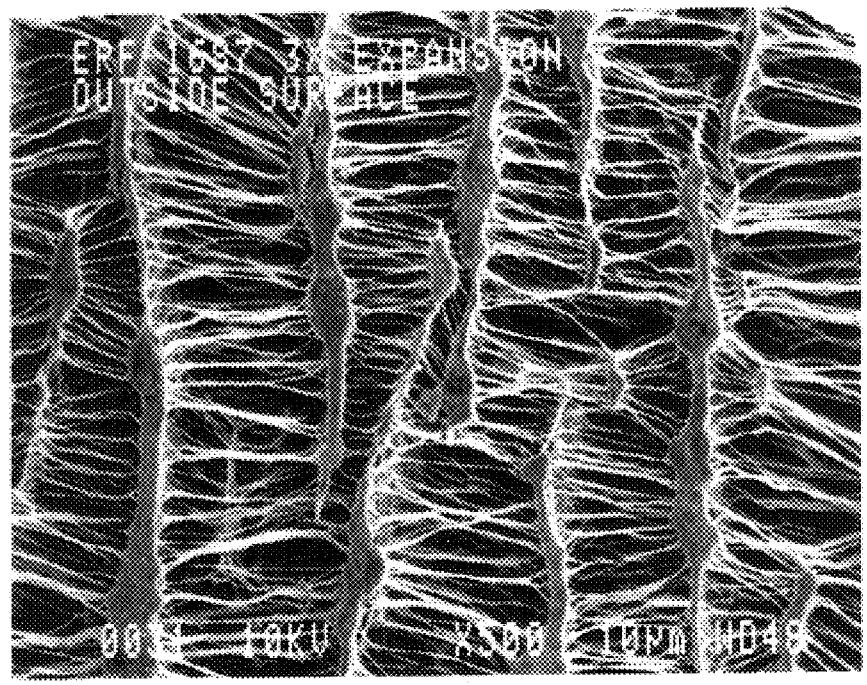
FIG. 18D is a scanning electron photomicrograph of the outer surface of the inventive rePTFE endoluminal graft ERF 1687 of FIG. 18A taken at 500× magnification.
Figure 19A:
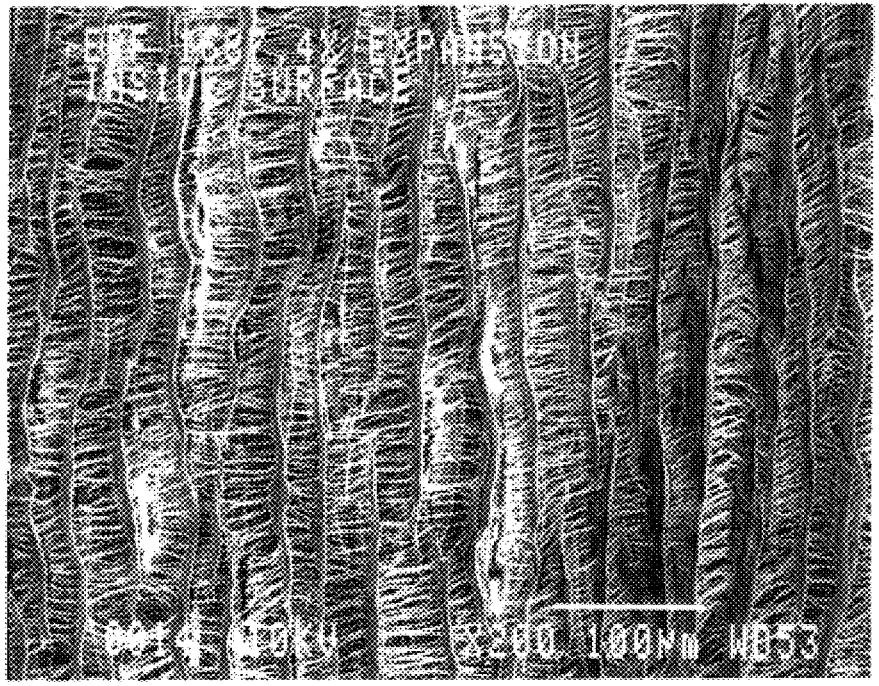
FIG. 19A is a scanning electron photomicrograph of the inner surface of an inventive rePTFE endoluminal graft ERF 1687 radially expanded 4× at 200× magnification.
Figure 19B:
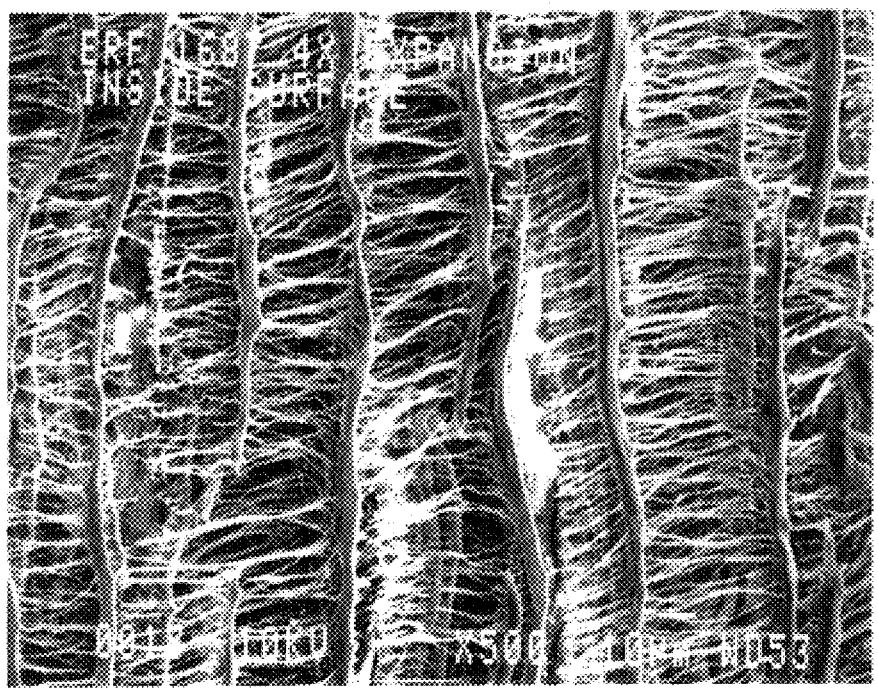
FIG. 19B is a scanning electron photomicrograph of the inner surface of the inventive rePTFE endoluminal graft ERF 1687 of FIG. 19A taken at 500× magnification.
Figure 19C:
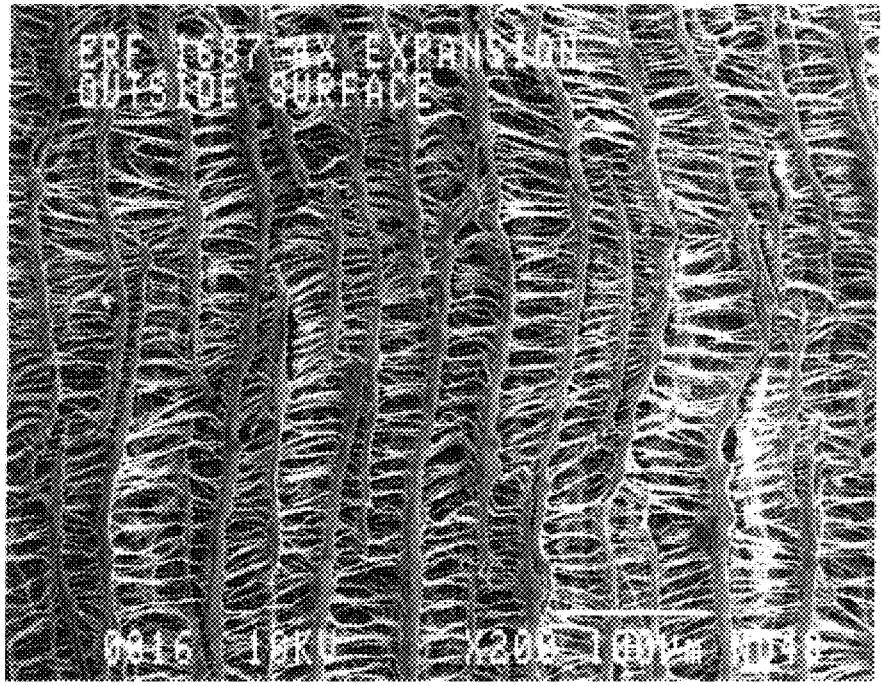
FIG. 19C is a scanning electron photomicrograph of the outer surface of the inventive rePTFE endoluminal graft ERF 1687 of FIG. 19A at 200× magnification.
Figure 19D:
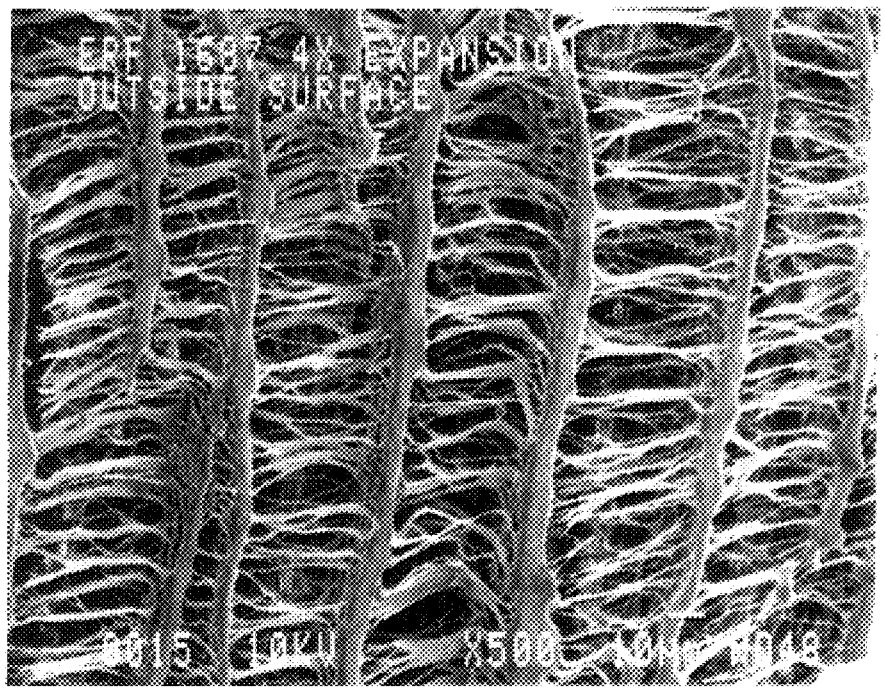
FIG. 19D is a scanning electron photomicrograph of the outer surface of the inventive rePTFE endoluminal graft ERF 1687 of FIG. 19A taken at 500× magnification.
Figure 20A:
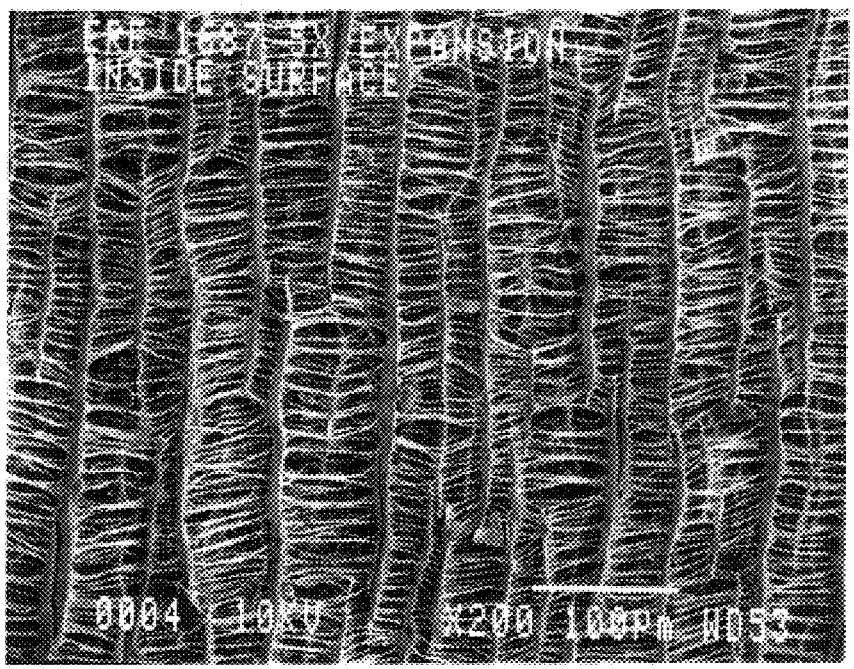
FIG. 20A is a scanning electron photomicrograph of the inner surface of an inventive rePTFE endoluminal graft ERF 1687 radially expanded 5× at 200× magnification.
Figure 20B:
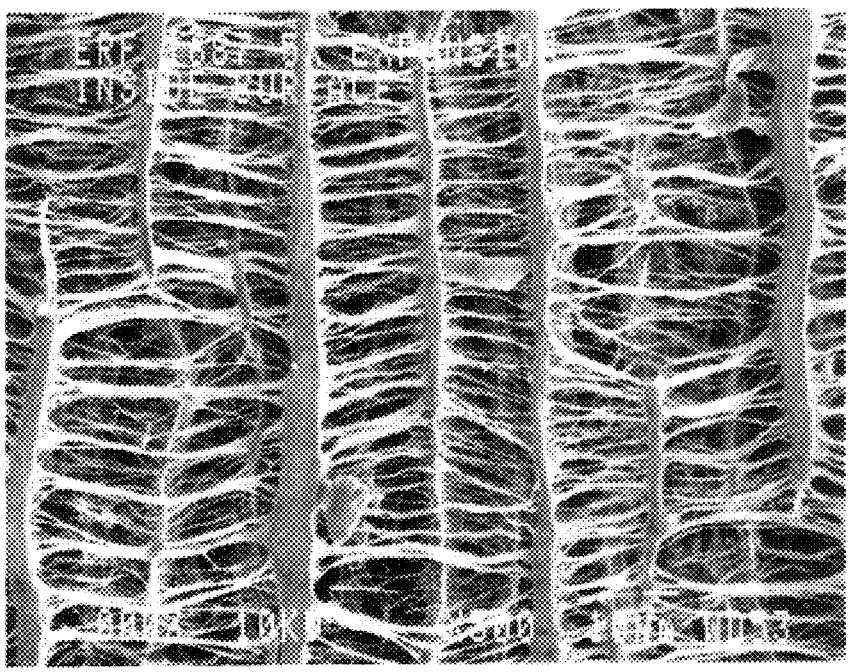
FIG. 20B is a scanning electron photomicrograph of the inner surface of the inventive rePTFE endoluminal graft ERF 1687 of FIG. 20A taken at 500× magnification.
Figure 20C:
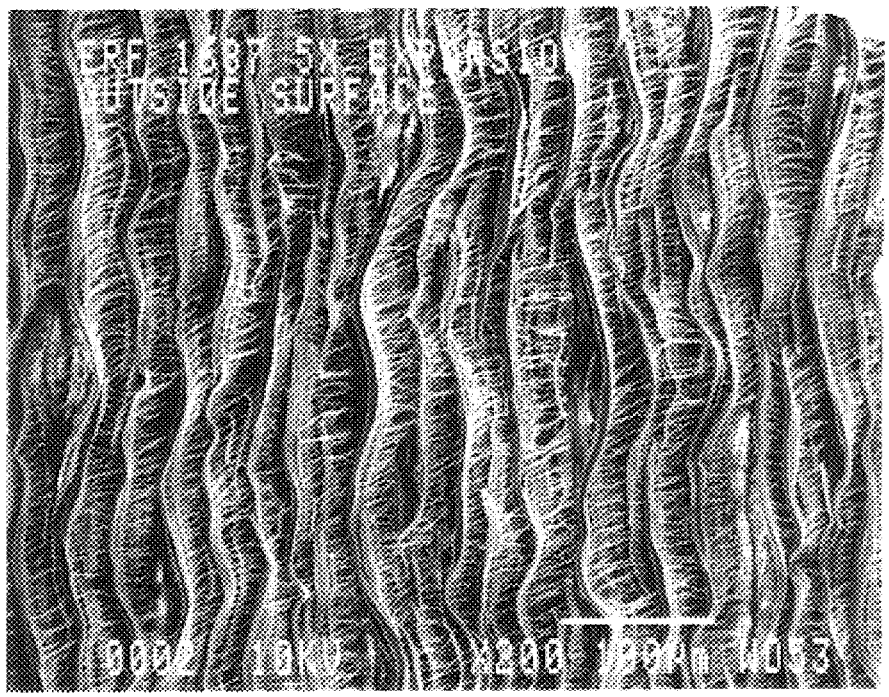
FIG. 20C is a scanning electron photomicrograph of the outer surface of the inventive rePTFE endoluminal graft ERF 1687 of FIG. 20A at 200× magnification.
Figure 20D:
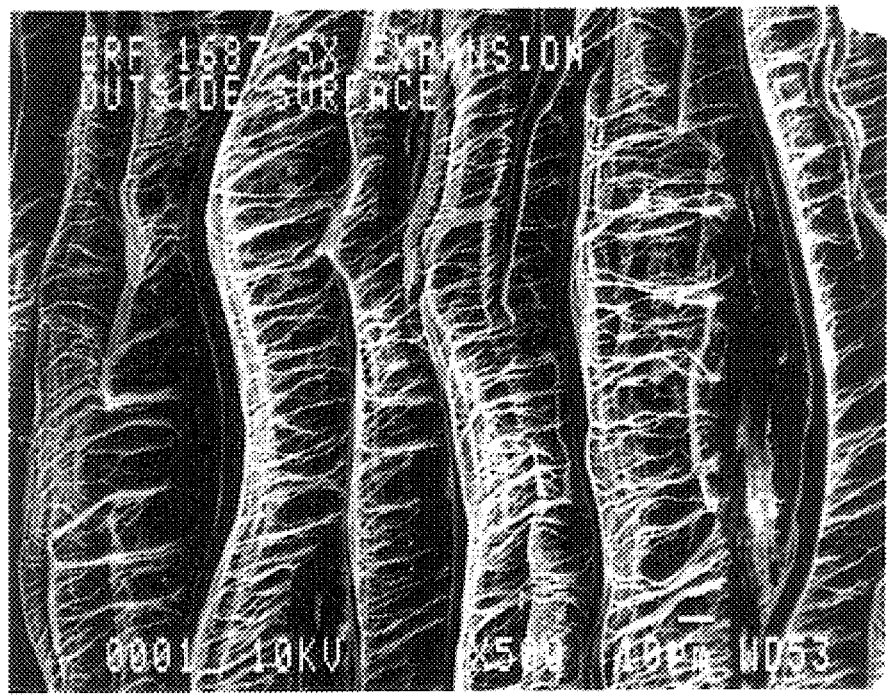
FIG. 20D is a scanning electron photomicrograph of the outer surface of the inventive rePTFE endoluminal graft ERF 1687 of FIG. 20A taken at 500× magnification.
Figure 21A:
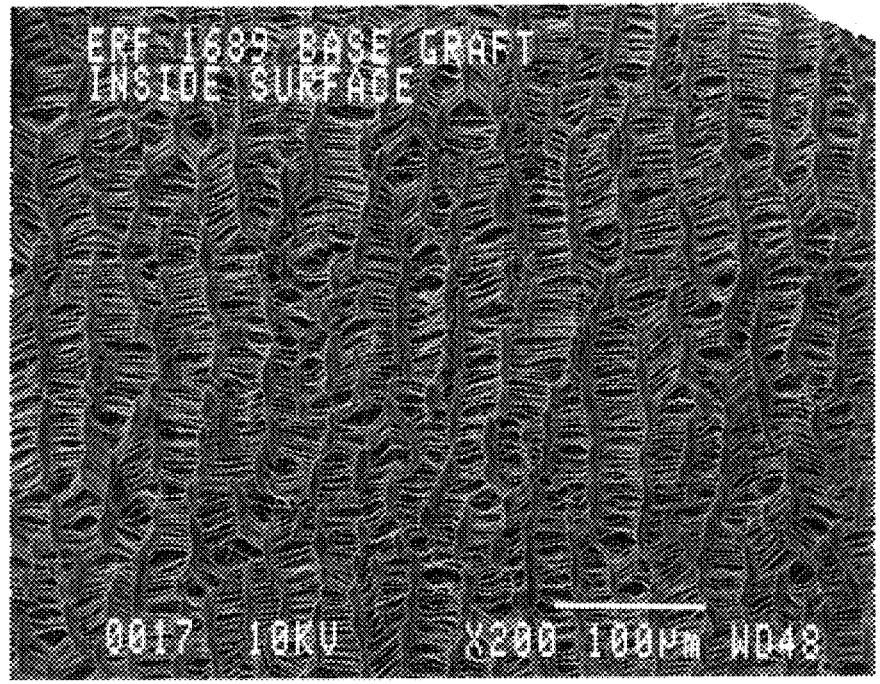
FIG. 21A is a scanning electron photomicrograph of the inner surface of a non-radially expanded 3 mm ID inventive rePTFE endoluminal graft ERF 1689 at 200× magnification.
Figure 21B:
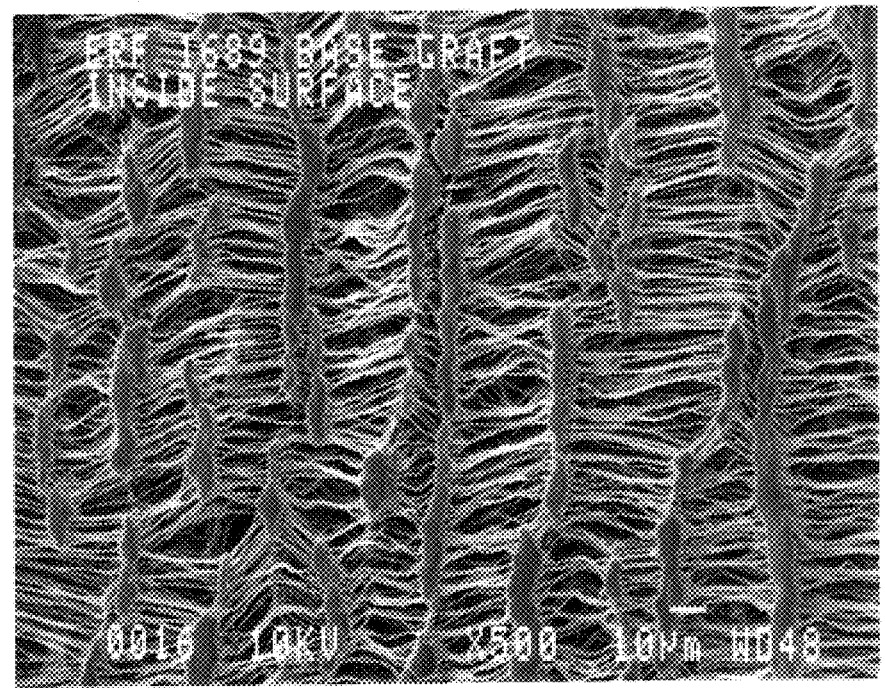
FIG. 21B is a scanning electron photomicrograph of the inner surface of the non-radially expanded 3 mm ID inventive rePTFE endoluminal graft of FIG. 21A taken at 500× magnification.
Figure 21C:
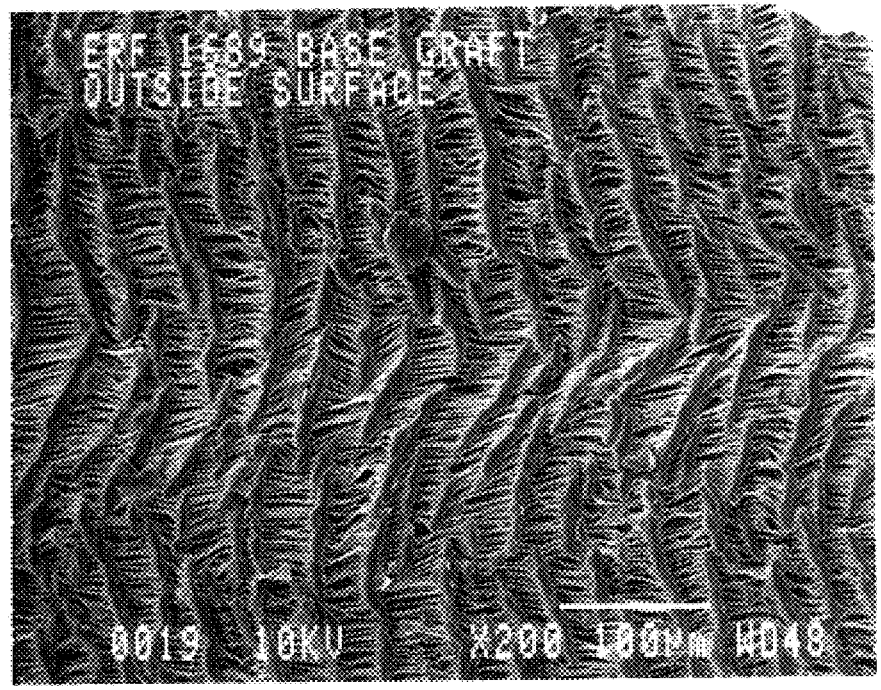
FIG. 21C is a scanning electron photomicrograph of the outer surface of the non-radially expanded 3 mm ID inventive rePTFE endoluminal graft of FIG. 21A at 200× magnification.
Figure 21D:
FIG. 21D is a scanning electron photomicrograph of the outer surface of the non-radially expanded 3 mm ID inventive rePTFE endoluminal graft of FIG. 21 A taken at 500× magnification.
Figure 22A:
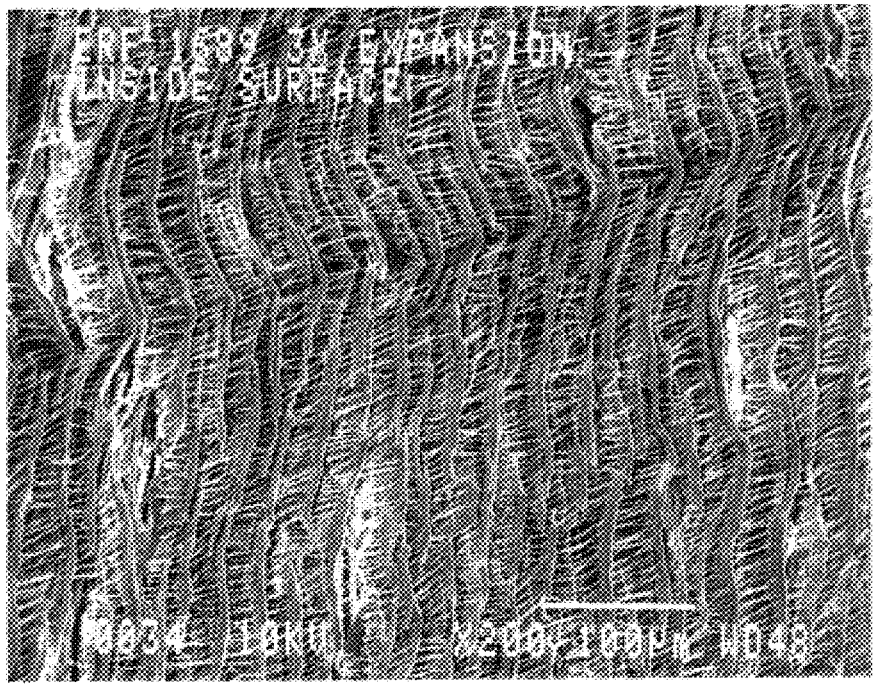
FIG. 22A is a scanning electron photomicrograph of the inner surface of an inventive rePTFE endoluminal graft ERF 1689 radially expanded 3× at 200× magnification.
Figure 22B:
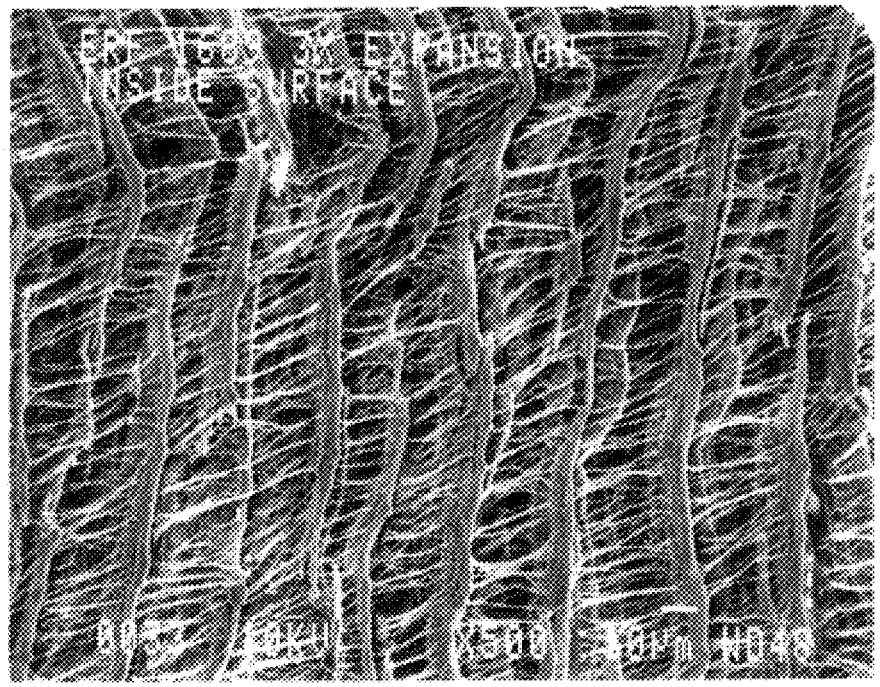
FIG. 22B is a scanning electron photomicrograph of the inner surface of the inventive rePTFE endoluminal graft ERF 1689 of FIG. 22A taken at 500× magnification.
Figure 22C:
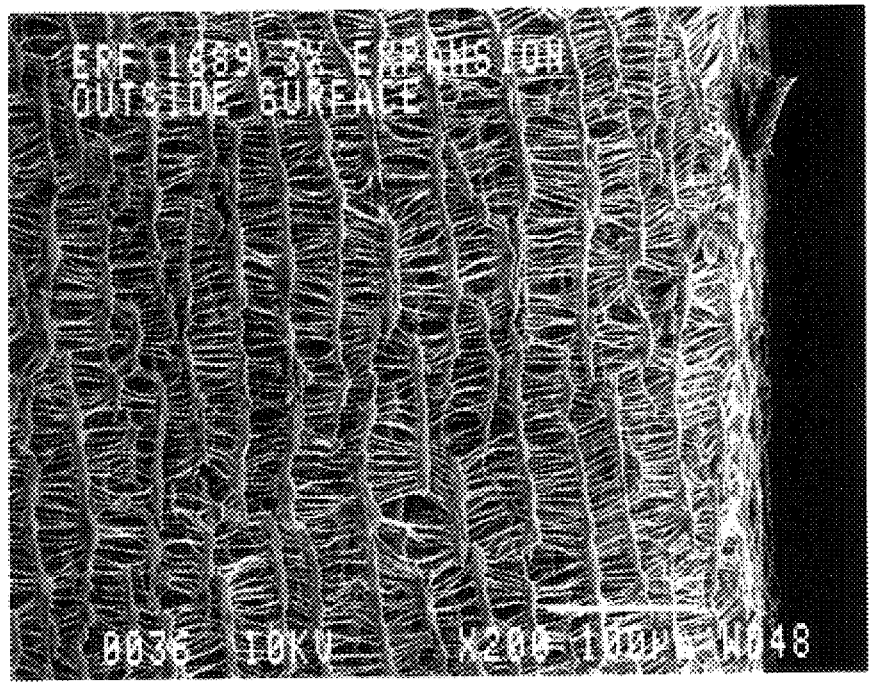
FIG. 22C is a scanning electron photomicrograph of the outer surface of the inventive rePTFE endoluminal graft ERF 1689 of FIG. 22A at 200× magnification.
Figure 22D:
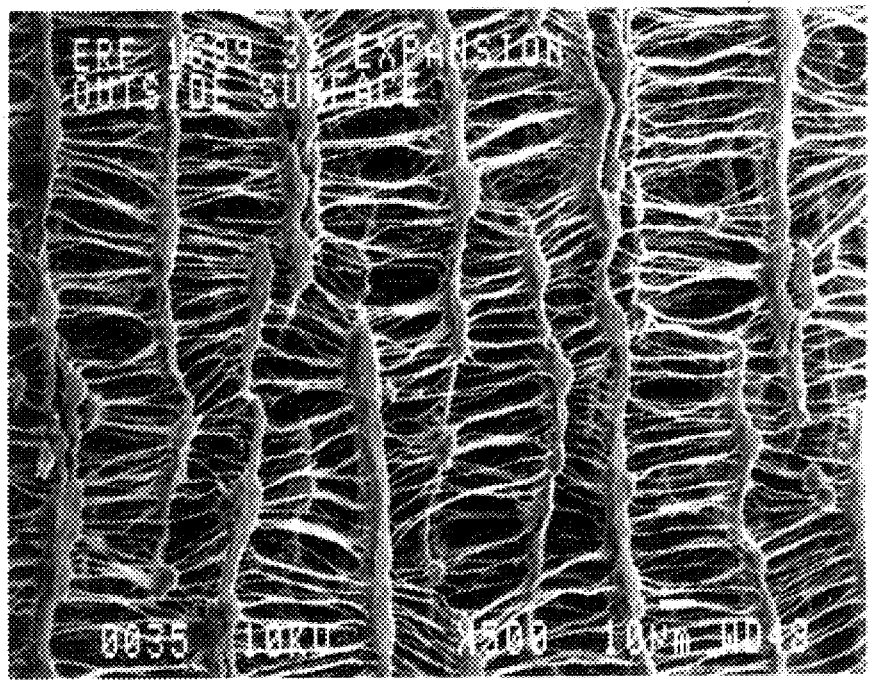
FIG. 22D is a scanning electron photomicrograph of the outer surface of the inventive rePTFE endoluminal graft ERF 1689 of FIG. 22A taken at 500× magnification.
Figure 23A:
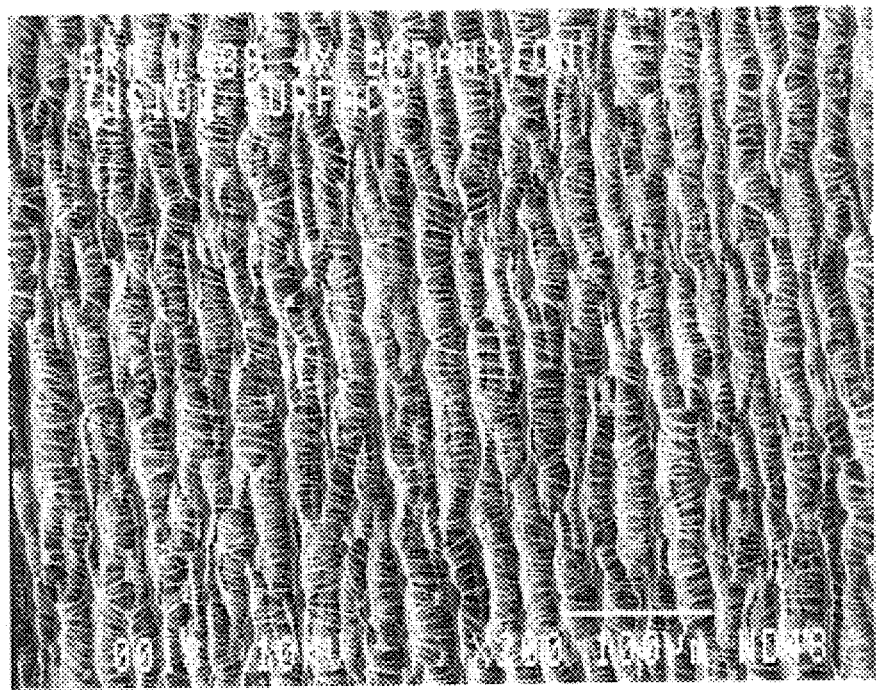
FIG. 23A is a scanning electron photomicrograph of the inner surface of an inventive rePTFE endoluminal graft ERF 1689 radially expanded 4× at 200× magnification.
Figure 23B:
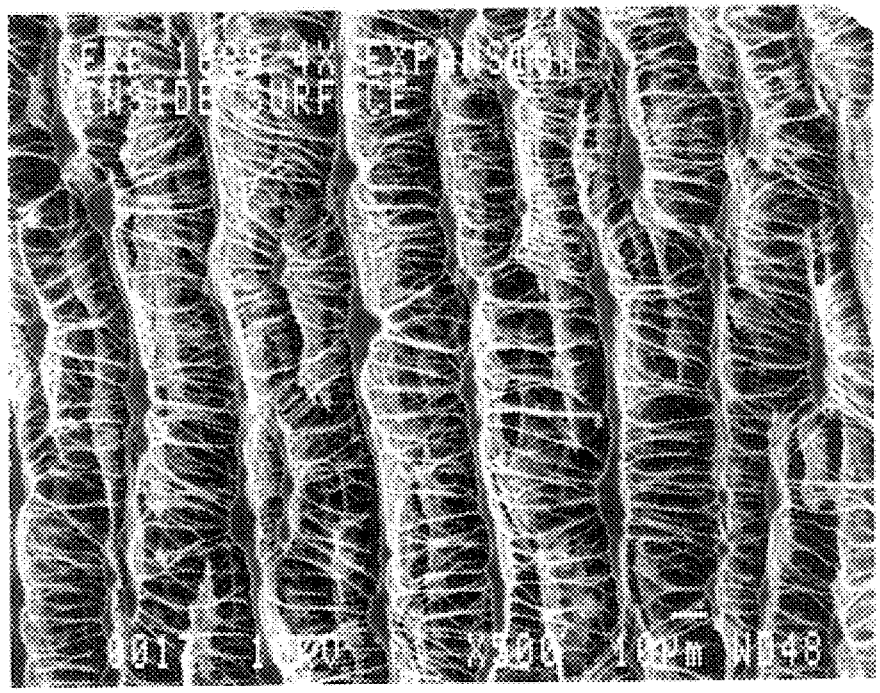
FIG. 23B is a scanning electron photomicrograph of the inner surface of the inventive rePTFE endoluminal graft ERF 1689 of FIG. 23A taken at 500× magnification.
Figure 23C:
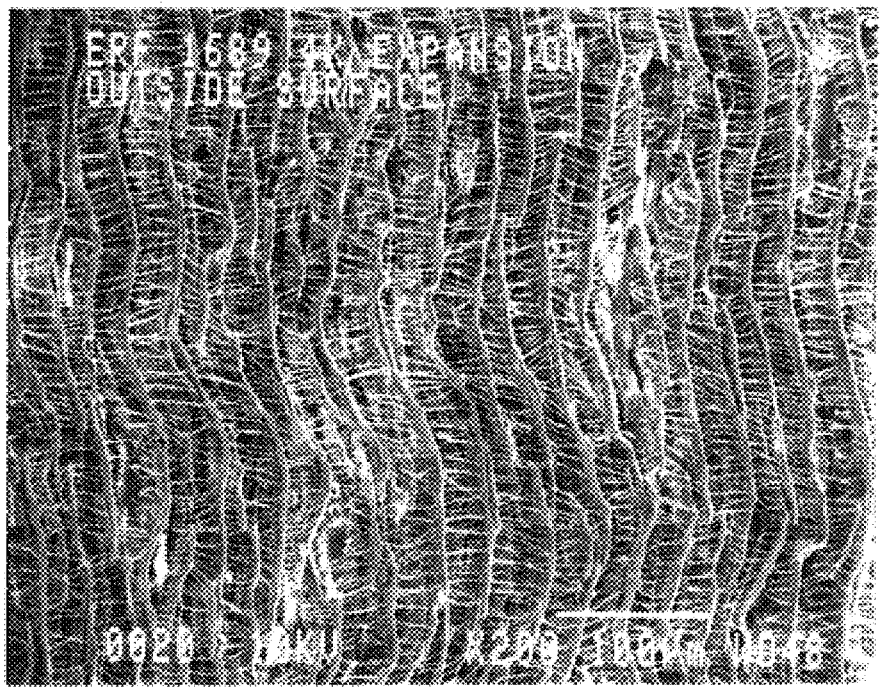
FIG. 23C is a scanning electron photomicrograph of the outer surface of the inventive rePTFE endoluminal graft ERF 1689 of FIG. 23A at 200× magnification.
Figure 23D:
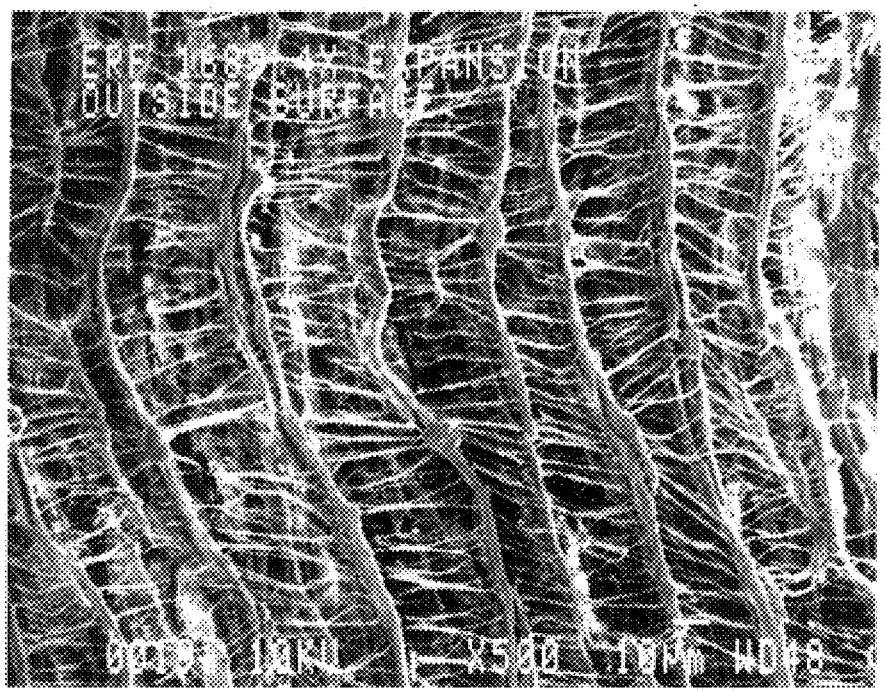
FIG. 23D is a scanning electron photomicrograph of the outer surface of the inventive rePTFE endoluminal graft ERF 1689 of FIG. 23A taken at 500× magnification.
Figure 24A:
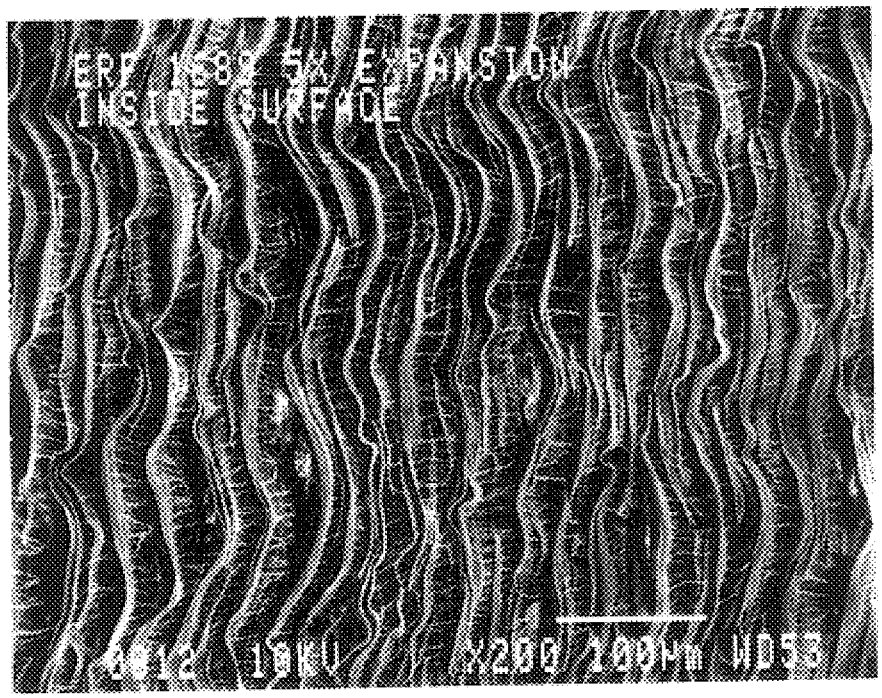
FIG. 24A is a scanning electron photomicrograph of the inner surface of an inventive rePTFE endoluminal graft ERF 1689 radially expanded 5× at 200× magnification.
Figure 24B:
FIG. 24B is a scanning electron photomicrograph of the inner surface of the inventive rePTFE endoluminal graft ERF 1689 of FIG. 24A taken at 500× magnification.
Figure 24C:
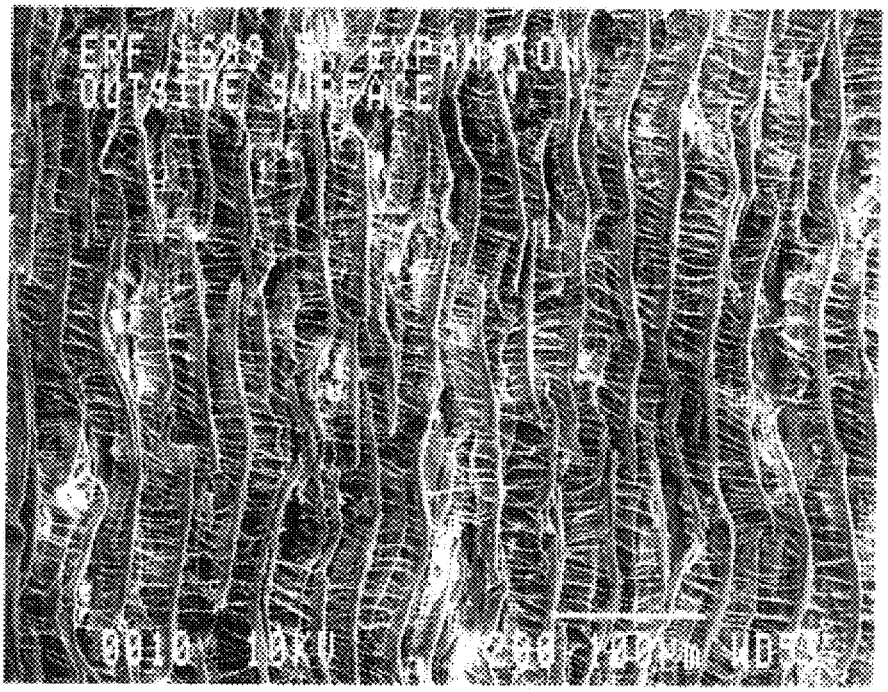
FIG. 24C is a scanning electron photomicrograph of the outer surface of the inventive rePTFE endoluminal graft ERF 1689 of FIG. 24A at 200× magnification.
Figure 24D:
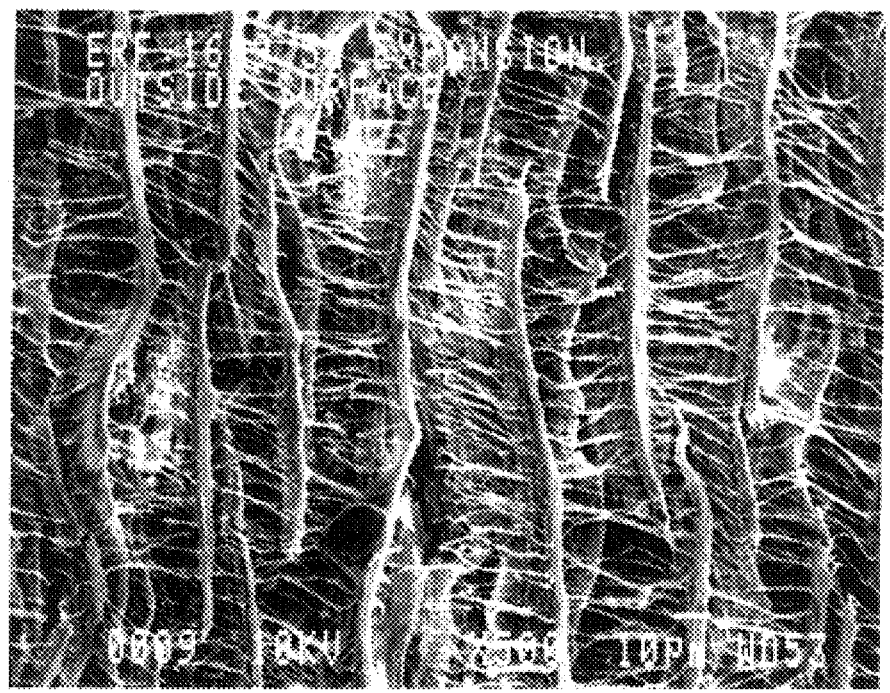
FIG. 24D is a scanning electron photomicrograph of the outer surface of the inventive rePTFE endoluminal graft ERF 1689 of FIG. 24A taken at 500× magnification.

FIGS. 6A–6D are scanning electron micrographs taken at 200 and 500× magnification of the inner and outer surfaces of the standard ePTFE vascular graft of FIGS. 5A–5D which has been radially expanded 3× to an inner diameter of 9 mm. FIGS. 7A–7D are scanning electron micrographs of the inner and outer surfaces of the standard ePTFE vascular graft of FIGS. 5A–5D which has been radially expanded 4× to an inner diameter of 12 mm. FIGS. 8A–8D are scanning electron micrographs of the inner and outer surfaces of the standard ePTFE vascular graft of FIGS. 5A–5D which has been radially expanded 4× to an inner diameter of 15 mm. From this series of micrographs, it will be observed that the nodes have a largely irregular elongate appearance and are asynchronously arrayed in the microstructure. While average outer surface internodal distance of the base graft is $33\mu$, at 3× is $33\mu$, at 4× is $32\mu$ and at 5× is $33\mu$, the micrographs illustrate that the INDs have a non-uniform distribution throughout the material matrix. Morphologically, it will be seen that radial expansion of the conventional IMPRA ePTFE vascular graft results in elongation and thinning of the nodes, which remain irregular in shape, but the INDs continue to have a non-uniform distribution in the material matrix. FIGS. 9A–D are micrographs of inner and outer surfaces of a non-radially expanded 6 mm ID PTFE graft (Lot No. 34396, IMPRA, Inc., Tempe, Ariz.). FIGS. 10A–10B are scanning electron micrographs taken at 200 and 500× magnification of the inner and outer surfaces of the standard ePTFE vascular graft of FIGS. 9A–9D which has been radially expanded 3× to an inner diameter of 18 mm. FIGS. 11A–11D are scanning electron micrographs of the inner and outer surfaces of the standard ePTFE vascular graft of FIGS. 9A–9D which has been radially expanded 4× to an inner diameter of 24 mm. FIGS. 12A–12D are scanning electron micrographs of the inner and outer surfaces of the standard ePTFE vascular graft of FIGS. 9A–9D which has been radially expanded 5× to an inner diameter of 30 mm. From this series of micrographs, it will be observed that, like the 3 mm standard PTFE graft, the nodes have a largely irregular elongate appearance and are asynchronously arrayed in the microstructure. While average outer surface internodal distance of the base graft is $33\mu$, at 3× is $31\mu$, at 4× is $33\mu$ and at 5× is $33\mu$, the micrographs illustrate that the INDs have a non-uniform distribution throughout the material matrix. Morphologically, it will be seen that radial expansion of the conventional IMPRA ePTFE vascular graft results in elongation and thinning of the nodes, which remain irregular in shape, but the INDs continue to have a non-uniform distribution in the material matrix.

In contrast to the standard PTFE graft material, the inventive rePTFE material, represented herein by ERF 1683, ERF 1687 and ERF 1689, shown in their non-radially expanded base state, and at 3×, 4× and 5× radial expansion, in FIGS. 13A–24C, is characterized by a lower node density and lower fibril density in the unexpanded and expanded graft material. Scanning electron microscopy was performed on a JEOL-SM 840 Scanning Electron Microscope and the accompanying micrographs were obtained during scanning electron microscopy. The lower node density is the result of elongation of the nodes as the graft radially expands, while the lower fibril density is the result of increasing interfibril distances due to the nodal elongation. "Interfibril distance" is the perpendicular distance between any two parallel and adjacent fibrils. The nodes in the inventive rePTFE material are characterized by a more uniform regular elongate shape which, during radial expansion, undergo a more regular nodal elongation than that exhibited by the standard PTFE graft material, and fibrils which have a torroidal or "necked" profile. Additionally, as reflected in the accompanying figures, the rePTFE microstructure is characterized by increased tortuosity of the pores than that exhibited by the standard PTFE graft material.

By an examination of the accompanying electron micrographs at FIGS. 13A–24C, it will be seen that the base unexpanded graft has average INDs of approximately $18.2\mu$. The plurality of fibrils have a generally torroidal shape along their longitudinal axis, with the intermediate area of each of the plurality of fibrils having a narrower width than the area at either end of the plurality of fibrils 16 adjacent the nodes which the fibrils connect. The plurality of nodes exhibit a substantially parallel array with the nodes being substantially co-axially aligned in end-to-end fashion along the transverse axis of the graft material.

The electron micrographs at FIGS. 14A–14D, 18A–18D, and 22A–22D, taken of ERF 1683, ERF 1687 and ERF 1689, respectively, radially expanded 3×, illustrate that at 3× expansion the INDs remain substantially the same as the unexpanded graft IND of FIGS. 13A–13D, 17A–17D and 21A–21D, respectively. Additionally, the plurality of nodes retain their co-axial array as in the unexpanded graft material, but are longitudinally deformed along their longitudinal axis and parallel to the axis of radial expansion. The longitudinal profile of the plurality of fibrils also remains generally torroidal in shape. It will be noted, however, that the profile of each of the plurality of nodes has been markedly altered, but in a non-linear manner relative to the degree of gross radial deformation of the ePTFE material itself. After radial deformation, each of the plurality of nodes 14 exhibits an elongated and narrowed profile. Starting at 3× expansion, it becomes apparent that the fibril density in the inventive rePTFE material is greater than that of the conventional ePTFE material and that the fibrils exhibit a more tangled or tortuous appearance than that found in the conventional ePTFE material.

The electron micrographs at FIGS. 15A–15D, 19A–19D and 23A–23D, taken of ERF 1683, ERF 1687 and ERF 1689, respectively, radially expanded 4×, illustrate that at 4× expansion the INDs remain substantially the same as the unexpanded graft IND of FIGS. 13A–13D, 17A–17D and 21A–21D, respectively. At 4× radial expansion the increased tortuosity of the fibrils becomes even more apparent in the accompanying figures. While the interfibril distance continues to increase, the electron micrographs reflect that the each interfibrilar space is bounded in the z-axis by another fibril in close proximity to the interfibrilar space, which imparts the increased tortuosity of the rePTFE microstructure.

At 5× radial expansion, illustrated with reference to the electron micrographs at FIGS. 16A–16D, 20A–20D and 24A–24D, taken of taken of ERF 1683, ERF 1687 and ERF 1689, respectively, the interfibril distance has increased relative to both the base graft, or the rePTFE graft at 3× or 4× radial expansion, while the IND remains substantially the same as that of the base rePTFE graft or that at 3× or 4× radial expansion. Additionally, the nodes have again elongated along the axis of radial expansion to form long, columnar nodes which have a generally regular distribution throughout the microstructure wherein a substantial majority of the nodes are separated by substantially uniform INDs.

Figure 4:
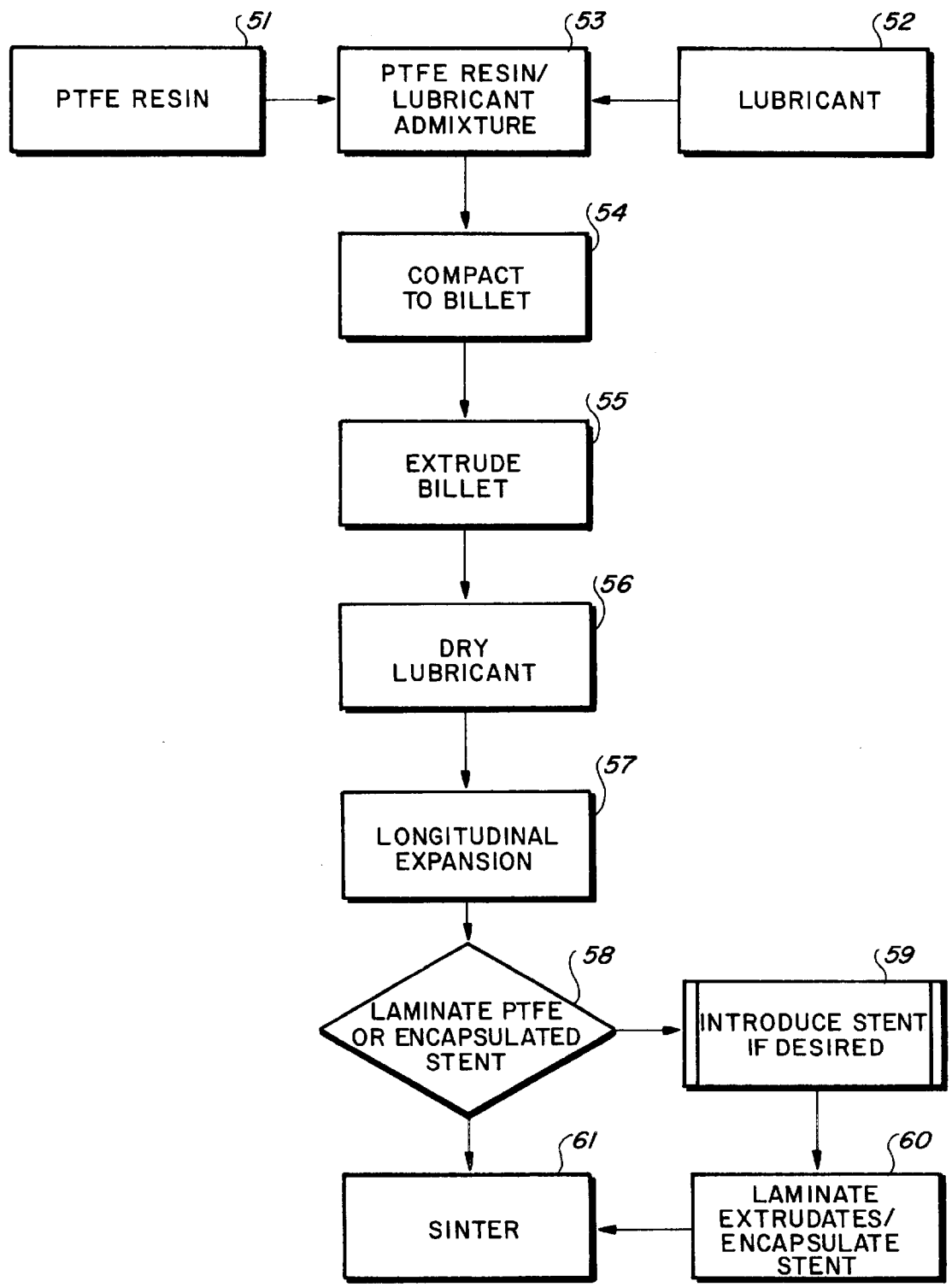
FIG. 4 is a process flow diagram illustrating the inventive method for making radially expandable polytetrafluoroethylene tubes.
Figure 5A:
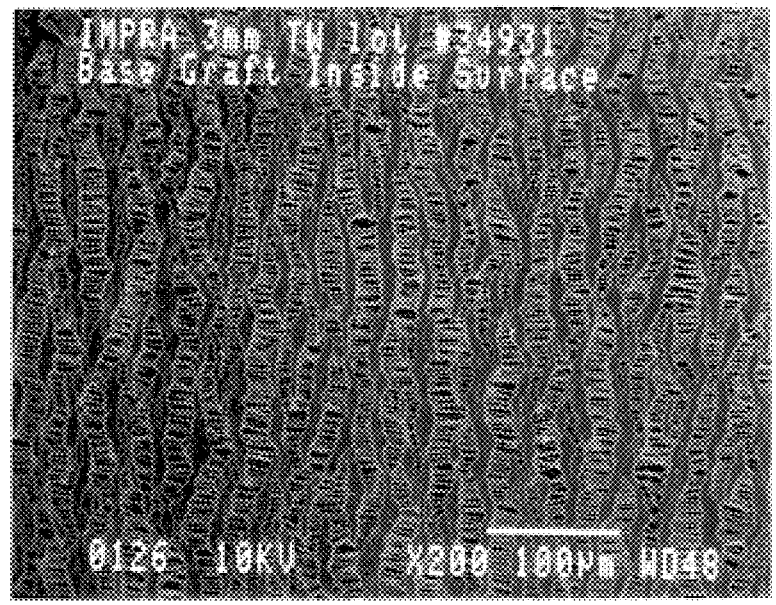
FIG. 5A is a scanning electron photomicrograph of the inner surface of a 3 mm ID conventional non-radially expanded ePTFE vascular graft at 200× magnification.
Figure 5B:
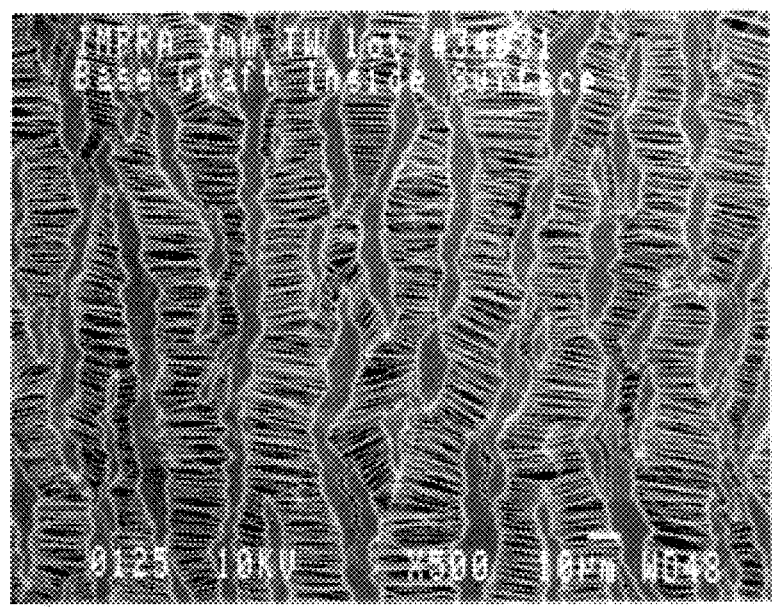
FIG. 5B is a scanning electron photomicrograph of the inner surface of the 3 mm ID conventional non-radially expanded ePTFE vascular graft of FIG. 5A taken at 500× magnification.
Figure 5C:
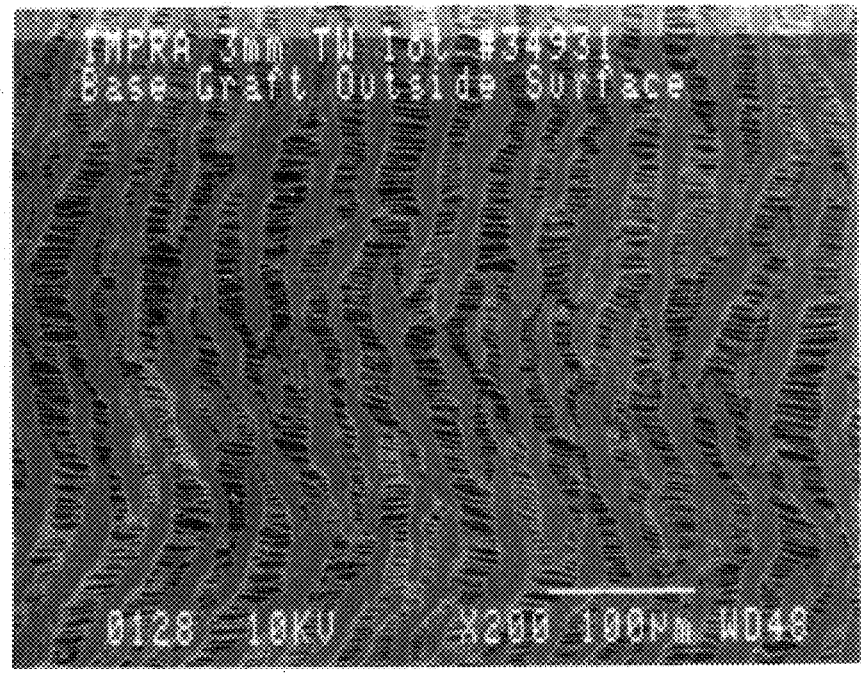
FIG. 5C is a scanning electron photomicrograph of the outer surface of the 3 mm ID conventional non-radially expanded ePTFE vascular graft of FIG. 5A at 200× magnification.
Figure 5D:
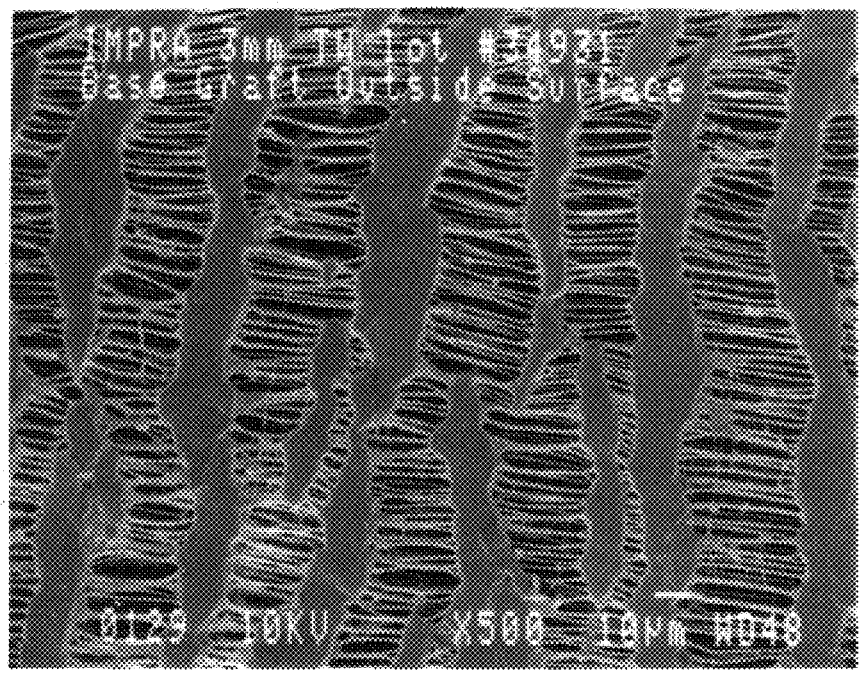
FIG. 5D is a scanning electron photomicrograph of the outer surface of the 3 mm ID conventional non-radially expanded ePTFE vascular graft of FIG. 6A taken at 500× magnification.
Figure 6A:
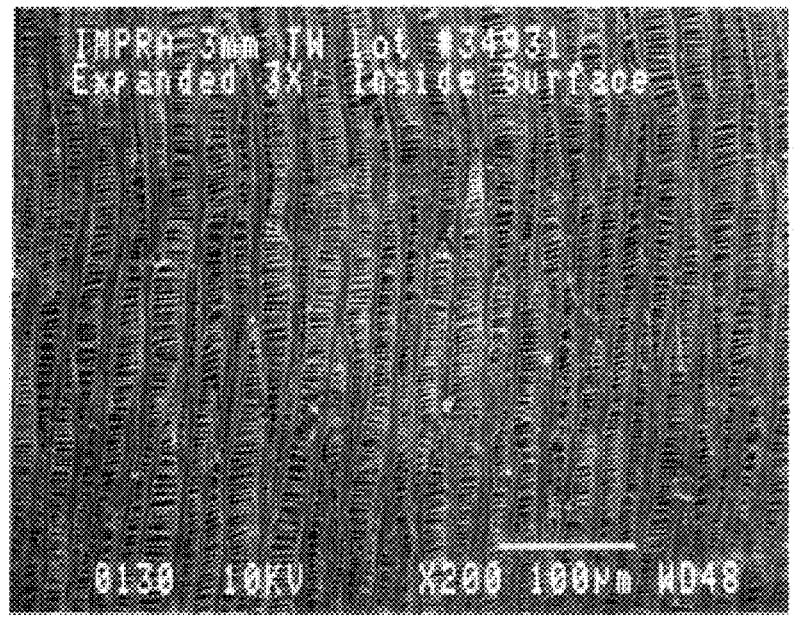
FIG. 6A is a scanning electron photomicrograph of the inner surface of a 3 mm ID conventional expanded ePTFE vascular graft radially expanded 3× at 200× magnification.
Figure 6B:
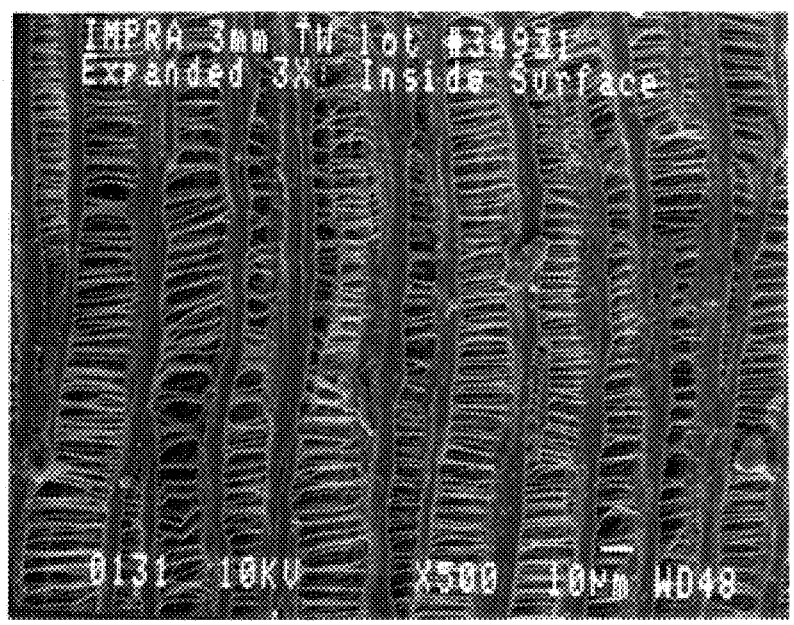
FIG. 6B is a scanning electron photomicrograph of the inner surface of the 3 mm ID conventional expanded ePTFE vascular graft of FIG. 6A taken at 500× magnification.
Figure 6C:
FIG. 6C is a scanning electron photomicrograph of the outer surface of the 3 mm ID conventional expanded ePTFE vascular graft of FIG. 6A at 200× magnification.
Figure 6D:
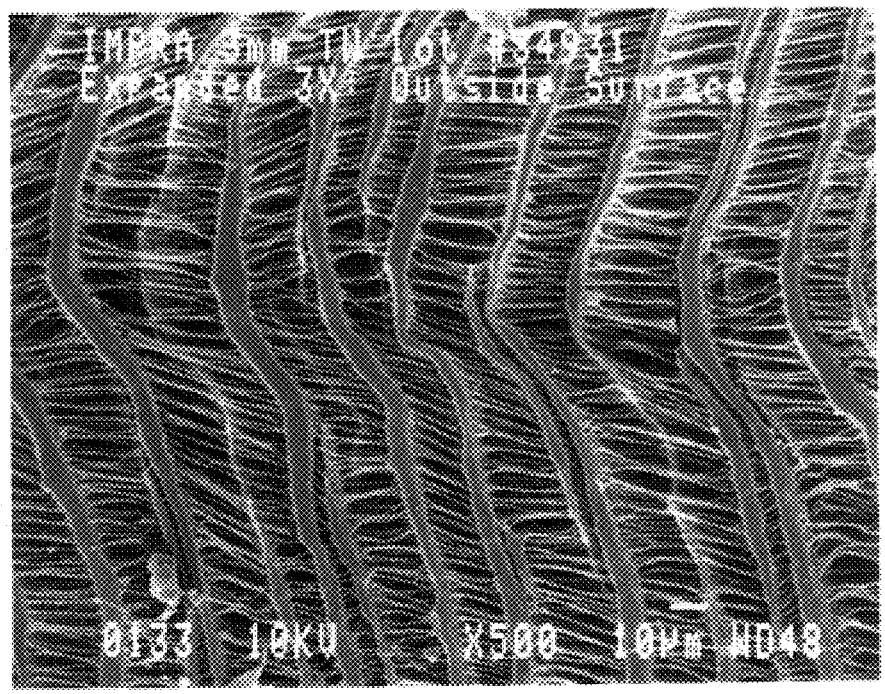
FIG. 6D is a scanning electron photomicrograph of the outer surface of the 3 mm ID conventional expanded ePTFE vascular graft of FIG. 6A taken at 500× magnification.
Figure 7A:
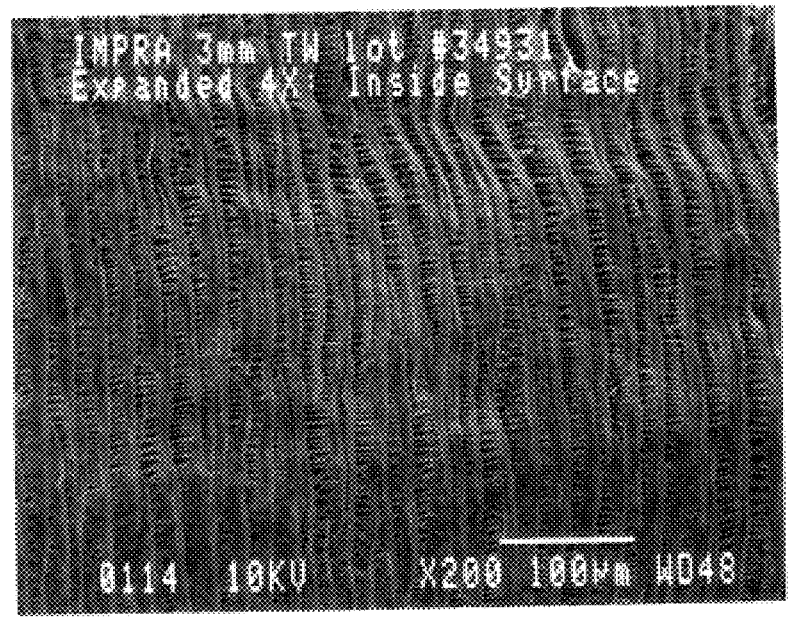
FIG. 7A is a scanning electron photomicrograph of the inner surface of a 3 mm ID conventional expanded ePTFE vascular graft radially expanded 4× at 200× magnification.
Figure 7B:
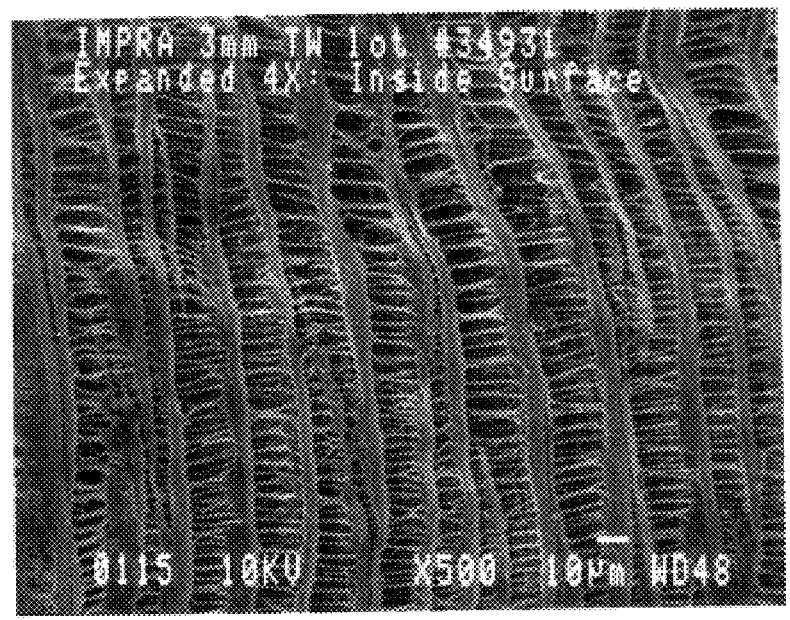
FIG. 7B is a scanning electron photomicrograph of the inner surface of the 3 mm ID conventional expanded ePTFE vascular graft of FIG. 7A taken at 500× magnification.
Figure 7C:
FIG. 7C is a scanning electron photomicrograph of the outer surface of the 3 mm ID conventional expanded ePTFE vascular graft of FIG. 7A at 200× magnification.
Figure 7D:
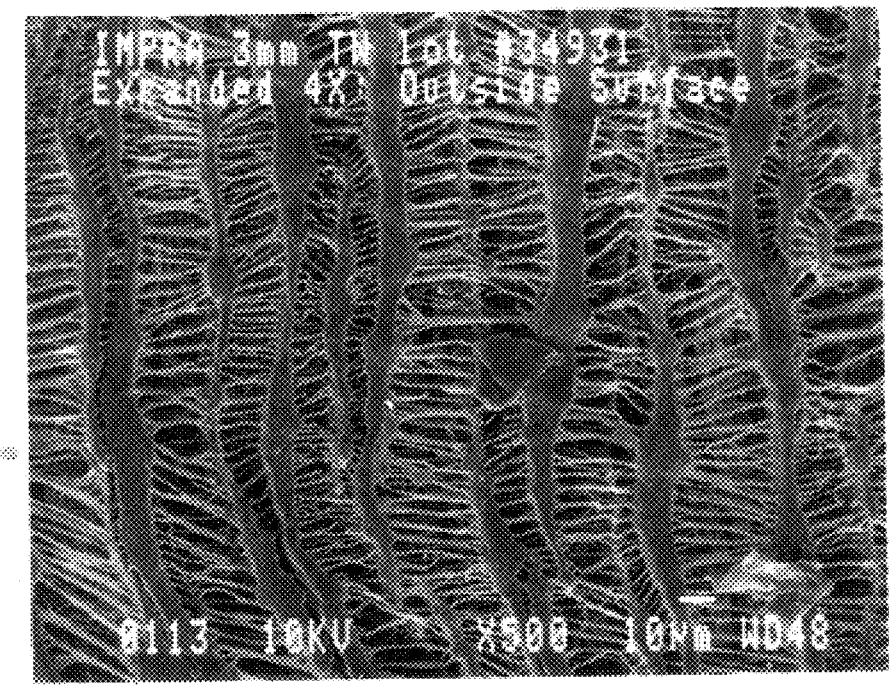
FIG. 7D is a scanning electron photomicrograph of the outer surface of the 3 mm ID conventional expanded ePTFE vascular graft of FIG. 7A taken at 500× magnification.
Figure 8A:
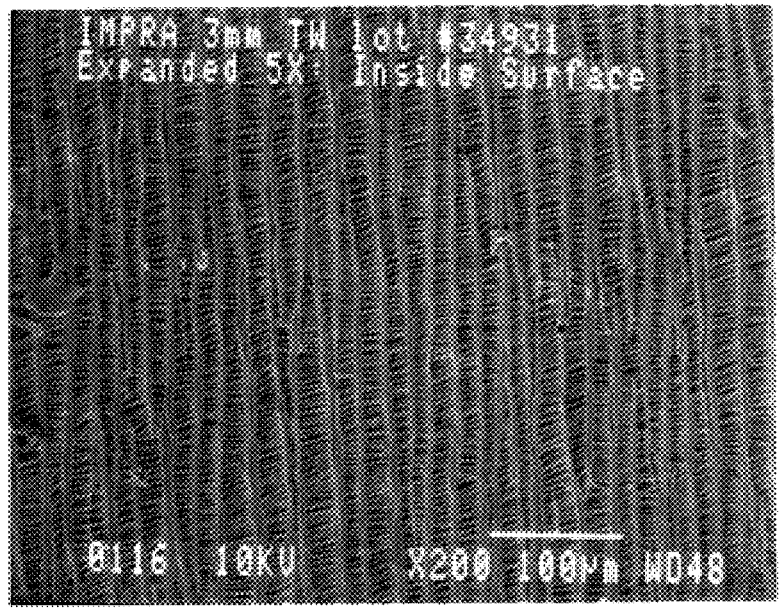
FIG. 8A is a scanning electron photomicrograph of the inner surface of a 3 mm ID conventional expanded ePTFE vascular graft radially expanded 5× at 200× magnification.
Figure 8B:
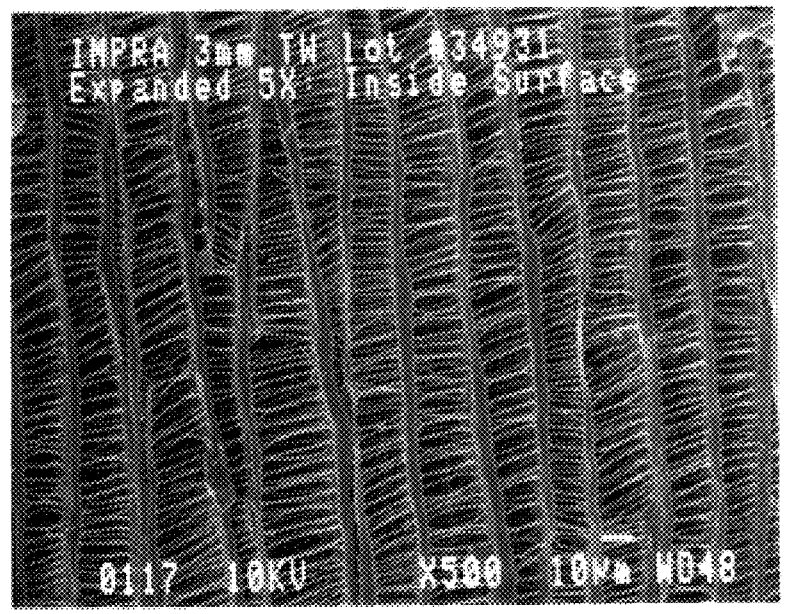
FIG. 8B is a scanning electron photomicrograph of the inner surface of the 3 mm ID conventional expanded ePTFE vascular graft of FIG. 8A taken at 500× magnification.
Figure 8C:
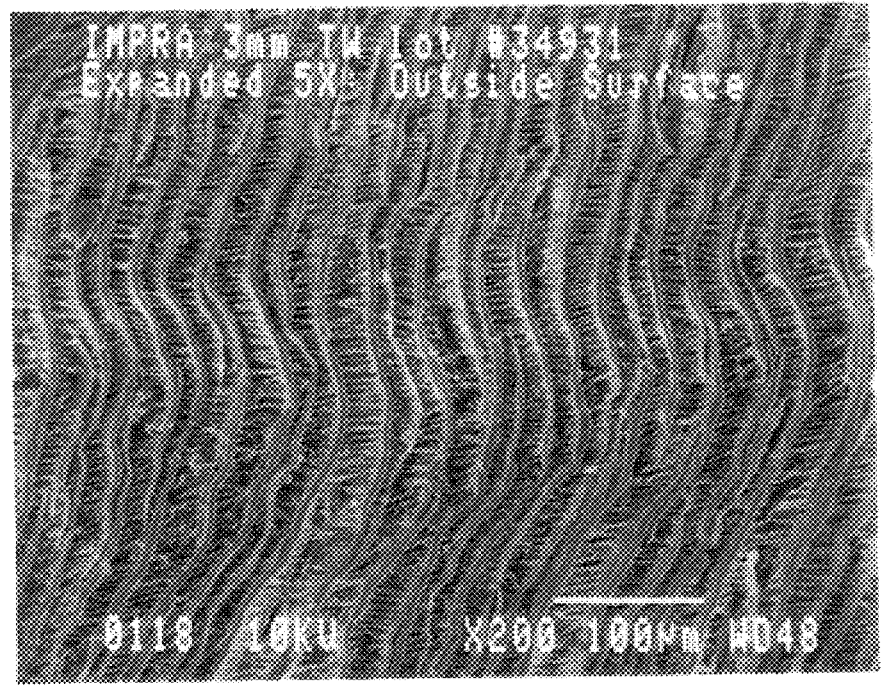
FIG. 8C is a scanning electron photomicrograph of the outer surface of the 3 mm ID conventional expanded ePTFE vascular graft of FIG. 8A at 200× magnification.
Figure 8D:
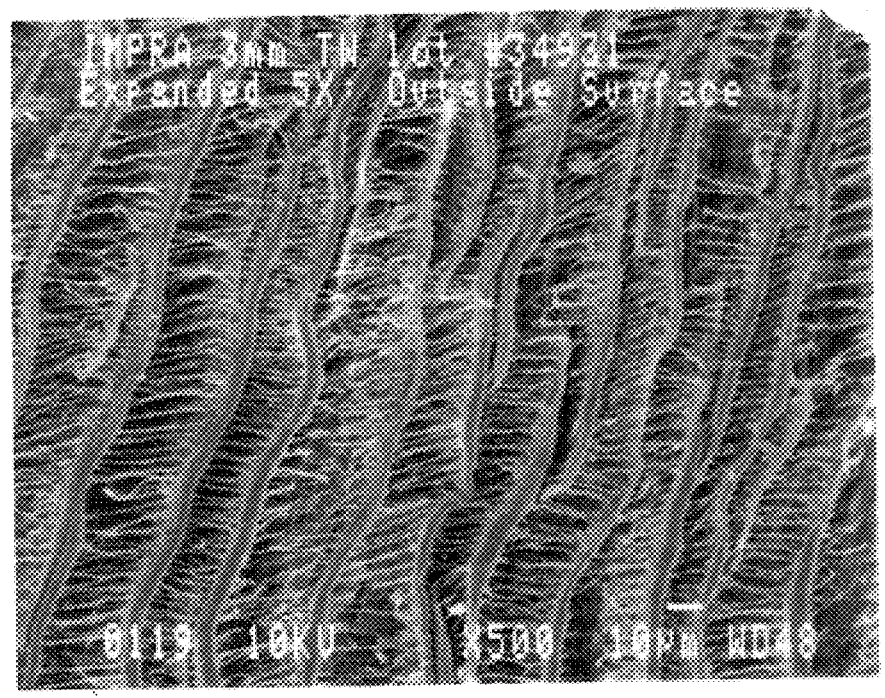
FIG. 8D is a scanning electron photomicrograph of the outer surface of the 3 mm ID conventional expanded ePTFE vascular graft of FIG. 8A taken at 500× magnification.
Figure 9A:
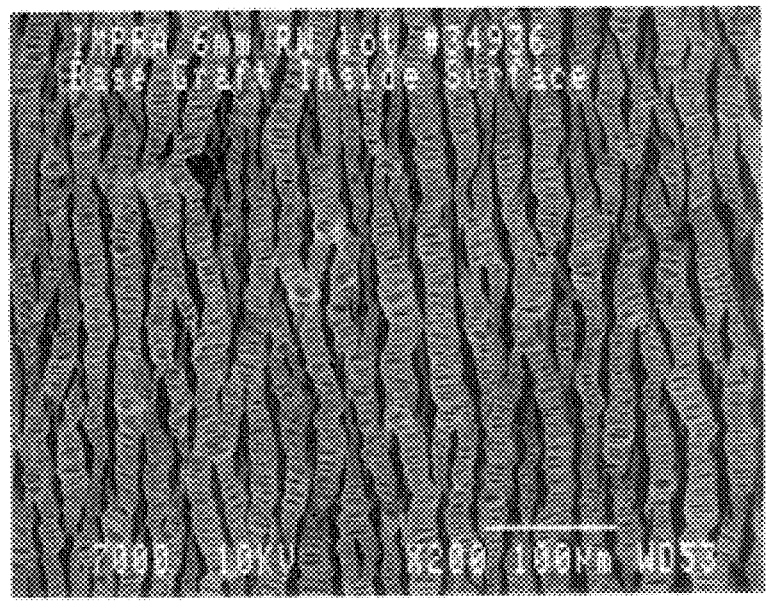
FIG. 9A is a scanning electron photomicrograph of the inner surface of a 6 mm ID conventional non-radially expanded ePTFE vascular graft at 200× magnification.
Figure 9B:
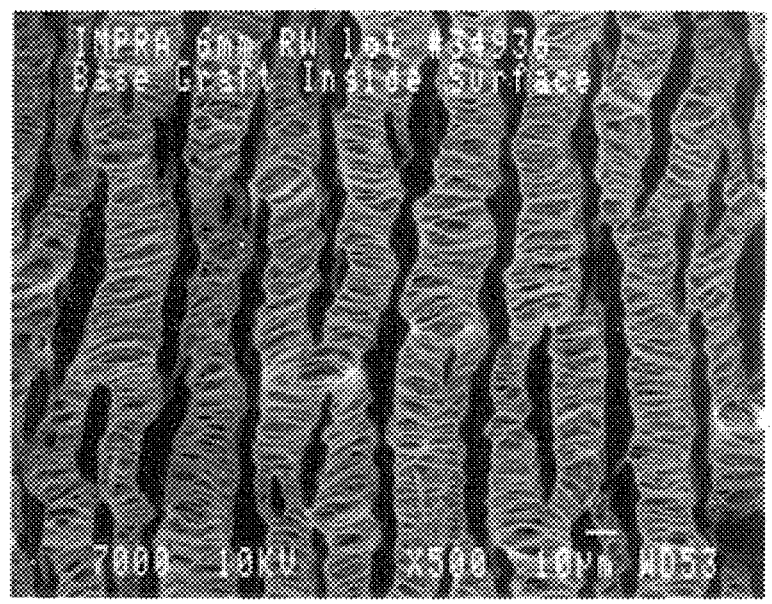
FIG. 9B is a scanning electron photomicrograph of the inner surface of the 6 mm ID conventional non-radially expanded ePTFE vascular graft of FIG. 9A taken at 500× magnification.
Figure 9C:
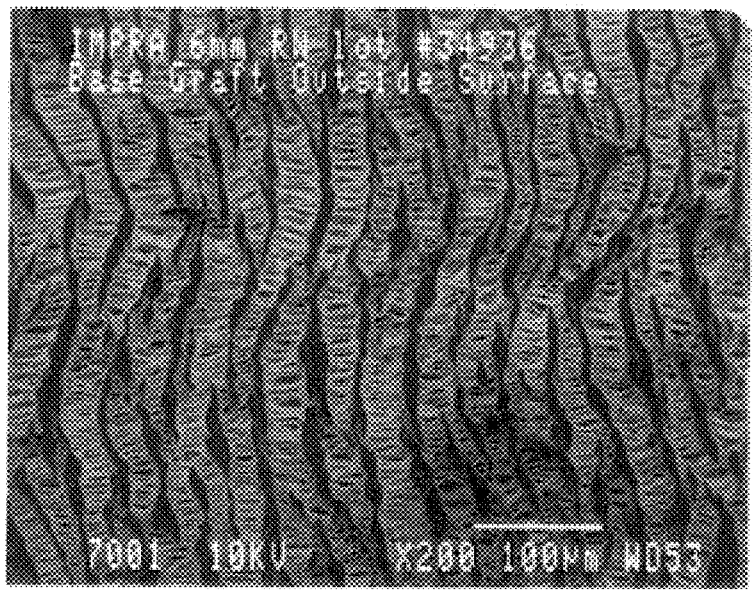
FIG. 9C is a scanning electron photomicrograph of the outer surface of the 6 mm ID conventional non-radially expanded ePTFE vascular graft of FIG. 9A at 200× magnification.
Figure 9D:
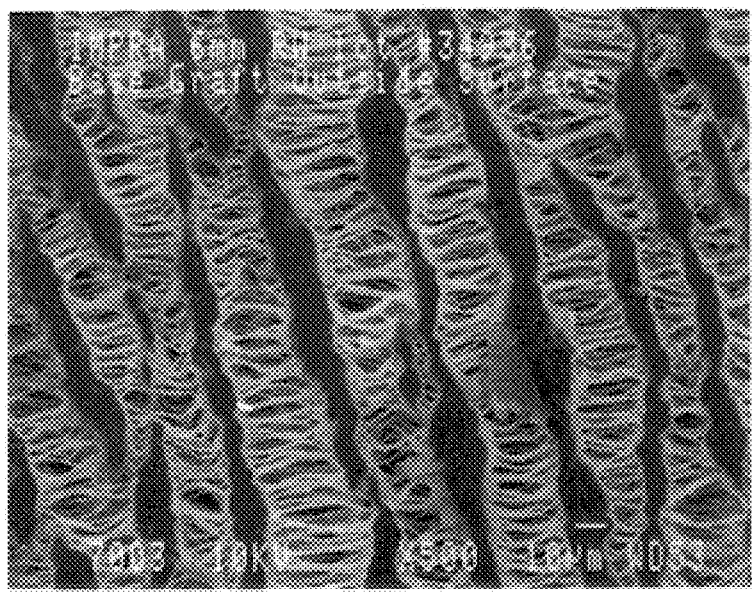
FIG. 9D is a scanning electron photomicrograph of the outer surface of the 6 mm ID conventional non-radially expanded ePTFE vascular graft of FIG. 9A taken at 500× magnification.

Radially deformable, longitudinally expanded PTFE tubular graft members meeting the criteria of the present invention are made by the method 50 for making radially expandable PTFE tubes illustrated generally in FIG. 4. In accordance with the inventive method the general method steps consist of providing a polytetrafluoroethylene resin 51 preferably having an average molecular weight about 120 Million and an average particle size between 350 and 750μ, and an extrusion lubricant 52, such as ISOPAR H (Exxon Chemical), and admixing the PTFE resin and lubricant at step 53. It is preferable that the lubricant be present in the admixture at a ratio of between about 13.5% to about 18% by weight. The PTFE-lubricant admixture is refrigerated overnight, then is formed into an extrusion billet by pouring the PTFE-lubricant admixture into an upright vertical stainless steel cylinder having a central co-axial vertical preform shaft therein. The vertical stainless steel cylinder is a billet preform which has a diameter corresponding to a diameter of an extrusion barrel in a ram extruder used to extrude the billet. For example, if the ram extruder has an extrusion barrel inner diameter of 3.81 cm, it is desirable for the extrusion billet to have an outer diameter no greater than 3.81 cm. Thus, it is preferable to match the inner diameter of the billet preform to the inner diameter of the extrusion barrel. Once the PTFE-lubricant admixture is poured into the upright vertical billet preform, an annular ram plate is engaged over the central co-axial vertical shaft and within the billet preform. A ram press is then engaged onto the annular ram plate and the PTFE-lubricant admixture is compressed under pressure until a compacted extrusion billet is formed at step 54. The extrusion billet produced at step 54 is then removed from the billet preform and the preform shaft and engaged upon an extrusion shaft and extrusion mandrel and introduced into the extrusion barrel of a ram extruder. The billet is then extruded at step 55 in a ram extruder having an annular extrusion orifice formed between the inner diameter of the extrusion die and the extrusion mandrel tip concentrically engaged within the extrusion die. To form PTFE tubes, the extrusion die has a frustroconical taper with a conical taper along the axis of extrusion. A mandrel tip is engaged onto the extrusion shaft at its distal end along the axis of extrusion. The mandrel tip also has a conical taper along the axis of extrusion. The degree to which the PTFE extrusion billet is reduced in cross-sectional area as it passes during extrusion is known as the "reduction ratio" and is expressed by the following equation:

$$RR = \frac{\Pi\left(\frac{D_{barrel}}{2}\right)^2 - \Pi\left(\frac{D_{shaft}}{2}\right)^2}{\Pi\left(\frac{D_{die}}{2}\right)^2 - \Pi\left(\frac{D_{mandrel}}{2}\right)^2}$$

in which RR is the reduction ratio, $D_{barrel}$ is the inner diameter of the extruder barrel, $D_{shaft}$ is the outer diameter of the extrusion shaft, $D_{die}$ is the inner diameter of the exit orifice of the extrusion die and $D_{mandrel}$ is the outer diameter of the extrusion mandrel at its distal end relative to the axis of extrusion.

As the tubular PTFE is extruded, it issues from the die exit orifice as a continuous tubular PTFE extrudate and is cut using a sharp razor blade into any length desired, e.g., 30 cm lengths. The PTFE tubular extrudate lengths are then introduced into an oven at a temperature below the flash point of the lubricant, for example at 40° C. for ISOPAR H (Exxon Chemical), for a period of time sufficient to drive off and dry, at step 56, substantially all of the lubricant present in the PTFE tubular extrudate, for example, for about 60 minutes. Once the PTFE tubular extrudate is dried of lubricant, expansion plugs are secured into the tube lumen at each opposing end of the PTFE tubular extrudate length, and the plugged PTFE tubular extrudates are mounted onto an expansion rack. The expansion rack is designed to be mounted into an expansion oven and has a gear, screw, or rail driven moveable stage to which one end of the PTFE tubular extrudate is attached and a stationary stage to which another end of the PTFE tubular extrudate is attached. The PTFE tubular extrudate, mounted on the expansion rack, is introduced into an expansion oven heated to a temperature below the second crystalline melt point of PTFE, preferably between 125 and 340° C., most preferably between 150 and 200° C., and allowed to dwell in the expansion oven for a period of time between 5 and 10 minutes, preferably about 7–8 minutes, before longitudinally expanding the PTFE tubular extrudate.

Longitudinal expansion of the tubular PTFE extrudates at step 57 is performed after the dwell time for the PTFE extrudates has elapsed. Wide variation in the expansion rate for making different ePTFE products is known. However, in order to impart increased ability of the inventive rePTFE to radially expand at applied pressures of less than about 6 atm., it is preferable that the longitudinal expansion be performed at a rate between about 10 and 200%/sec.

After the PTFE extrudates have been longitudinally expanded at step 57, and prior to sintering the PTFE extrudates, the unsintered PTFE extrudates may either be concentrically laminated with other larger or smaller diameter unsintered PTFE extrudates, or may be concentrically positioned about luminal and abluminal surfaces of an endoluminal stent at step 58. An endoluminal stent, which may be a balloon expandable, self-expandable or a shape memory stent, may be introduced at step 59 by concentrically positioning an endoluminal stent around a first unsintered PTFE extrudate, then a second unsintered PTFE extrudate of a slightly larger inner diameter may be introduced concentrically around the first unsintered PTFE extrudate and the endoluminal stent, as more fully described in co-pending PCT International Application WO96/28115, published Sep. 19, 1996, claiming priority from co-pending U.S. patent applications Ser. Nos. 08/401,871 filed Mar. 10, 1995 and 08/508,033 filed Jul. 27, 1995, which are expressly incorporated by reference as exemplifying a process for making an encapsulated stent graft.

If the introduction of a stent is not desired, or if the stent is to be positioned along only a particular longitudinal section of a PTFE extrudate, the PTFE tubular extrudates concentrically positioned relative to one another are then laminated by application of a helically applied tension wrap of non-porous PTFE tape which applies a circumferential pressure to the concentrically positioned laminated tubular PTFE extrudates and/or to the concentrically positioned laminated tubular PTFE extrudates and stent assembly at step 60.

The wrapped assembly, either a laminated tubular PTFE extrudate assembly or a laminated tubular PTFE extrudate and endoluminal stent assembly, is then introduced into a sintering oven set to heat the wrapped assembly to a temperature above the second transition crystalline melt point of PTFE, i.e., above 342° C., preferably 375° C. +10 −5, for a period of time sufficient to fully sinter the PTFE laminated assembly. In order to increase the bond strength between adjacent PTFE layers in the laminated tubular PTFE extrudate assembly or the laminated tubular PTFE extrudate and endoluminal stent assembly, it has been found desirable to utilize a sintering oven having a radiant heating source and sinter the wrapped assembly between 8 to 12 minutes. Alternatively, the wrapped assembly may be sintered in a convection oven for a period of time preferably between 45 and 90 seconds, most preferably between 60 and 90 seconds.

After being removed from the sintering oven and allowed to cool, the helical wrap of PTFE table is removed from the wrapped assembly and the assembly is inspected for material characterization and defects, then sterilized for physiological use.

Table 1, below, summarizes the preferred processing parameters used for making the inventive rePTFE tubular grafts which exhibit up to 700% radial expandability at applied pressures of less than about 6 atm, preferably less than or equal to about 4 atm., most preferably between 2–3 atm.

TABLE 1

| | ERF 1683 | ERF 1687 | ERF 1689 | ERF$_{encap}$ |
| --- | --- | --- | --- | --- |
| Resin Type | CD 123 | CD 123 | CD 123 | CD 123 |
| Resin Amt(g) | 500 | 500 | 500 | 500 |
| Lube Amt.(g) | 87 | 87 | 100 | 100 |
| Reduction Ratio | 239 | 239 | 239 | 239 |
| Expansion Ratio | 5.3:1 | 5.3:1 | 5.3:1 | 6:1 |
| Expansion Rate(%/sec) | 200 | 10 | 200 | 200 |
| Expansion Temp.(° C.) | 150 | 340 | 340 | 200 |
| Expansion Time(min) | 5 | 5 | 5 | 7 |
| Sintering Temp.(° C.) | 375 | 375 | 375 | 367 |
| Sintering Time(sec) | 60 | 60 | 60 | 480 |
| Expansion Pressure(atm) | 2.8 ± 0.1 | 2.6 ± 0.28 | 2.3 ± 0.12 | n/a |

The following examples set forth the procedures used in making the rePTFE grafts summarized in Table 1, above.

EXAMPLE 1

A 3 mm inner diameter (ID) radially expandable ePTFE tube was fabricated by admixing 500 g of CD-123 PTFE resin (ICI Americas, Inc.) with 87 g of ISOPAR H (Exxon Chemicals), yielding a 17.4% lubricant level ("Lube Level") in the admixture. The admixture was mixed by rolling in a glass container, then incubated at 40° C. for 6 to 8 hours. After incubation, the admixture was poured into a cylindrical pre-form having an inner diameter of 3.81 cm. And compressed in a vertical ram press at about 1,100 psi to form a cylindrical extrusion billet. The extrusion billet was carefully removed from the cylindrical pre-form, wrapped in aluminum foil and incubated prior to use.

The extrusion billet was mounted onto a cylindrical stainless steel base shaft having a diameter of 0.357 cm which passed through the central longitudinal axis of the extrusion billet and projected beyond both ends of the extrusion billet. A tapered extrusion mandrel has a proximal end which is coupled to the base shaft and has proximal end diameter of 0.357 cm and tapers to a mandrel tip at the distal end of the mandrel which has an outer diameter of 0.335 cm. The extrusion billet was then mounted in the extrusion barrel of a ram extruder, the extrusion barrel having an inner diameter of 3.81 cm, and a tapered extrusion die having an entry opening inner diameter of 3.81 cm tapering to a circular exit orifice of 0.412 cm inner diameter. The mandrel tip is co-axially aligned to pass centrally into the circular exit orifice of the extrusion die forming an annular exit orifice. The annular exit orifice is defined between the inner surface of the circular exit orifice of the extrusion die and the outer surface of the mandrel tip and forms an opening having a thickness of 0.076 cm. The extrusion billet is then extruded in the ram extruder at an extrusion speed of 3000 mm/min to yield a wet tubular extrudate. The wet tubular extrudate is cut using a razor blade into 30 cm sections as it issues from the extrusion die.

Cylindrical stainless steel expansion plugs are inserted into the opposing ends of the wet tubular extrudate and secured by crimping a metal band about the outer surface of the wet tubular extrudate to create an interference fit between the crimped metal band, the PTFE wet tubular extrudate and the plug, as more fully explained in U.S. Pat. No. 5,453,235, which is hereby incorporated by reference for the procedure of affixing the plugs to the tubular extrudate.

The wet tubular extrudate is then mounted onto a drying and expansion rack and introduced into a pre-heated oven at 40° C. for 60 minutes to dry the lubricant from the PTFE resin. The dried tubular extrudate is then allowed to dwell in an oven heated to 340° C., then longitudinally expanded at an expansion rate of 200%/sec for an overall longitudinal expansion ratio of 530%. The longitudinally expanded extrudate is then sintered at 375° C. for 60 seconds and removed from the sintering oven, removed from the drying and expansion rack, hung vertically and allowed to cool.

After cooling, the expansion plugs and crimp bands are removed from the ePTFE tubes and sterilized in ethylene oxide. The 3 mm inner diameter radially expandable tubes produced in the Example 1 tube are hereinafter referred to as lot ERF 1683.

EXAMPLE 2

The same processing parameters were followed in as in Example 1, except that the expansion rate was changed to 10%/sec. 3 mm inner diameter radially expandable tubes produced in Example 2 are hereinafter referred to as lot ERF 1687.

EXAMPLE 3

The same processing parameters were followed as in Example 1, except that the lubricant amount was changed to 100 g yielding a lube level of 20%. The 3 mm inner diameter radially expandable tubes produced in Example 3 are hereinafter referred to as lot ERF 1689.

EXAMPLE 4

The same process parameters were followed as in Example 1, except that the lubricant amount was changed to 110 g, yielding a lube level of 22%, the expansion ratio was changed to 6:1, the PTFE extrudate was allowed to dwell in the expansion oven for 7 minutes prior to expansion and the expansion was conducted at 200° C. The resulting 3 mm inner diameter radially expandable tubes produced in Example 4 are hereinafter referred to as lot $ERF_{encap}$.

EXAMPLE 5

One 3 mm and one 4 mm ID unsintered tube produced in accordance with the process in Example 4 were obtained. A 3 mm inner diameter (ID) unsintered tube was loaded onto a 3.56 mm mandrel. Opposing end sections of the tube were wrapped with TEFLON tape to prevent slippage on the mandrel. Next, two P-394 "PALMAZ" stents and two P-308 "PALMAZ" stents were pre-dilated on a 4.74 mm mandrel. The pre-dilated stents were then loaded over the 3 mm ePTFE tube and spaced equidistantly from one another along the length of the 3 mm ePTFE graft. The pre-dilated stents were then crimped down onto the mandrel and the outer surface of the 3 mm ePTFE graft. Next, a 4 mm ID graft was loaded over the crimped stents. The 4 mm ePTFE graft was wire wrapped onto the assembly at its ends and between the crimped stents. Subsequent to the loading steps, the wrapped assembly was then warmed in a radiant heat oven at 340° C. for 30 seconds and then removed. The entire assembly was then wrapped with TEFLON tape using a helical winder set to apply the winding at 1.7 psi. The wrapped assembly was then placed in a radiant heat sintering oven preheated to 400° C. and heated at sintering temperatures of 367° C. for a total of 8 minutes. The TEFLON taped assembly was then removed from the oven and the TEFLON tape and wire wraps were removed. The ePTFE grafts were then cut about one inch outside of each of the ends of the stents. Finally, the resulting encapsulated stents were gently removed from the mandrel one at a time and then cut to provide a 3 mm ePTFE overhang at both ends of the individual stents. Sintering in a radiant heat oven for longer periods of time than in a convection oven was found to increase the bond strength of the laminated PTFE layers in the encapsulated stent.

Ten encapsulated stents were tested for bond strength between the inner and outer ePTFE layers of the encapsulated stent. The bond strength testing was quantified by performing longitudinal peel tests on an INSTRON tester and formalizing for adhesion strength per unit length. Each encapsulated stent was cut into two strips (A & B) with each strip being approximately 5.5 mm wide and 25.4 mm long. Opposing surfaces on the encapsulated stent strips were each attached to an INSTRON tester and the tester actuated to peel the strips. Table 2, below, summarizes the results of the peel test and reflects the bond strength of the samples tested.

TABLE 2

| Run | Average Bond Strength (A & B) [n = 10] g/mm | Std. Dev. |
|---|---|---|
| 1 | 24.735 | 0.0332 |
| 2 | 28.917 | 0.0511 |
| 3 | 21.688 | 0.0379. |
| 4 | 19.648 | 0.0447 |
| 5 | 17.168 | 0.0220 |
| 6 | 26.543 | 0.0163 |
| 7 | 20.178 | 0.0306 |
| 8 | 20.270 | 0.0541 |
| 9 | 37.245 | 0.0397 |

Physical and Structural Characterization Test Procedures

The physical and structural test data obtained from testing material obtained from each of the foregoing examples is set forth in Tables 3–8, below. The tests used to generate the data are based upon the standards developed by the Association for the Advancement of Medical Instrumentation (AAMI) and published in the document entitled "Cardiovascular Implants—Vascular Prostheses" and are also approved by the American National Standards Institute (ANSI). The following describes the specific test procedures used to generate the following physical and structural characterization on the inventive radially expandable ePTFE endoluminal graft.

1. Wall Thickness (WT).

(a) Base Graft: This test was performed on an optical microscope equipped with a vernier stage and eyepiece cross hairs. A 2 cm segment was cut from the graft and mounted on a glass slide with the cut end parallel to the lens. Four measurements of the wall were taken on the circumference 90° apart, and averaged for the representative wall thickness.

(b) Expanded Graft: The above procedure could not be used because the graft material was too thin to be stood upright. Accordingly, a calibrated constant pressure thickness gauge, or snap gauge, was used. A 2 cm segment of the expanded graft sample was flattened on a board and three measurements were taken from different areas of the sample. These values were then divided by 2 to obtain the individual wall thickness and then averaged for the reported wall thickness.

2. Radial Tensile Strength (RTS).

A 1 cm graft segment is mounted onto vice radial-fixtures on an INSTRON tensile tester. The sample is then pulled radially at a rate of 1 in/min to elongate the internal diameter until failure occurs. The peak force is noted and the RTS value is calculated according to the following equation:

$$RTS = \frac{(16.13)(F_p)}{WT_i}$$

where $F_p$ is the recorded peak force in lbs and $WT_i$ is the initial wall thickness of the sample and the RTS value is expressed in psi units.

3. Internodal Distance (IND).

IND measurement is an evaluation of the node-fibril microstructure of the ePTFE graft. A 1 cm graft segment is cut longitudinally and the sample is flattened into a sheet. The surface to be studied is placed face up on a glass slide prepared with double sided tape. The surface is colored using a contrast dye such as aniline dye. Using an optical microscope with a calipered stage and reticle, the average distance between 2 adjacent nodes is recorded. Three measurements are taken per sample for each side. These readings are then averaged for each of the inner surface ($IND_i$) and the outer surface ($IND_o$) of the ePTFE graft and are expressed in $\mu$ or $1\times10^{-6}$ meters.

4. Water Entry Pressure (WEP).

Water entry pressure is an indirect measurement of the porosity of the graft which uses pressurized water to evaluate the graft's ability to retain fluid under pressure. Both ends of a 9 cm graft sample are securely clamped with hemostats. A 22 gauge hypodermic needle is then introduced at a 45° angle through the graft wall land into the lumen. The graft is then slowly filled with distilled water until the internal water pressure reaches 0.8 to 1.8 psi. The pressure is then increased slowly until the first drop of water appears on the outside surface of the graft. The pressure, in psi, at which the water first appears is the WEP value.

5. Longitudinal Foreshortening (LFS).

Longitudinal foreshortening is a measurement of the amount by which the graft foreshortens upon radial expansion. A line is drawn along the length of every sample to be tested. The length of the line is measured both before and after radial expansion and the change in length is converted into a percentage by dividing the difference between initial and final lengths and dividing by the initial length.

Radial Expansion Protocol and Test Results

The following ePTFE grafts were selected for radial expansion testing and characterization:

1. 6 mm ID Regular Wall ePTFE Graft (IMPRA Lot 34396).
2. 3 mm ID Thin Wall ePTFE Graft (IMPRA Lot 34391).
3. 3 mm rePTFE Graft (ERF 1683).
4. 3 mm rePTFE Graft (ERF 1687).
4. 3 mm rePTFE Graft (ERF 1689).
6. 3 mm rePTFE Encapsulated Graft ($ERF_{encap}$).

Each of the foregoing samples were radially expanded using commercially available angioplasty balloon catheters. Radial expansion was conducted in a water tank held at a constant temperature of 37° C. maintained by a circulation pump and heater apparatus. An electric gear pump (Micropump INTEGRAL Series Model No. HGR004) connected to a variable DC voltage supply was used to provide the required fluid pressure to inflate the balloons. A bypass valve was set to bypass expansion flow if pressures above the rated burst pressure of the balloon were reached. Radial expansion was conducted using balloon catheters as follows:

3 mm Grafts
  (a) 9 mm expansion (3×) using a 9 mm×8 cm long angioplasty balloon catheter.
  (b) 12 mm expansion (4×) using a 12 mm×8 cm long angioplasty balloon catheter.
  (c) 15 mm expansion (5×) using a 15 mm×8 cm long angioplasty balloon catheter.

6 mm Graft
  (a) 18 mm expansion (3×) using a 18 mm×8 cm long angioplasty balloon catheter.
  (b) 24 mm expansion (4×) using a 24 mm×8 cm long angioplasty balloon catheter.
  (c) 30 mm expansion (5×) using a 30 mm×5 cm long angioplasty balloon catheter.

Each graft sample length (70–80 cm) was cut into 2 halves. A first was used for base graft testing and the second half was used for radial expansion. The second half for radial expansion was again cut into three 12 cm sections and each section was numbered with the graft number and an identifier indicating which test it was to be used for, e.g., 3×, 4× or 5× expansion. Each segment was then radially expanded to the maximum balloon diameter in the water bath then held for 1 minute. For the larger expansion ratios, i.e., 5×, it was necessary to pre-expand the graft in order to permit the graft lumen to accept the larger profile balloon. After radial expansion, the balloon was deflated, and the graft removed and set aside for testing.

Tables 3–7 set forth the averaged raw data obtained from testing a 6 mm ID standard PTFE vascular graft (Lot 34396, IMPRA, Inc., Tempe, Ariz.), a 3 mm ID standard PTFE vascular graft (Lot 34391, IMPRA, Inc. Tempe Ariz.), and the inventive rePTFE grafts, ERF 1683, ERF 1687, and ERF 1689. FIGS. 13A–24C are the scanning electron micrographs taken of the inner surface and the outer surface of each of the grafts for which the test data in Tables 4–7 is reflected.

TABLE 3

| | Graft: | | | |
|---|---|---|---|---|
| Lot 34396 | 6 mm ID RW PTFE Graft | | | |
| | Base | 3X | 4X | 5X |
| $IND_o$ | 33 ± 1.3 | 31 ± 1.0 | 33 ± 0.9 | 32 ± 0.9 |
| $IND_i$ | 30 ± 1.2 | 30 ± 1.4 | 31 ± 0.7 | 31 ± 0.8 |
| WEP | 5.4 ± 0.23 | 5.38 ± 0.53 | 6 ± 0.52 | 8.5 ± 1.0 |
| WT | 0.72 ± .003 | 0.5 ± 0.032 | 0.36 ± 0.27 | 0.33 ± 0.14 |
| RTS | 1143 ± 966 | 879 ± 80.6 | 897 ± 310.8 | 1110 ± 196.5 |
| FSHT (%) | n/a | 1.5 ± 2.34 | 4.7 ± 3.11 | 3.5 ± 2.40 |

TABLE 4

| | Graft: | | | |
|---|---|---|---|---|
| Lot 34391 | 3 mm TW PTFE Graft | | | |
| | Base | 3X | 4X | 5X |
| $IND_o$ | 33 ± 0.8 | 33 ± 0.8 | 32 ± 0.5 | 33 ± 0.9 |
| $IND_i$ | 31 ± 1.2 | 31 ± 1.2 | 31 ± 0.8 | 29 ± 0.9 |
| WEP | 5.5 ± 0.48 | 5.5 ± 0.29 | 5.8 ± 0.42 | 6.2 ± 0.6 |
| WT | 0.38 ± .005 | 0.29 ± 0.009 | 0.25 ± 0.005 | 0.23 ± 0.007 |
| RTS | 1321 ± 311.1 | 856 ± 249.9 | 955 ± 177.9 | 880 ± 187.3 |
| FSHT (%) | n/a | 3.5 ± 2.43 | 3.5 ± 2.42 | 3.0 ± 2.54 |

TABLE 5

| | Graft: | | | |
|---|---|---|---|---|
| ERF 1683 | 3 mm TW | | | |
| | Base | 3X | 4X | 5X |
| $IND_o$ | 16.4 | 15.8 | 17.5 | 15 |
| $IND_i$ | n/a | 14.3 | 12.5 | 16.5 |
| WEP | 8.08 | 8.67 | 9.33 | 7.97 |
| WT | 0.37 | 0.37 | 0.26 | 0.19 |
| RTS | 487.02 | 632.59 | 1007.16 | 1051.15 |
| FSHT (%) | n/a | n/a | n/a | n/a |

TABLE 6

| | Graft: | | | |
|---|---|---|---|---|
| ERF 1687 | 3 mm TW | | | |
| | Base | 3X | 4X | 5X |
| $IND_o$ | 22.4 | 39 | 42.5 | 39.3 |
| $IND_i$ | n/a | 32.5 | 33.5 | 36 |
| WEP | 4.06 | 4.53 | 5.07 | 5.43 |
| WT | 0.39 | 0.14 | 0.08 | 0.07 |
| RTS | 749 | 791.86 | 1016.54 | 1550.65 |
| FSHT (%) | n/a | n/a | n/a | n/a |

TABLE 7

| | Graft: | | | |
|---|---|---|---|---|
| ERF 1689 | 3 mm TW | | | |
| | Base | 3X | 4X | 5X |
| $IND_o$ | 18.2 | 22.5 | 26.8 | 25 |
| $IND_i$ | n/a | 17.5 | 23.5 | 22.5 |

TABLE 7-continued

| | Graft: | | | |
|---|---|---|---|---|
| | ERF 1689 | 3 mm TW | | |
| | Base | 3X | 4X | 5X |
| WEP | 5.14 | 5.97 | 6.74 | 6.57 |
| WT | 0.388 | 0.13 | 0.11 | 0.08 |
| RTS | 667.2 | 791.86 | 1017 | 1550.65 |
| FSHT (%) | n/a | n/a | n/a | n/a |

It is significant to note, paradoxically, that despite the decreases in node density and in fibril density observed as a result of increased degrees of radial expansion, the water entry pressure of the radially expanded graft increases as the graft is radially expanded. The increase in WEP values, as a function of radial expansion, is the result of the increased tortuosity of the rePTFE material microstructure as it is radially expanded from its original diameter to its expanded diameter in each of the rePTFE samples tested.

It will be seen and appreciated by those skilled in the art that an inventive rePTFE tubular graft suitable for endoluminal radial expansion at applied pressures of less than 6 atm has been described with reference to its preferred embodiments and with reference to an inventive method for making the rePTFE tubular endoluminal grafts. The inventive rePTFE tubular grafts each consist of a longitudinally expanded polytetrafluoroethylene tubular member having a continuous substantially concentric wall surface which has no seam and which is radially deformable between about 50% to about 700% its original diameter with application of a radially directed outward pressure of less than about 6 atm without loss of structural integrity. Structural integrity is considered retained where the microstructure of the ePTFE after radial expansion is substantially free of broken or fractured fibrils and where the following factors are met: 1) IND remains substantially the same as the unexpanded graft; 2) water entry pressure as measured by Association for the Advancement of Medical Instrumentation (AAMI) test method 8.2.4 remains within ±60% of the water entry pressure of the unexpanded graft; 3) the wall thickness of the graft, as determined by AAMI test method 8.7.4, maintains its concentricity as determined by a substantially uniform wall thickness within ±30% about the circumference of the graft; 4) average post-radial expansion wall thickness remains within about ±70% of the average pre-radial expansion wall thickness as determined by AAMI test method 8.7.4; 5) longitudinal tensile strength as AAMI test method 8.3.2 remains within ±100% of the value of the unexpanded graft, when normalized for wall thickness; 6) radial tensile strength as measured by AAMI test method 8.3.1 remains within ±40% of the value of the unexpanded graft, when normalized for wall thickness; and 7) is free of gross tears or fractures.

What is claimed is:

1. A continuous tubular structure comprising an expanded polytetrafluoroethylene material having a predetermined wall thickness and a microstructure characterized by a plurality of nodes interconnected by fibrils, the fibrils having an orientation substantially parallel to a longitudinal axis of the polytetrafluoroethylene tubular material throughout the wall thickness of the tubular structure and the nodes having a longitudinal axis substantially perpendicular to the longitudinal axis of the polytetrafluoroethylene material, the polytetrafluoroethylene material of the tubular structure being capable of undergoing radial deformation from an original unexpanded diameter of the tubular structure to a larger diameter of the tubular structure by application of a positive pressure applied through the lumen of the tubular structure and radially outward therefrom which causes a plurality of the nodes in the microstructure to undergo elongation along the longitudinal axis of the nodes, while substantially retaining an average internodal distance throughout the wall thickness of the radially deformed tubular structure.

2. The continuous tubular structure according to claim 1, wherein the expanded polytetrafluoroethylene tubular material is radially deformable between about 50% to 700% its original diameter without loss of structural integrity.

3. The continuous tubular structure according to claim 2, wherein the polytetrafluoroethylene material has longitudinal and radial tensile strengths and an average node length, and is radially deformable to at least 50% its original diameter at applied positive pressures less than about 6 atm.

4. The continuous tubular structure according to claim 3, wherein the tubular structure at the original unexpanded diameter and the larger diameter each have a water entry pressure value and wherein the expanded polytetrafluoroethylene is radially deformable to between 50% to 700% its original diameter with the water entry pressure value of the radially deformed material remaining within ±60% of the water entry pressure value of the tubular material in its original unexpanded diameter.

5. The continuous tubular structure according to claim 3, wherein the expanded polytetrafluoroethylene is radially deformable to between 50% to 700% its original diameter wherein wall thickness of the graft maintains its concentricity and is free of gross tears or fractures.

6. The continuous tubular structure according to claim 3, wherein the expanded polytetrafluoroethylene material is radially deformable to between 50% to 700% its original diameter wherein the longitudinal tensile strength remains within ±100% of the longitudinal tensile strength of the material in its original unexpanded diameter.

7. The continuous tubular structure according to claim 3, wherein the expanded polytetrafluoroethylene material is radially deformable to between 50% to 700% its original diameter wherein the radial tensile strength remains within ±40% of the radial tensile strength of the material in its original unexpanded diameter.

8. The continuous tubular structure according to claim 3, wherein the expanded polytetrafluoroethylene material is radially deformable to between 50% to 700% its original diameter wherein average nodal elongation in the radially deformed tubular structure is no more than about 300% the average node length of the tubular structure in its original unexpanded diameter.

9. The continuous tubular structure according to claim 3, further including a radially expandable stent member concentrically positioned within the lumen of the tubular structure.

10. The continuous tubular structure according to claim 9, wherein the radially expandable stent member is selected from the group of stents consisting of balloon expandable, self expanding and memory shape stent members.

11. The continuous tubular structure according to claim 10, further including a second continuous tubular structure comprised of polytetrafluoroethylene concentricity positioned with the lumen of the stent member and in intimate contact with the stent member and the continuous tubular structure.

12. The continuous tubular structure according to claim 1, further including a radially expandable stent member concentrically positioned about at least one of an outer, abluminal surface and a luminal surface of the continuous tubular structure.

13. The continuous tubular structure according to claim 12, wherein the radially expandable stent member is selected from the group of stents consisting of balloon expandable, self expanding, and shape memory stent members.

14. A tubular expanded polytetrafluoroethylene member having a determined wall thickness, comprising a material microstructure characterized by a plurality of nodes interconnected by fibrils, the fibrils having an orientation substantially parallel to a longitudinal axis of the tubular expanded polytetrafluoroethylene member and throughout the redetermined wall thickness thereof and the nodes having a longitudinal axis substantially perpendicular to the longitudinal axis of the tubular expanded polytetrafluoroethylene member, the tubular expanded polytetrafluoroethylene member being capable of undergoing radial deformation under an influence of a positive pressure of less than or equal to about 6 atm applied through the lumen of the polytetrafluoroethylene tubular material and directed radially outward therefrom which acts to cause at least some of the nodes to elongate along their longitudinal axis while substantially retaining an average internodal distance throughout the microstructure of the radially deformed tubular expanded polytetrafluoroethylene member which is substantially the same as that of the non-radially deformed tubular expanded polytetrafluoroethylene member.

* * * * *